US008071730B2

(12) United States Patent
Goetsch et al.

(10) Patent No.: US 8,071,730 B2
(45) Date of Patent: Dec. 6, 2011

(54) ANTI-JAM-A ANTIBODIES

(75) Inventors: Liliane Goetsch, Ayze (FR); Nathalie Corvaia, Collonges sous Saleve (FR); Jean-François Haeuw, Beaumont (FR); Cédric Bes, Ambilly (FR)

(73) Assignee: Pierre Fabre Medicament, Boulogne (FR)

( * ) Notice: Subject to any disclaimer, the term of this patent is extended or adjusted under 35 U.S.C. 154(b) by 420 days.

(21) Appl. No.: 12/125,726

(22) Filed: May 22, 2008

(65) Prior Publication Data
US 2010/0092455 A1 Apr. 15, 2010

Related U.S. Application Data

(63) Continuation of application No. PCT/EP2007/062760, filed on Nov. 23, 2007.

(30) Foreign Application Priority Data

Nov. 24, 2006 (FR) ..................................... 06 10329

(51) Int. Cl.
C07K 16/00 (2006.01)
C07K 17/00 (2006.01)
C07K 17/14 (2006.01)
C12P 21/08 (2006.01)
A61K 39/395 (2006.01)
A61K 39/00 (2006.01)

(52) U.S. Cl. ............... 530/387.1; 530/387.3; 530/388.1; 530/391.1; 530/391.3; 424/130.1; 424/133.1; 424/141.1; 424/178.1

(58) Field of Classification Search .................... None
See application file for complete search history.

(56) References Cited

U.S. PATENT DOCUMENTS 6,235,883 B1 * 5/2001 Jakobovits et al. ...... 530/388.22
6,677,436 B1 * 1/2004 Sato et al. .................. 530/387.3

FOREIGN PATENT DOCUMENTS

WO   WO 2005/060457 A2    7/2005
WO   WO 2006/008076 A2    1/2006
WO   WO 2007127476 A2 * 11/2007

OTHER PUBLICATIONS

Skolnick and Fetrow. From genes to protein structure and function: novel applications of computational approaches in the genomic era. Trends in Biotechnology, 2000. vol. 18, pp. 34-39.*
Mac Callum, Martin and Thornton. Antibody-antigen interactions: contact analysis and binding site topography. Journal of Molecular Biology, 1996. vol. 262, pp. 732-745.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Vajdos, Adams, Breece, Presta, De Vos, and Sidhu. Comprehensive functional maps of the antigen-binding site of an anti-ErbB2 antibody obtained by shotgun scanning mutagenesis. Journal of Molecular Biology, 2002. vol. 320, pp. 415-428.*
Wu, Nie, Huse, and Watkins. Humanization of a murine monoclonal antibody by simultaneous optimization of framework and CDR residues. Journal of Molecular Biology, 1999. vol. 151-162.*
Rudikoff, Giusti, Cook, and Scharff. Single amino acid substitution altering antigen-binding specificity. Proceedings of the National Academy of Sciences, 1982. vol. 79, pp. 1979-1983.*
De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*
Holm, Jafari, and Sundstrom. Functional mapping and single chain construction of the anti-cytokeratin 8 monoclonal antibody TS1. Molecular Immunology, 2007. vol. 44, pp. 1075-1084.*
Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*
Lefranc, "Unique database numbering system for immunogenetic analysis," *Immunology Today*, Nov. 1997, p. 509, vol. 18 No. 11.
Lefranc et al., "IMGT unique numbering for immunoglobulin and T cell receptor variable domains and Ig superfamily V-like domains," *Developmental and Comparative Immunology*, 2003, pp. 55-77, vol. 27, Elsevier Science Ltd.
Rulz et al., IMGT gene identification and Colliers de Perles of human immunoglobulins with known 3D structures, *Immunogenetics*, 2002, vol. 53, pp. 857-883, Springer-Verlag.
Kaas et al., "IMGT Colliers de Perles: Standardized Sequence-Structure Representations of the IgSF and MhcSF Superfamily Domains," *Current Bioinformatics*, 2007, vol. 2, pp. 21-30, Bentham Science Publishers Ltd.
Kaas et al., "IMGT/3Dstructure-DB and IMGT/StructuralQuery, a database and a tool for immunoglobulin, T cell receptor and MHC structural data," *Nucleic Acids Research*, 2004, pp. D208-D210, vol. 32, Oxford University Press.
Smith et al., "Comparison of Biosequences," *Advances in Applied Mathematics*, 1981, pp. 482-489, vol. 2, Academic Press, Inc.
Needleman et la., "A General Method Applicable to the Search for Similarities in the Amino Acid Sequence of Two Proteins," *J. Mol. Biol.*, 1970, pp. 443-453, vol. 48, Elsevier, BV.
Pearson et al., "Improved tools for biological sequence comparison," *Proc. Natl. Acad. Sci. USA*, Apr. 1988, pp. 2444-2448, vol. 85, Elsevier Science BV.

(Continued)

*Primary Examiner* — Anne M. Gussow
(74) *Attorney, Agent, or Firm* — Buchanan Ingersoll & Rooney PC

(57) ABSTRACT

The present invention relates to novel isolated antibodies, derived compounds, and functional isolated antibody fragments, capable of inhibiting the proliferation of tumor cells in vitro and/or in vivo and obtained by functional screening.
More particularly, the present invention relates to the 6F4 antibody, specific to the JAM-A protein, as well as its use for the treatment of cancer. Pharmaceutical compositions composed of these antibodies are also covered.

21 Claims, 24 Drawing Sheets

OTHER PUBLICATIONS

Tatusova et al., "Blast 2 Sequences, a new tool for comparing protein and nucleotide sequences," *FEMS Microbiology Letters*, 1999, pp. 247-250, vol. 174.

Skerra, "Anticalins': a new class of engineered ligand-binding proteins with antibody-like properties," *Reviews in Molecular Biotechnology*, 2001, pp. 257-275, vol. 74, Elsevier Science BV.

Kohl et al., "Designed to be stable: Crystal structure of a consensus ankyrin repeat protein," PNAS, Feb. 18, 2003, pp. 1700-1705, vol. 100, No. 4, U.S. National Academy of Sciences.

Bes et al., "PIN bodies: A new class of antibody-like proteins with CD4 specificity derived from the protein inhibitor of neuronal nitric oxide synthase," *Biochemical and Biophysical Research Communications*, 2006, pp. 334-344, vol. 343, Elsevier Inc.

Nicaise et al., "Affinity transfer by CDR grafting on a nonimmunoglobulin scaffold," *Protein Science*, 2004, pp. 1882-1891, vol. 13, Cold Spring Harbor Laboratory Press, downloaded form www.proteinscience.org.

Bes et al., "Efficient CD4 binding and immunosuppressive properties of the 13B8.2 monoclonal antibody are displayed by its CDR-H1-derived peptide CB1," *FEBS Letters*, 2001, pp. 67-74, vol. 508, Elsevier Science B.V.

Verhoeyen et al., "Engineering of Antibodies," *BioEssays*, Feb./Mar. 1998, pp. 74-78, vol. 8, No. 2, Wiley Interscience.

Verhoeyen et al., "Reshaping Human Antibodies: Grafting an antilysozyme Activity," *Science*, Mar. 25, 1988, pp. 1534-1536, vol. 239, downloaded from www.sciencemag.org.

Jones et al., "Replacing the complementarity-determining regions in a human antibody with those from a mouse," *Nature*, May 29, 1986, pp. 522-525, vol. 321, Nature Publishing Group.

Riechmann et al., "Reshaping human antibodies for therapy," *Nature*, Mar. 24, 1988, pp. 323-327, vol. 332, Nature Publishing Group.

Singer et al., "Optimal Humanization of 1B4, an Anti-CD18 Murine Monoclonal Antibody, Is Achieved by Correct Choice of Human V-Region Framework Sequences," *The Journal of Immunology*, Apr. 1, 1993, pp. 2844-2857, vol. 150, No. 7,The American Association of Immunologists.

Mountain et al., "Engineering Antibodies for Therapy," *Biotechnology and Genetic Engineering Reviews*, Dec. 10, 1992, pp. 1-142, vol. 10, Intercept Ltd.

Junghans et al., "Advanced generation anti-CEA designer T cells for adenocarcinoma therapy," *Proceedings of the American Association for Cancer Research*, Apr. 2006, #1183, p. 280, vol. 47, XP001245692.

Bebbington et al., "High-Level Expression of a Recombinant Antibody from Myeloma Cells Using a Glutamine Synthetase Gene as an Amplifiable Selectable Marker," *Bio/Technology*, Feb. 1992, pp. 169-175, vol. 10.

Kostrewa et la., "X-ray structure of junctional adhesion molecule: structural basis for homophilic adhesion via a noval dimerization motif," *The EMBO Journal*, 2001, pp. 4391-4398, vol. 20 No. 16, European Molecular Biology Organization.

Prota et al., "Crystal structure of human junctional adhesion molecule 1: Implications for reovirus binding," *PNAS*, Apr. 29, 2003, pp. 5366-5371, vol. 100, No. 9, U.S. National Academy of Sciences.

Bazzoni et al., "Homophilic Interaction of Junctional Adhesion Molecule," *The Journal of Biological Chemistry*, Oct. 6, 2000, pp. 30970-30976, vol. 275 No. 40, The American Society for Biochemistry and Molecular Biology, Inc.

Liu et al., "Human junction adhesion molecule regulates tight junction resealing in epithelia," *Journal of Cell Science*, 2000, pp. 2363-2374, vol. 113, The Company of Biologists Limited.

Ebnet et al., "Junctional Adhesion Molecule Interacts with the PDZ Domain-containing Proteins AF-6 and ZO-1," *The Journal of Biological Chemistry*, 2000, pp. 27979-27988, vol. 275 No. 36, The American Society for Biochemistry and Molecular Biology, Inc.

Itoh et al., "Junctional adhesion molecule (JAM) binds to PAR-3: a possible mechanism for the recruitment of PAR-3 to tight junctions," *The Journal of Cell Biology*, Aug. 6, 2001, pp. 491-497, vol. 154, No. 3, The Rockefeller University Press.

Hamazaki et al., "Multi-PDZ Domain Protein 1 (MUPP1) Is Concentrated at Tight Junctions through Its Possible Interaction with Claudin-1 and Junctional Adhesion Molecule," *The Journal of Biological Chemistry*, Jan. 4, 2002, pp. 455-461, vol. 277 No. 1, The American Society for Biochemistry and Molecular Biology, Inc.

Mandell et al., "Involvement of the Junctional Adhesion Molecule-1 (JAM1) Homodimer Interface in Regulation of Epithelial Barrier Function," *The Journal of Biological Chemistry*, Apr. 16, 2004, pp. 16254-16262, vol. 279 No. 16, The American Society for Biochemistry and Molecular Biology, Inc.

Neik et al., "Junctional adhesion molecule-A-induced endothelial cell migration on vitronectin is integrin $\alpha_v \beta_3$ specific," *Journal of Cell Science*, 2006, pp. 490-499, vol. 119, The Company of Biologists 2006.

Naik et al., "Signaling through JAM-1 and $\alpha_v \beta_3$ is required for the angiogenic action of bFGF: dissociation of the JAM-1 and $\alpha_v \beta_3$ complex," *Blood*, Sep. 15, 2003, pp. 2108-2114, vol. 102, No. 6, The American Society of Hematology.

Naik et al., "Essential Role of Junctional Adhesion Molecule-1 in Basic Fibroblast Growth Factor-Induced Endothelial Cell Migration," *Arterioscler Thromb Vasc Biol.*, 2003, DOI: 10.1161/01.ATV.0000093982.84451.87, American Heart Association, Inc.

Williams et al., "Identification and Characterisation of human Junctional Adhesion Molecule (JAM)," *Molecular Immunology*, 1999, pp. 1175-1188, vol. 36, Elsevier Science Ltd.

Malergue et al., "A novel immunoglobulin superfamily junctional molecule expressed by antigen presenting cells, endothelial cells and platelets," *Molecular Immunology*, 1998, pp. 1111-1119, vol. 35, Elsevier Science Ltd.

Kornecki et al., "Activation of Human Platelets by a Stimulatory Monoclonal Antibody," *The Journal of Biological Chemistry*, 1990, pp. 10042-10048, vol. 265 No. 17, The American Society for Biochemistry and Molecular Biology, Inc.

Gupta et al., "Platelet Agonist F11 Receptor Is a Member of the Immunoglobulin Superfamily and Identical with Junctional Adhesion Molecule (JAM): Regulation of Expression in Human Endothelial Cells and Macrophages," *IUBMB Life*, 2000, pp. 51-56, vol. 50, IUBMB.

Mandell et al., "The JAM family of proteins," *Advanced Drug Delivery Reviews*, 2005, pp. 857-867, vol. 57, Elsevier BV.

Naik et al., "Mechanisms of platelet activation by a stimulatory antibody; cross-linking of a novel platelet receptor for monoclonal antibody F11 with the Fc•RII receptor," *Biochemistry Journal*, 1995, pp. 155-162, vol. 310, Portland Press.

Sobocka et al., "Cloning of the human platelet F11 receptor: a cell adhesion molecule member of the immunoglobulin superfamily involved in platelet aggregation," *Blood*, Apr. 15, 2000, pp. 2600-2609, vol. 95 No. 8, The American Society of Hematology.

Babinska et al., "Two Regions of the Human Platelet F11 Receptor (F11R) Are Critical for Platelet Aggregation, Potentiation and Adhesion," *Thromb Haemost*, 2002, pp. 712-721, vol. 87, Schattauer GmbH, Stuttgart, Germany.

Del Maschio et al., "Leukocyte Recruitment in the Cerebrospinal Fluid of Mice with Experimental Meningitis Is Inhibited by an Antibody to Junctional Adhesion Molecule (JAM)," *Brief Definitive Report*, Nov. 1, 1999, vol. 190, No. 9, The Rockefeller University Press.

Ostermann et la., "JAM-1 is a ligand of the $\beta_2$ integrin LFA-1 involved in transendothelial migration of leukocytes," *Nature Immunology*, Feb. 2002, pp. 151-158, vol. 3, No. 2, Nature Publishing Group.

Barton et al., "Junction Adhesion Molecule Is a Receptor for Reovirus," *Cell*, Feb. 9, 2001, pp. 441-451, vol. 104, Cell Press.

Forrest et al., "Structure-Function Analysis of Reovirus Binding to Junctional Adhesion Molecule 1," *The Journal of Biological Chemistry*, Nov. 28, 2003, pp. 48434-48444, vol. 278 No. 48, The American Society for Biochemistry and Molecular Biology, Inc.

Chen et al., "Selection and Analysis of an Optimized Anti-VEGF Antibody: Crystal Structure of an Affinity-matured Fab in Complex with Antigen," *J. Mol. Biol.*, 1999, pp. 865-881, vol. 293, Academic Press.

Maloney et al., "An Anti-Insulin-like Growth Factor I Receptor Antibody That Is a Potent Inhibitor of Cancer Cell Proliferation," *Cancer Research*, Aug. 15, 2003, pp. 5073-5083, vol. 63, American Association for Cancer Research.

Li et al., "Single-chain antibodies against human insulin-like growth factor I receptor: expression, purification, and effect on tumor growth," *Cancer Immunol Immunother*, 2000, pp. 243-252, vol. 49, Springer-Verlag.

Holliger et al., "Engineering antibodies for the clinic," *Cancer and Metastasis Reviews*, 1999, pp. 411-419, vol. 18, Kluwer Academic Publishers, Netherlands.

Jackson-Booth et al., Inhibition of the Biologic Response to Insulin-like Growth Factor I in MCF-7 Breast Cancer Cell by a New Monoclonal Antibody to the Insulin-like Growth Factor-I Receptor. The Importance of Receptor Down-regulation, *Horm Metab Res*, 2003, pp. 850-856, vol. 35, Georg Thieme Verlag.

Glennie et al., "Preparation and Performance of Bispecific F(ab'γ)$_2$ Antibody Containing Thioether-Linked Fab' γ Fragments," *The Journal of Immunology*, Oct. 1, 1987, pp. 2367-2375, vol. 139, No. 7, The American Association of Immunologists.

Park et al., "Generation and characterization of a novel tetravalent bispecific antibody that binds to hepatitis B virus surface antigens," *Molecular Immunology*, 2000, pp. 1123-1130, vol. 37, Elsevier Science Ltd.

Stewart et al., "Contents" *Solid Phase Peptide Synthesis Second Edition*, 1984, pp. vii-xi, Pierce Chemical Company, Rockford, IL.

Staerz et al., "Hybrid hybridoma producing a bispecific monoclonal antibody that can focus effector T-cell activity," *Proc. Natl. Acad. Sci. USA*, 1986, pp. 1453-1457, vol. 83.

Suresh, et al., "Bispecific Monoclonal Antibodies from Hybrid Hybridomas," *Methods in Enzymology*, 1986, pp. 210-228, vol. 121, Academic Press, Inc.

Merchant et al., "An efficient route to human bispecific IgG," *Nature Biotechnology*, Jul. 1998, pp. 677-681, vol. 16, Nature Publishing Group Research.

Krejcarek et al., "Covalent Attachment of Chelating Groups to Macromolecules," *Biochemical and Biophysical Research Communications*, 1977, pp. 581-585, vol. 77 No. 2, Academic Press, Inc.

Brechbiel et al., "Backbone-Substituted DTPA Ligands for $^{90}$Radioimmunotherapy," *Bioconjugate Chem.* 1991, pp. 187-194, vol. 2, American Chemical Society.

Otto A. Gansow, "Newer Approaches to the Radiolabeling of Monoclonal Antibodies by Use of Metal Chelates," *Nucl. Med. Biol.*, 1991, pp. 369-381, vol. 18, Pergamon Press plc.

Meares et al., "Conjugation of Antibodies with Bifunctional Chelating Agents: Isothiocyanate and Bromoacetamide Reagents, Methods of Analysis, and Subsequent Addition of Metal Ions,"*Analytical Biochemistry*, 1984, pp. 68-78, vol. 142, Academic Press, Inc.

Gansow et al., "7. Chelates and antibodies: Current methods and new directions," *Cancer Imaging with Radiolabeled Antibodies*, Goldenberg, D.M., (ed.), 1990, pp. 153-171, Kluwer Academic Publishers.

Skerra, *Engineered protein scaffolds for molecular recognition*, 13 Journal of Molecular Recognition 167-187 (John Wiley & Sons, Ltd., 2000).

\* cited by examiner

6F4 antibody

*Heavy chain (variable domain):*

Nucleotide sequence:
GAGATCCAGCTGCAGCAGTCTGGACCTGAGCTGGTGAAGCCTGGGGCTTCAGTGAAGGTATC CTGCAAGGCTTCTGGTTACTCATTCACTGACTACAGCATGTACTGGGTGAAGCAGAGCCATG
<u>　　　　　　　　　　　　　　CDR 1　　　　　</u>
GAAAGAGCCTTGAGTGGATTGGATATATTGATCCTTACAATGGTGGTACTAGGTACAACCAG
<u>　　　　　　　　　　　　　CDR 2</u>
AAGTTCAAGGGCAAGGCCACATTGACTGTTGACAAGTCCTCCAGCACAGCCTTCATGCATCT CAACAGCCTGACATCTGAGGACTCTGCAGTCTATTACTGTGCAAGACAGACGGACTACTTTG
<u>　　　　　　　　　　　　　　　　　　　　　　　　　　　　　CDR 3</u>
ACTACTGGGGCCAAGGCACCACTCTCACAGTCTCCTCA

Protein sequence: (one-letter code)
EIQLQQSGPELVKPGASVKVSCKASGYSF<u>TDYSMY</u>WVKQSHGKSLEWIG<u>YIDPYNGGTRYNQ</u>
<u>　　　　　　　　　　　　　　　　CDR 1　　　　　　　　　　　　　　　CDR 2</u>
<u>KFKG</u>KATLTVDKSSSTAFMHLNSLTSEDSAVYYCAR<u>QTDYFDY</u>WGQGTTLTVSS
<u>　　　　　　　　　　　　　　　　　　　　　CDR 3</u>

*Light chain (variable domaine):*

Nucleotide sequence:
GACATCCAGATGACACAGTCTCCATCCTCACTGTCTGCATCTCTGGGAGGCAAAGTCACCAT CACTTGCAAGGCAAGCCAAGACATTAACAATTATATAGCTTGGTACCAACACAAGCCTGGAA
<u>　　　　　　　　　　CDR 1</u>
AAGGTCCTAGGCTGCTCATACATTACACATCTACATTACAAGCAGGCATCCCATCAAGGTTC
<u>　　　　　　　　　　　CDR 2</u>
AGTGGAAGTGGGTCTGGGAGAGATTATTCCTTCAGCATCAGCAACCTGGAGCCTGAAGATAT TGGAACTTATTATTGTCTACAGTATGATAATCTGTGGACGTTCGGTGGAGGCACCAAGCTGG
<u>　　　　　　　　　　　　　CDR 3</u>
AAATCAAA

Protein sequence: (one-letter code)
DIQMTQSPSSLSASLGGKVTITC<u>KASQDINNYIA</u>WYQHKPGKGPRLLIH<u>YTSTLQA</u>GIPSRF
<u>　　　　　　　　　　　　　CDR 1　　　　　　　　　　　　　　　CDR 2</u>
SGSGSGRDYSFSISNLEPEDIGTYYC<u>LQYDNLWT</u>FGGGTKLEIK
<u>　　　　　　　　　　　　　　　CDR 3</u>

FIGURE 1

IGKV19-93*01 (IMGT nomenclature): 98.56% (275/279 nt)

```
                        <---------------------- FR1-IMGT ---------------
6F4 VL domain (AA)       D  I  Q  M  T  Q  S  P  S  S  L  S  A  S  L  G  G  K  V  T
6F4 VL domain           gacatccagatgacacagtctccatcctcactgtctgcatctctggaggcaaagtcacc
AJ235935 IGKV19-93*01   ------------------------------------------------------------

----------------->_____ CDR1-IMGT _____<-----
6F4 VL domain (AA)       I  T  C  K  A  S  Q  D  I  N  N  Y                   I  A
6F4 VL domain           atcacttgcaaggcaagccaagacattaacaattat..................atagct
AJ235935 IGKV19-93*01   ------------------------------g---..................------

-------------- FR2-IMGT -------------------->_____ CDR
6F4 VL domain (AA)       W  Y  Q  H  K  P  G  K  G  P  R  L  L  I  H  Y  T  S
6F4 VL domain           tggtaccaacacaagcctggaaaagtcctaggctgctcatacattacacatct......
AJ235935 IGKV19-93*01   ---------------------------------------------------------......

2-IMGT _____<-------------------------------------------
6F4 VL domain (AA)                      T  L  Q  A  G  I  P     S  R  F  S  G  S  G
6F4 VL domain           ...............acattacaagcaggcatccca...tcaaggttcagtggaagtggg
AJ235935 IGKV19-93*01   ...............--------gc-----------...---------------------

--------- FR3-IMGT ----------------------------------------
6F4 VL domain (AA)           S  G  R  D  Y  S  F  S  I  S  N  L  E  P  E  D  I  G
6F4 VL domain           ......tctggagagattattccttcagcatcagcaacctggagcctgaagatattgga
AJ235935 IGKV19-93*01   ......----------------------------------------------------c-

---------->_____ CDR3-IMGT _____<--------------- FR4-IMGT
6F4 VL domain (AA)       T  Y  Y  C  L  Q  Y  D  N  L  W  T  F  G  G  G  T  K  L  E
6F4 VL domain           acttattattgtctacagtatgataatctgtggacgttcggtggaggcaccaagctggaa
AJ235935 IGKV19-93*01   ------------------------------tctac- ------>
6F4 VL domain (AA)       I  K
6F4 VL domain           atcaaac
```

FIGURE 2A

IGKJ1*01 (IMGT nomenclature): 100.0% (38/38 nt)

```
                        CDR3-IMGT _____<----------- FR4-IMGT ------->
6F4 VL domain (AA)                W  T  F  G  G  G  T  K  L  E  I  K
6F4 VL domain           gtggacgttcggtggaggcaccaagctggaaatcaaac
V00777 IGKJ1*01         --------------------------------------
```

FIGURE 2B

IGKV1-33*01 (IMGT nomenclature): 81.36% (227/279 nt)

```
                            <------------------------------------------- FR1 - IMGT
                            1              5              10              15
6F4 VL domain               gac atc cag atg aca cag tct cca tcc tca ctg tct gca tct ctg
                             D   I   Q   M   T   Q   S   P   S   S   L   S   A   S   L
M64856 IGKV1-33*01          --- --- --- --c --- --- --- --- --c --- --- --- --- g-a
                                                                                  V ------------------------------------------>  _____
                                            20              25              30
6F4 VL domain               gga ggc aaa gtc acc atc act tgc aag gca agc caa gac att aac
                             G   G   K   V   T   I   T   C   K   A   S   Q   D   I   N
M64856 IGKV1-33*01          --- -a- -g- --- --- --- --- --- c-- --g --t --- --- --- -g-
                                 D   R                           Q                   S ___ CDR1 - IMGT _____  <---------------------------
                                            35              40              45
6F4 VL domain               aat tat ... ... ... ... ... ... ata gct tgg tac caa cac aag
                             N   Y                            I   A   W   Y   Q   H   K
M64856 IGKV1-33*01          --c --- ... ... ... ... ... ... t-- aa- --- --t --g --g --a
                                                              L   N                Q FR2 - IMGT  ------------------------>  _____  CDR2
                                            50              55              60
6F4 VL domain               cct gga aaa ggt cct agg ctg ctc ata cat tac aca tct ... ...
                             P   G   K   G   P   R   L   L   I   H   Y   T   S
M64856 IGKV1-33*01          --a --g --- -cc --- -a- --c --g --c t-c g-t g-- --c ... ...
                                         A           K           Y   D   A

- IMGT _____  <---------------------------
                                            65              70              75
6F4 VL domain               ... ... ... ... ... aca tta caa gca ggc atc cca ... tca agg
                                                  T   L   Q   A   G   I   P       S   R
M64856 IGKV1-33*01          ... ... ... ... ... -at --g g-- a-- --g --- --- ... --- ---
                                                  N   E   E   T       V ---------------------------- FR3 - IMGT ---------------
                                            80              85              90
6F4 VL domain               ttc agt gga agt ggg ... ... tct ggg aga gat tat tcc ttc agc
                             F   S   G   S   G           S   G   R   D   Y   S   F   S
M64856 IGKV1-33*01          --- --- --- --- --a ... ... --- --- -c- --- -t- a-t --- -c-
                                                                 T           F   F   T ----------------------------------------------------->  ____
                                            95              100             104
6F4 VL domain               atc agc aac ctg gag cct gaa gat att gga act tat tgt cta
                             I   S   N   L   E   P   E   D   I   G   T   Y   Y   C   L
M64856 IGKV1-33*01          --- --- -g- --- c-- --- --- --- --- -c- --a --- --c --- -a-
                                         S       Q                   A                Q _____  CDR3 - IMGT _____  <------------- FR4-IMGT --------
6F4 VL domain               cag tat gat aat ctg tgg acg ttc ggt gga ggc acc aag ctg gaa
                             Q   Y   D   N   L   W   T   F   G   G   G   T   K   L   E
M64856 IGKV1-33*01          --- --- --- --- --c cct c-
                                                 P
```

FIGURE 3A

IGKJ1*01 (IMGT nomenclature): 86.84% (33/38 nt)

```
                    CDR3 - IMGT   <-------------- FR4-IMGT ------------->
6F4 VL DOMAIN            G TGG ACG TTC GGT GGA GGC ACC AAG CTG GAA ATC AAA
                           W   T   F   G   G   G   T   K   L   E   I   K
J00242 IGKJ1*01          - --- --- --- --C CA- --G --- --- G-- --- --- ---
                                           Q                 V
```

FIGURE 3B

| | | | | | | | | | | | | | | | | | | | | | | |
|---|---|---|---|---|---|---|---|---|---|---|---|---|---|---|---|---|---|---|---|---|---|---|
| Sequential numbering | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| IMGT unique numbering (1) | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| Kabat VL numbering (2) | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| murine 6F4 VL | D | I | Q | M | T | Q | S | P | S | S | L | S | A | S | L | G | G | K | V | T | I | T |

CDR1

| | | | | | | | | | | | | | | | | | | | | | |
|---|---|---|---|---|---|---|---|---|---|---|---|---|---|---|---|---|---|---|---|---|---|
| Sequential numbering | 23 | 24 | 25 | 26 | 27 | | 28 | 29 | 30 | 31 | 32 | | | | | | | 33 | 34 | 35 | 36 | 37 |
| IMGT unique numbering (1) | 23 | 24 | 25 | 26 | 27 | | 28 | 29 | 30 | 31 | 32 | 33 | 34 | 35 | 36 | 37 | 38 | 39 | 40 | 41 | 42 | 43 |
| Kabat VH numbering (2) | 23 | 24 | 25 | 26 | 27 | (A-F) | 28 | 29 | 30 | 31 | 32 | | | | | | | 33 | 34 | 35 | 36 | 37 |
| murine 6F4 VL | C | K | A | S | Q | - | D | I | N | N | Y | - | - | - | - | - | - | I | A | W | Y | Q |

CDR2

| | | | | | | | | | | | | | | | | | | | | | |
|---|---|---|---|---|---|---|---|---|---|---|---|---|---|---|---|---|---|---|---|---|---|
| Sequential numbering | 38 | 39 | 40 | 41 | 42 | 43 | 44 | 45 | 46 | 47 | 48 | 49 | 50 | 51 | 52 | | | | | | | |
| IMGT unique numbering (1) | 44 | 45 | 46 | 47 | 48 | 49 | 50 | 51 | 52 | 53 | 54 | 55 | 56 | 57 | 58 | 59 | 60 | 61 | 62 | 63 | 64 | 65 |
| Kabat VH numbering (2) | 38 | 39 | 40 | 41 | 42 | 43 | 44 | 45 | 46 | 47 | 48 | 49 | 50 | 51 | 52 | | | | | | | |
| murine 6F4 VL | H | K | P | G | K | G | P | R | L | L | I | H | Y | T | S | - | - | - | - | - | - | - |

| | | | | | | | | | | | | | | | | | | | | | | |
|---|---|---|---|---|---|---|---|---|---|---|---|---|---|---|---|---|---|---|---|---|---|---|
| Sequential numbering | 53 | 54 | 55 | 56 | 57 | 58 | 59 | | 60 | 61 | 62 | 63 | 64 | 65 | 66 | | | 67 | 68 | 69 | 70 | 71 |
| IMGT unique numbering (1) | 66 | 67 | 68 | 69 | 70 | 71 | 72 | 73 | 74 | 75 | 76 | 77 | 78 | 79 | 80 | 81 | 82 | 83 | 84 | 85 | 86 | 87 |
| Kabat VH numbering (2) | 53 | 54 | 55 | 56 | 57 | 58 | 59 | | 60 | 61 | 62 | 63 | 64 | 65 | 66 | | | 67 | 68 | 69 | 70 | 71 |
| murine 6F4 VL | T | L | Q | A | G | I | P | - | S | R | F | S | G | S | G | - | - | S | G | R | D | Y |

| | | | | | | | | | | | | | | | | | | | | | |
|---|---|---|---|---|---|---|---|---|---|---|---|---|---|---|---|---|---|---|---|---|---|
| Sequential numbering | 72 | 73 | 74 | 75 | 76 | 77 | 78 | 79 | 80 | 81 | 82 | 83 | 84 | 85 | 86 | 87 | 88 | 89 | 90 | 91 | 92 |
| IMGT unique numbering (1) | 88 | 89 | 90 | 91 | 92 | 93 | 94 | 95 | 96 | 97 | 98 | 99 | 100 | 101 | 102 | 103 | 104 | 105 | 106 | 107 | 108 | 109 |
| Kabat VH numbering (2) | 72 | 73 | 74 | 75 | 76 | 77 | 78 | 79 | 80 | 81 | 82 | 83 | 84 | 85 | 86 | 87 | 88 | 89 | 90 | 91 | 92 |
| murine 6F4 VL | S | F | S | I | S | N | L | E | P | E | D | I | G | T | Y | Y | C | L | Q | Y | D | - |

CDR3

| | | | | | | | | | | | | | | | | |
|---|---|---|---|---|---|---|---|---|---|---|---|---|---|---|---|---|
| Sequential numbering | | | | | 93 | 94 | 95 | 96 | 97 | 98 | 99 | 100 | 101 | 102 | 103 | 104 | 105 | 106 |
| IMGT unique numbering (1) | 110 | 111 | 112 | 113 | 114 | 115 | 116 | 117 | 118 | 119 | 120 | 121 | 122 | 123 | 124 | 125 | 126 | 127 | 128 |
| Kabat VH numbering (2) | | | | | 93 | 94 | 95 | 96 | 97 | 98 | 99 | 100 | 101 | 102 | 103 | 104 | 105 | 106 |
| murine 6F4 VL | - | - | - | - | N | L | W | T | F | G | G | G | T | K | L | E | I | K | - |

FIGURE 4

```
                              <--------------------------------- FR1-IMGT ---------------
6F4 VH domain (AA)            E   I   Q   L   Q   Q   S   G   P       E   L   V   K   P   G   A   S   V   K
6F4 VH domain                 gagatccagctgcagcagtctggacct...cagctggtgaagcctggggcttcagtcaag
AF304556 IGHV1S135*01         ---------------------------...------------------------------

----------------->_____ CDR1-IMGT _____<-----
6F4 VH domain (AA)            V   S   C   K   A   S   G   Y   S   F   T   D   Y   S                   M   Y
6F4 VH domain                 gtatcctgcaaggcttctggttactcattcactgactacagc............atgtac
AF304556 IGHV1S135*01         -----------------------------------------a-...............------

--------------- FR2-IMGT -------------------->_____ CDR
6F4 VH domain (AA)            W   V   K   Q   S   H   G   K   S   L   E   W   I   G   Y   I   D   P   Y   N
6F4 VH domain                 tgggtgaagcagagccatggaaagagccttgagtggattggatatattgatccttacaat
AF304556 IGHV1S135*01         ------------------------------------------------------------

2-IMGT _____<-------------------------------------------
6F4 VH domain (AA)            G   G   T           R   Y   N   Q   K   F   K       G   K   A   T   L   I   V
6F4 VH domain                 ggtggtact......agctacaaccagaagttcaag...ggcaaggccacattgactgtt
AF304556 IGHV1S135*01         ---------......--c-------------------...--------------------

--------- FR3-IMGT ------------------------------------------
6F4 VH domain (AA)            D   K   S   S   T   A   F   M   E   L   N   S   L   T   S   E   D   S   A
6F4 VH domain                 gacaagtcctccagcacagccttcatgcatctcaacagcctgacatctgaggactctgca
AF304556 IGHV1S135*01         ------------------------------------------------------------

----------->_____ CDR3-IMGT _____
6F4 VH domain (AA)            V   Y   Y   C   A   R   Q   T   D   Y   F   D   Y   W   G   Q   G   T   T   L
6F4 VH domain                 gtctattactgtgcaagacagacggactactttgactactggggccaaggcaccactctc
AF304556 IGHV1S135*01         ------------------

6F4 VH domain (AA)            T   V   S   S
6F4 VH domain                 acagtctcctcag
```

FIGURE 5A

IGHD-ST4*01 (IMGT nomenclature): 80.00% (4/5 nt)

```
                                     ____ CDR3-IMGT ____
6F4 VH domain (AA)                   A   R   Q   T   D   Y
6F4 VH domain                            cagacg
M23243 IGHD-ST4*01                       .----agctcgggctac
```

FIGURE 5B

IGHJ2*01 (IMGT nomenclature): 100.00% (48/48 nt)

```
                                     _____ CDR3-IMGT _____<-------------FR4------------>
6F4 VL domain (AA)                   Q   T   D   Y   F   D   Y   W   G   Q   G   T   T   L   T   V   S   S
6F4 VH domain                        cagacggactactttgactactggggccaaggcaccactctcacagtctcctca
V00770 IGHJ2*01                      ......------------------------------------------------
```

FIGURE 5C

IGHV1-f*01 (IMGT nomenclature): 75.34% (217/288 nt)

```
                       <------------------------------------ FR1 - IMGT
                       1               5                  10                  15
6F4 VH domain          cag atc cag ctg cag cag tct gga cct ... gag ctg gtg aag cct
                        E   I   Q   L   Q   Q   S   G   P       E   L   V   K   P
Z12305 IGHV1-f*01      --- g-- --- --- gta --- --- --g g-- ... --- g-- aa- --- ---
                            V           V           A               V   K -------------------------------------->
                                       20                  25                  30
6F4 VH domain          cgg gct tca gtc aag gta tcc tgc aag gct tct ggt tac tca ttc
                        G   A   S   V   K   V   S   C   K   A   S   G   Y   S   F
Z12305 IGHV1-f*01      --- --- a-- --- --a a-c --- --- --- -t- --- --a --- a-c ---
                                T           I                   V               Y __ CDR1 - IMGT _____ <-------------------------
                                       35                  40                  45
6F4 VH domain          act gac tac agc ... ... ... ... atg tac tgg gtg aag cag agc
                        T   D   Y   S                    M   Y   W   V   K   Q   S
Z12305 IGHV1-f*01      --c --- --- ta- ... ... ... ... --- c-- --- c-a --- gc-
                                    Y                        H           Q       A FR2 - IMGT -------------------------->  _____ CDR2
                                       50                  55                  60
6F4 VH domain          cat gga aag agc ctg gag tgg att gga tat att gat cct tac aat
                        H   G   K   S   L   E   W   I   G   Y   I   D   P   Y   N
Z12305 IGHV1-f*01      -c- --- --a g-g --- --- --- --g --- ct- g-- --- --- g-a g--
                        P           G                   M       L   V           E   D

- IMGT _____ <-----------------------------------
                                       65                  70                  75
6F4 VH domain          ggt ggt act ... ... agg tac aac cag aag ttc aag ... ggc aag
                        G   G   T           R   Y   N   Q   K   F   K       G   K
Z12305 IGHV1-f*01      --- -aa --a ... ... -ta --- gca g-- --- --- c-- ... --- -ga
                            E               I       A   E                       R ---------------------------- FR3 - IMGT ----------------
                                       80                  85                  90
6F4 VH domain          gcc aca ttg act gtg gac aag tcc tcc agc aca gcc ttc atg cat
                        A   T   L   T   V   D   K   S   S   S   T   A   F   M   H
Z12305 IGHV1-f*01      -t- --c a-a --c -cg --- --c --t a-a ga- --- --- -a- --- g-g
                        V       I       A       T       T   D               Y       E -------------------------------------->  ____
                                       95                  100                 104
6F4 VH domain          ctc aac agc ctg aca tct gag gac tct gca gtc tat tac tgt gca
                        L   N   S   L   T   S   E   D   S   A   V   Y   Y   C   A
Z12305 IGHV1-f*01      --g -g- --- --- -g- --- --- --- a-g --c --g --- --- --- ---
                            S           R                   T _____ CDR3 - IMGT _____
6F4 VH domain          aga cag acg gac tac ttt gac tac tgg ggc caa ggc acc act ctc
                        R   Q   T   D   Y   F   D   Y   W   G   Q   G   T   T   L
Z12305 IGHV1-f*01      -c-
                        T
```

FIGURE 6A

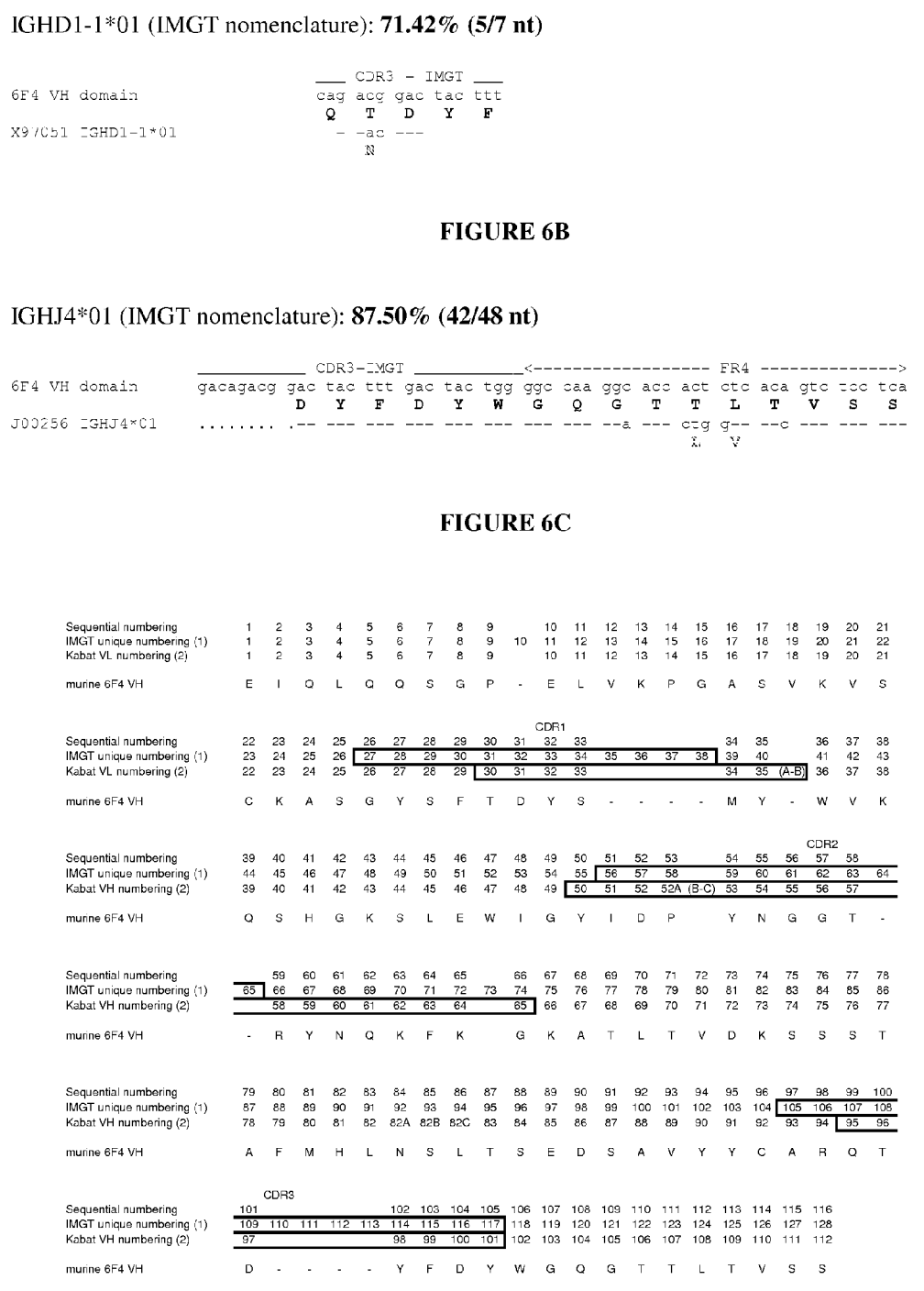

IGHD1-1*01 (IMGT nomenclature): 71.42% (5/7 nt)

```
                        ___ CDR3 - IMGT ___
6F4 VH domain           cag acg gac tac ttt
                         Q   T   D   Y   F
X97051 IGHD1-1*01        -  -ac ---
                             N
```

FIGURE 6B

IGHJ4*01 (IMGT nomenclature): 87.50% (42/48 nt)

```
                  _____ CDR3-IMGT _____<---------------- FR4 -------------->
6F4 VH domain     gacagacg gac tac ttt gac tac tgg ggc caa ggc acc act ctc aca gtc tcc tca
                           D   Y   F   D   Y   W   G   Q   G   T   T   L   T   V   S   S
J00256 IGHJ4*01   ........ .-- --- --- --- --- --- --- --- --a --- ctg g-- --c --- --- ---
                                                                      L   V
```

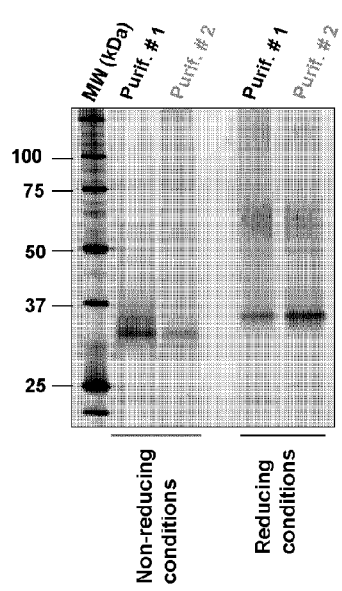 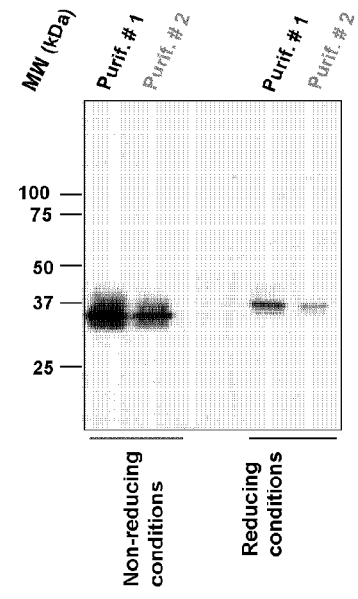
FIGURE 9A                    FIGURE 9B
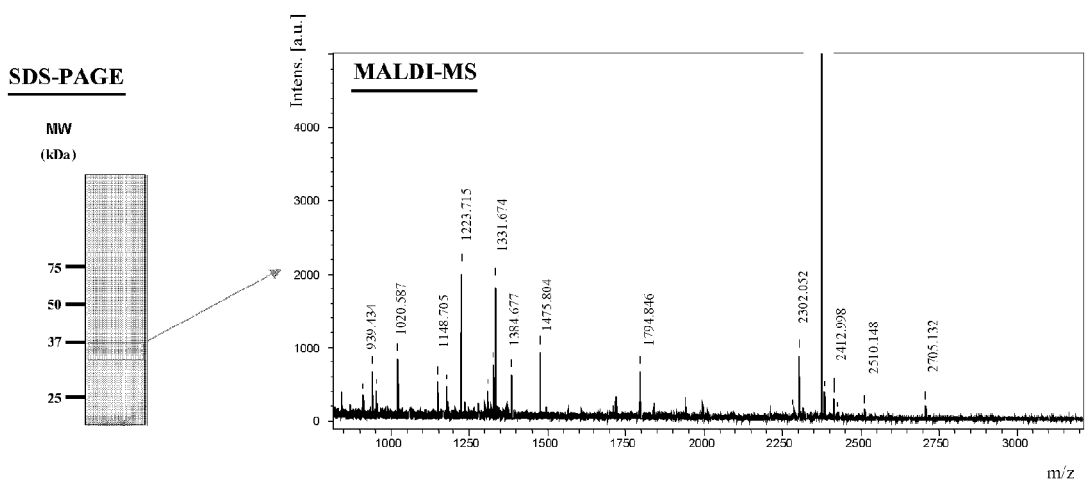
FIGURE 10

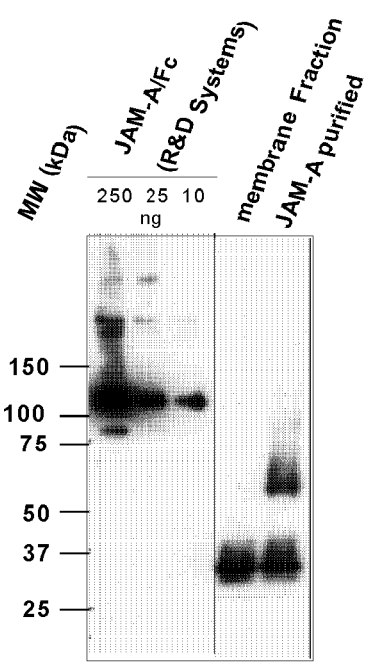 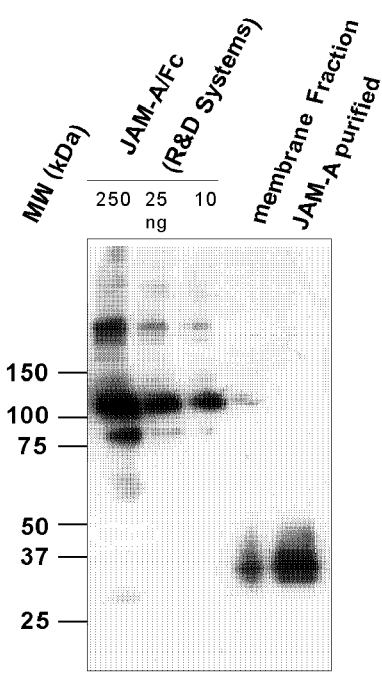
FIGURE 11A  FIGURE 11B
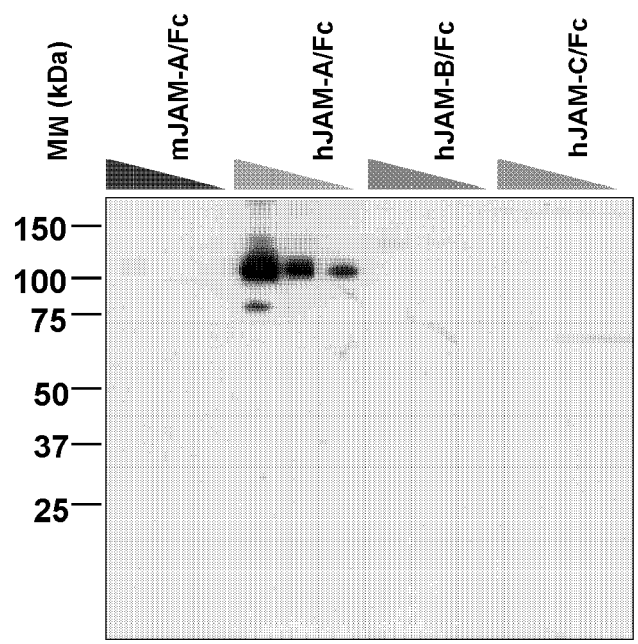
FIGURE 12

```
                         <------------------------------------------ FR1 - IMGT
                         1              5                   10                  15
humanized 6F4 VL domain  D   I   Q   M   T   Q   S   P   S   S   L   S   A   S   V
                                                                                 *

------------------------------------------>  _____
                                             20                  25                  30
humanized 6F4 VL domain  G   D   R   V   T   I   T   C   K   A   S   Q   D   I   N
                             *   *                       1
                                                         Q __  CDR1 - IMGT  _____  <---------------------------
                                             35                  40                  45
humanized 6F4 VL domain  N   Y                           I   A   W   Y   Q   Q   K
                                                         2   1               *
                                                         N FR2 - IMGT  ------------------------>  _____   CDR2
                                             50                  55                  60
humanized 6F4 VL domain  P   G   K   A   P   K   L   L   I   H   Y   T   S
                                     *       *               2

- IMGT  _____  <-----------------------------------
                                             65                  70                  75
humanized 6F4 VL domain                          T   L   Q   A   G   V   P       S   R
                                                 2       1   1       *
                                                 E       T ---------------------------  FR3 - IMGT  ----------------
                                             80                  85                  90
humanized 6F4 VL domain  F   S   G   S           S   G   R   D   Y   T   F   T
                                                         1       1   *       *
                                                         T       F ------------------------------------------------>  _____
                                             95                 100                 104
humanized 6F4 VL domain  I   S   S   L   Q   P   E   D   I   A   T   Y   Y   C   L
                                     *       *                   *

_____  CDR3 - IMGT  _____  <-------------- FR4 - IMGT  ----
                                            110                 115                 120
humanized 6F4 VL domain  Q   Y   D   N   L   W   T   F   G   Q   G   T   K   V   E
                                                             *               *

------>
                                            122
humanized 6F4 VL domain  I   K
```

FIGURE 17

```
                           <----------------------------------- FR1 - IMGT
                           1           5              10                  15
humanized 6F4 VH domain    E   I   Q   L   V   Q   S   G   A   E   V   K   K   P
                               1           *           *       *   *
                               V ---------------------------------------> _____
                                              20              25                  30
humanized 6F4 VH domain    G   A   T   V   K   I   S   C   K   V   S   G   Y   S   F
                                       *           *           *

___ CDR1 - IMGT _____ <---------------------------
                                              35              40                  45
humanized 6F4 VH domain    T   D   Y   S                   M   Y   W   V   Q   Q   A
                                                               1           *       *
                                                               H FR2 - IMGT -------------------------> _____ CDR2
                                              50              55                  60
humanized 6F4 VH domain    P   G   K   G   L   E   W   I   G   Y   I   D   P   Y   N
                           *           *                   1       2
                                                           M

- IMGT _____ <-----------------------------------
                                              65              70                  75
humanized 6F4 VH domain    G   G   T           R   Y   N   Q   K   F   K       G   R
                                               ?       1   1       1               *
                                               A       E           Q ----------------------------- FR3 - IMGT ---------------
                                              80              85                  90
humanized 6F4 VH domain    V   T   I   T   A   D   K   S   T   D   T   A   Y   M   E
                           *       *       *       1       *   *       *       *
                                                   T ---------------------------------------------------> ____
                                              95              100                 105
humanized 6F4 VH domain    L   S   S   L   R   S   E   D   T   A   V   Y   Y   C   A
                               *           *           *

_____ CDR3 - IMGT _____ <-------------- FR4 - IMGT
                                              110             115                 120
humanized 6F4 VH domain    R   Q   T   D   Y   F   D   Y   W   G   Q   G   T   L   V
                               *   *

--------------->
                                              124
humanized 6F4 VH domain    T   V   S   S
```

FIGURE 18

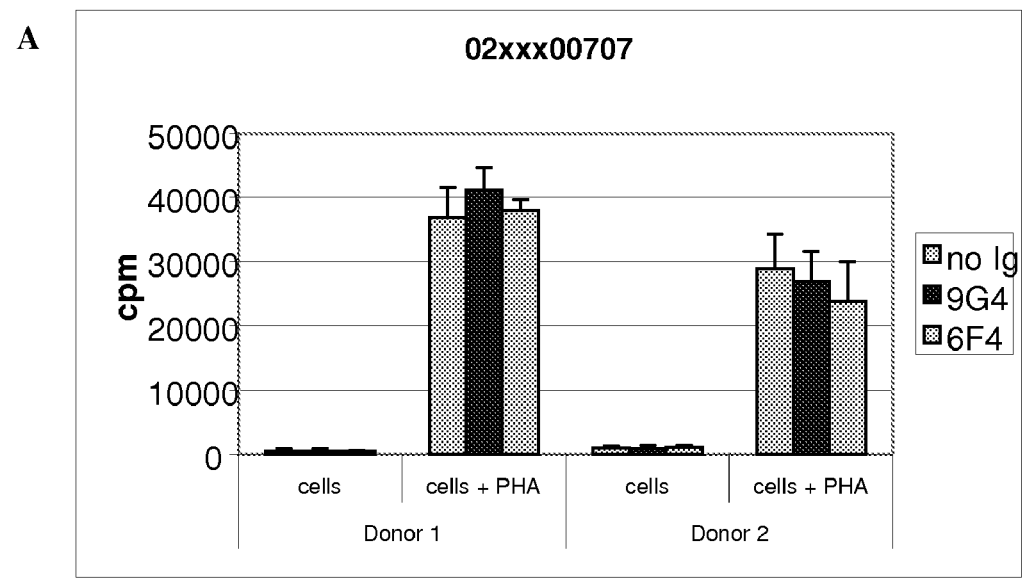
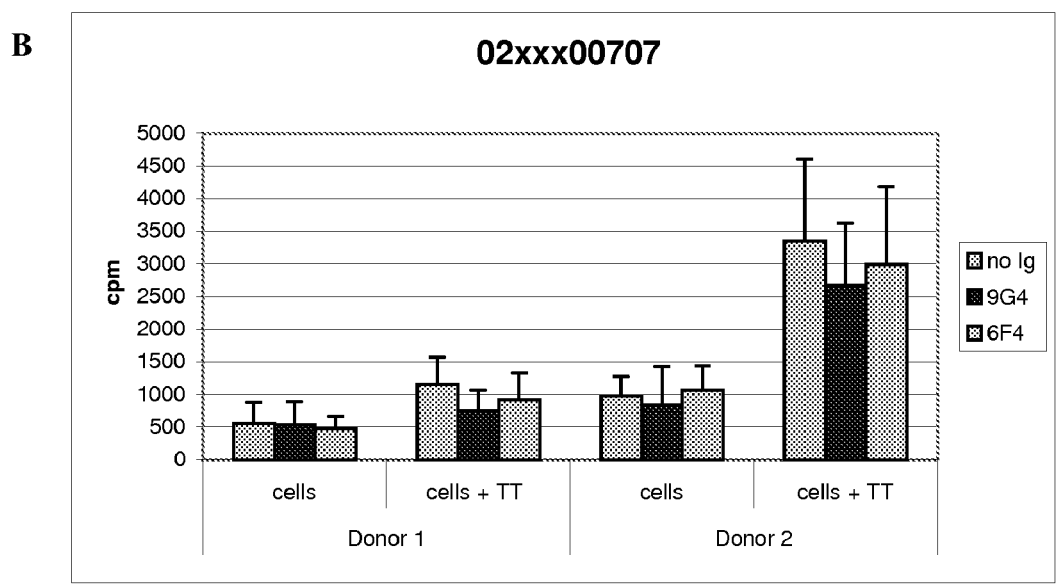
FIGURE 27

A
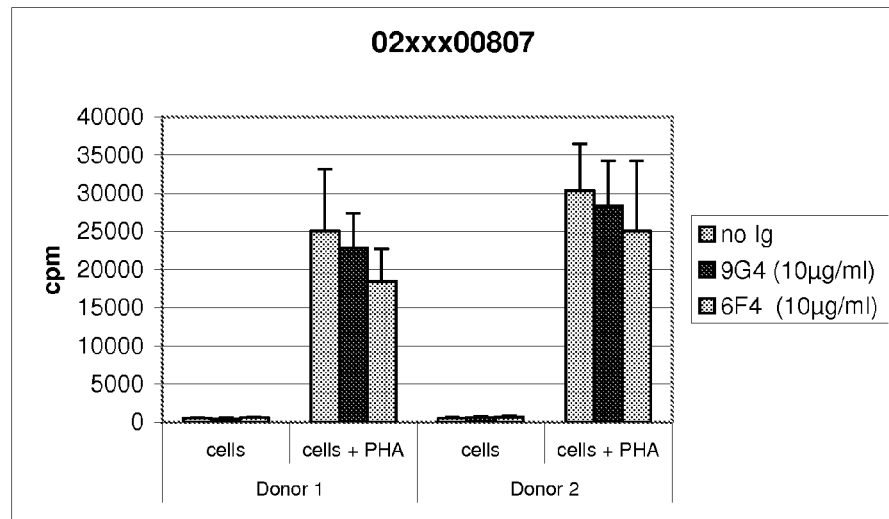
B
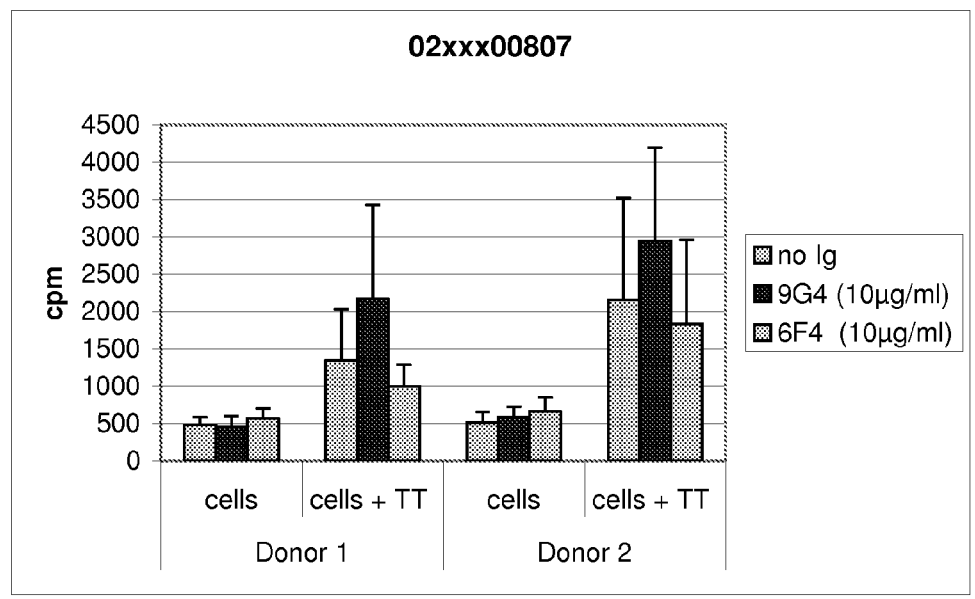
FIGURE 28

```
                                <------------------------------------------- FR1 - IMGT
                                1           5                   10                  15
6F4 VH domain                   E   I   Q   L   Q   Q   S   G   P       E   L   V   K   P
X62109 IGHV1-3*01               Q   V           V                   A           V   K
HZ2 VH domain                   Q   V   Q   L   V   Q   S   G       A       E   V   K   K   P
                                1           3                   3               4   3

--------------------------------------->   _____
                                            20                  25                  30
6F4 VH domain                   G   A   S   V   K   V   S   C   K   A   S   G   Y   S   F
X62109 IGHV1-3*01
HZ2 VH domain                   G   A   S   V   K   V   S   C   K   A   S   G   Y   S   F ___ CDR1 - IMGT _____   <-------------------------
                                            35                  40                  45
6F4 VH domain                   T   D   Y   S                   M   Y   W   V   K   Q   S
X62109 IGHV1-3*01                                               H           R       A
HZ2 VH domain                   T   D   Y   S                   M   H   W   V   R   Q   A
                                                                                1       3

FR2 - IMGT ----------------------->   _____   CDR2
                                            50                  55                  60
6F4 VH domain                   H   G   K   S   L   E   W   I   G   Y   I   D   P   Y   N
X62109 IGHV1-3*01               P       Q   R               M       W
HZ2 VH domain                   P   G   Q   R   L   E   W   M   G   Y   I   D   P   Y   N
                                3       2   2

- IMGT _____   <-------------------------------
                                            65                  70                  75
6F4 VH domain                   G   G   T           R   Y   N   Q   K   F   K       G   K
X62109 IGHV1-3*01                                   K       S                   Q       R
HZ2 VH domain                   G   G   T           R   Y   S   Q   K   F   Q       G   R
                                                                                        1

------------------------------ FR3 - IMGT ---------------
                                            80                  85                  90
6F4 VH domain                   A   T   L   T   V   D   K   S   S   S   T   A   F   M   H
X62109 IGHV1-3*01               V       I           R       T       A           Y       E
HZ2 VH domain                   V   T   I   T   A   D   T   S   T   S   T   A   Y   M   E
                                4       4                                       2       2

--------------------------------------------------->   CDR
                                            95                  100                 105
6F4 VH domain                   L   N   S   L   T   S   E   D   S   A   V   Y   Y   C   A
X62109 IGHV1-3*01                   S           R               T
HZ2 VH domain                   L   S   S   L   R   S   E   D   T   A   V   Y   Y   C   A
                                    3           3               4
```

FIGURE 31

```
              FR1-IMGT              CDR1-IMGT         FR2-IMGT           CDR2-IMGT
              (1-26)                (27-38)           (39-55)            (56-65)

1        10        20          30          40        50         60
              |.........|.........|......   ...|.........  .|.........|.....  ....|.....
6F4 VL        DIQMTQSPSSLSASLGGKVTITCKAS     QDI      NNY   IAWYQHKPGKGPRLLIH  YT    S
                          3 23    1                        1    2  3 3    1
Human FR      --------------V-DR-----R--                   L----Q----V-K---Y
6F4 BU-L1     DIQMTQSPSSLSASVGDRVTITCKAS     QDI      NNY   IAWYQQKPGKVPKLLIH  YT    S FR3-IMGT                    CDR3-IMGT      FR4-IMGT
                            (66-104)                    (105-112)      (113-122)

70        80        90       100         110            122
              ....|.........|.........|.........|....   .....|....    .........|
6F4 VL        TLQAGIP  SRFSGSG    SGRDYSFSISNLEPEDIGTYYC   LQYDNLWT    FGGGTKLEIK
                 2 3                2 1323 2 3    3                     2    3
Human FR      ---S-V-  -------    --T-FTLT--S-Q---V-----                --Q---V---
6F4 BU-L1     TLQSGVP  SRFSGSG    SGTDYTLTISSLQPEDVGTYYC   LQYDNLWT    FGQGTKVEIK
```

FIGURE 32

```
              FR1-IMGT              CDR1-IMGT         FR2-IMGT           CDR2-IMGT
              (1-26)                (27-38)           (39-55)            (56-65)

1        10        20          30          40        50         60
              |.........|.........|......   ...|.........  .|.........|.....  ....|.....
6F4 VL        DIQMTQSPSSLSASLGGKVTITCKAS     QDI      NNY   IAWYQHKPGKGPRLLIH  YT    S
              1 1       2      3 23    1                   1    2  3 3 3 2 1
Human FR      A-R-----F-----V-DR-----W--                   L----Q--A-A-K-F-Y
6F4 BU-L2     DIQMTQSPFSLSASVGDRVTITCKAS     QDI      NNY   IAWYQQKPAKAPKLFIH  YT    S FR3-IMGT                    CDR3-IMGT      FR4-IMGT
                            (66-104)                    (105-112)      (113-122)

70        80        90       100         110            122
              ....|.........|.........|.........|....   .....|....    .........|
6F4 VL        TLQAGIP  SRFSGSG    SGRDYSFSISNLEPEDIGTYYC   LQYDNLWT    FGGGTKLEIK
              1  2 3                2  323 2 3    33                    2    3
Human FR      S--S-V-  -------    --T--TLT--S-Q---FA----                --Q---V---
6F4 BU-L2     TLQSGVP  SRFSGSG    SGTDYTLTISSLQPEDFATYYC   LQYDNLWT    FGGGTKLEIK
```

FIGURE 33

```
                    FR1-IMGT              CDR1-IMGT        FR2-IMGT              CDR2-IMGT
                     (1-26)                (27-38)          (39-55)               (56-65)

1         10        20              30             40        50             60
            |.........|.........|........    ...|........   .|.........|.....      ....|.....
6F4 VH      EIQLQQSGP.ELVKPGASVKVSCKAS       GYSF....TDYS   MYWVKQSHGKSLEWIGY      IDPY..NGGT
            12  1   2 33                                     2  3 32 31      2 1
Human FR    QV--V---A.-VK-------------                      -H--R-AP-QR---M-W
6F4 BU-H1   EVQLVQSGA.EVKKPGASVKVSCKAS       GYSF....TDYS   MHWVRQAPGQSLEWMGY      IDPY..NGGT FR3-IMGT                      CDR3-IMGT    FR4-IMGT
                              (66-104)                      (105-113)    (114-   )

70        80        90       100              110              124
            ....|.........|.........|.........|....         ....|....    .........|
6F4 VH      RYNQKFK.GKATLTVDKSSSTAFMHLNSLTSEDSAVYYC          ARQTDYFDY    WGQGTTLTVSS
            1 3    3  31 1 1 3 2    3 1 3  3    3                                 33
Human FR    K-S---Q.-RV-I-R-T-A---Y-E-S--R---T-----                      -----LV----
6F4 BU-H1   RYSQKFQ.GRATLTVDTSASTAYMHLSSLRSEDTAVYYC          ARQTDYFDY    WGQGTLVTVSS
```

FIGURE 34

```
                    FR1-IMGT              CDR1-IMGT        FR2-IMGT              CDR2-IMGT
                     (1-26)                (27-38)          (39-55)               (56-65)

1         10        20              30             40        50             60
            |.........|.........|........    ...|........   .|.........|.....      ....|.....
6F4 VH      EIQLQQSGP.ELVKPGASVKVSCKAS       GYSF....TDYS   MYWVKQSHGKSLEWIGY      IDPY..NGGT
            12  1   2 33                                     2  3 32 31      2 1
Human FR    QV--V---A.-VK-------------                      -H--R-AP-QG---M-I
6F4 BU-H2   EVQLVQSGA.EVKKPGASVKVSCKAS       GYSF....TDYS   MHWVRQAPGQSLEWMGY      IDPY..NGGT FR3-IMGT                      CDR3-IMGT    FR4-IMGT
                              (66-104)                      (105-113)    (114-   )

70        80        90       100              110              124
            ....|.........|.........|.........|....         ....|....    .........|
6F4 VH      RYNQKFK.GKATLTVDKSSSTAFMHLNSLTSEDSAVYYC          ARQTDYFDY    WGQGTTLTVSS
            1 3    3  31 1 1 3 2    33 1 3  3    3                                33
Human FR    S-A---Q.-RV-M-R-T-T---VY-E-S--R---T-----                     -----LV----
6F4 BU-H2   RYSQKFQ.GRATLTVDTSASTAYMHLSSLRSEDTAVYYC          ARQTDYFDY    WGQGTLVTVSS
```

FIGURE 35

SEQUENCE LISTING

<160> NUMBER OF SEQ ID NOS: 104

<210> SEQ ID NO 1
<211> LENGTH: 6
<212> TYPE: PRT
<213> ORGANISM: Mus musculus

<400> SEQUENCE: 1

Gln Asp Ile Asn Asn Tyr
1               5

<210> SEQ ID NO 2
<211> LENGTH: 4
<212> TYPE: PRT
<213> ORGANISM: Mus musculus

<400> SEQUENCE: 2

Thr Asp Tyr Ser
1

<210> SEQ ID NO 3
<211> LENGTH: 3
<212> TYPE: PRT
<213> ORGANISM: Mus musculus

<400> SEQUENCE: 3

Tyr Thr Ser
1

<210> SEQ ID NO 4
<211> LENGTH: 8
<212> TYPE: PRT
<213> ORGANISM: Mus musculus

<400> SEQUENCE: 4

Ile Asp Pro Tyr Asn Gly Gly Thr
1               5

<210> SEQ ID NO 5
<211> LENGTH: 8
<212> TYPE: PRT
<213> ORGANISM: Mus musculus

<400> SEQUENCE: 5

Leu Gln Tyr Asp Asn Leu Trp Thr
1               5

<210> SEQ ID NO 6
<211> LENGTH: 7
<212> TYPE: PRT
<213> ORGANISM: Mus musculus

<400> SEQUENCE: 6

Gln Thr Asp Tyr Phe Asp Tyr
1               5

<210> SEQ ID NO 7
<211> LENGTH: 8
<212> TYPE: PRT
<213> ORGANISM: Mus musculus

<400> SEQUENCE: 7

Gly Tyr Ser Phe Thr Asp Tyr Ser
1               5

<210> SEQ ID NO 8
<211> LENGTH: 11
<212> TYPE: PRT
<213> ORGANISM: Mus musculus

<400> SEQUENCE: 8

Lys Ala Ser Gln Asp Ile Asn Asn Tyr Ile Ala
1               5                   10

<210> SEQ ID NO 9
<211> LENGTH: 6
<212> TYPE: PRT
<213> ORGANISM: Mus musculus

<400> SEQUENCE: 9

Thr Asp Tyr Ser Met Tyr
1               5

<210> SEQ ID NO 10
<211> LENGTH: 7
<212> TYPE: PRT
<213> ORGANISM: Mus musculus

<400> SEQUENCE: 10

Tyr Thr Ser Thr Leu Gln Ala
1               5

<210> SEQ ID NO 11
<211> LENGTH: 17
<212> TYPE: PRT
<213> ORGANISM: Mus musculus

<400> SEQUENCE: 11

Tyr Ile Asp Pro Tyr Asn Gly Gly Thr Arg Tyr Asn Gln Lys Phe Lys
1               5                   10                  15

Gly

<210> SEQ ID NO 12
<211> LENGTH: 9
<212> TYPE: PRT
<213> ORGANISM: Mus musculus

<400> SEQUENCE: 12

Ala Arg Gln Thr Asp Tyr Phe Asp Tyr
1               5

<210> SEQ ID NO 13
<211> LENGTH: 106
<212> TYPE: PRT
<213> ORGANISM: Mus musculus

<400> SEQUENCE: 13

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Asn Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Ala Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

```
Glu Asp Ile Gly Thr Tyr Tyr Cys Leu Gln Tyr Asp Asn Leu Trp Thr
                85                  90                  95

Phe Gly Gly Gly Thr Lys Leu Glu Ile Lys
            100                 105

<210> SEQ ID NO 14
<211> LENGTH: 116
<212> TYPE: PRT
<213> ORGANISM: Mus musculus

<400> SEQUENCE: 14

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Tyr
            20                  25                  30

Ser Met Tyr Trp Val Lys Gln Ser His Gly Lys Ser Leu Glu Trp Ile
        35                  40                  45

Gly Tyr Ile Asp Pro Tyr Asn Gly Gly Thr Arg Tyr Asn Gln Lys Phe
    50                  55                  60

Lys Gly Lys Ala Thr Leu Thr Val Asp Lys Ser Ser Ser Thr Ala Phe
65                  70                  75                  80

Met His Leu Asn Ser Leu Thr Ser Glu Asp Ser Ala Val Tyr Tyr Cys
                85                  90                  95

Ala Arg Gln Thr Asp Tyr Phe Asp Tyr Trp Gly Gln Gly Thr Thr Leu
            100                 105                 110

Thr Val Ser Ser
        115

<210> SEQ ID NO 15
<211> LENGTH: 215
<212> TYPE: PRT
<213> ORGANISM: Mus musculus

<400> SEQUENCE: 15

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Asn Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Ala Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Gly Thr Tyr Tyr Cys Leu Gln Tyr Asp Asn Leu Trp Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175
```

```
Thr Leu Thr Leu Thr Lys Asp Glu Tyr Glu Arg His Asn Ser Tyr Thr
            180                 185                 190
Cys Glu Ala Thr His Lys Thr Ser Thr Ser Pro Ile Val Lys Ser Phe
            195                 200                 205
Asn Arg Asn Glu Cys Asn His
            210             215

<210> SEQ ID NO 16
<211> LENGTH: 440
<212> TYPE: PRT
<213> ORGANISM: Mus musculus

<400> SEQUENCE: 16

Glu Ile Gln Leu Gln Gln Ser Gly Pro Glu Leu Val Lys Pro Gly Ala
1               5                   10                  15
Ser Val Lys Val Ser Cys Lys Ala Ser Gly Tyr Ser Phe Thr Asp Tyr
            20                  25                  30
Ser Met Tyr Trp Val Lys Gln Ser His Gly Lys Ser Leu Glu Trp Ile
        35                  40                  45
Gly Tyr Ile Asp Pro Tyr Asn Gly Gly Thr Arg Tyr Asn Gln Lys Phe
    50                  55                  60
Lys Gly Lys Ala Thr Leu Thr Val Asp Lys Ser Ser Ser Thr Ala Phe
65                  70                  75                  80
Met His Leu Asn Ser Leu Thr Ser Glu Asp Ser Ala Val Tyr Tyr Cys
                85                  90                  95
Ala Arg Gln Thr Asp Tyr Phe Asp Tyr Trp Gly Gln Gly Thr Thr Leu
            100                 105                 110
Thr Val Ser Ser Ala Lys Thr Thr Pro Pro Ser Val Tyr Pro Leu Ala
        115                 120                 125
Pro Gly Ser Ala Ala Gln Thr Asn Ser Met Val Thr Leu Gly Cys Leu
    130                 135                 140
Val Lys Gly Tyr Phe Pro Glu Pro Val Thr Val Thr Trp Asn Ser Gly
145                 150                 155                 160
Ser Leu Ser Ser Gly Val His Thr Phe Pro Ala Val Leu Gln Ser Asp
                165                 170                 175
Leu Tyr Thr Leu Ser Ser Ser Val Thr Val Pro Ser Ser Thr Trp Pro
            180                 185                 190
Ser Glu Thr Val Thr Cys Asn Val Ala His Pro Ala Ser Ser Thr Lys
        195                 200                 205
Val Asp Lys Lys Ile Val Pro Arg Asp Cys Gly Cys Lys Pro Cys Ile
    210                 215                 220
Cys Thr Val Pro Glu Val Ser Ser Val Phe Ile Phe Pro Pro Lys Pro
225                 230                 235                 240
Lys Asp Val Leu Thr Ile Thr Leu Thr Pro Lys Val Thr Cys Val Val
                245                 250                 255
Val Asp Ile Ser Lys Asp Asp Pro Glu Val Gln Phe Ser Trp Phe Val
            260                 265                 270
Asp Asp Val Glu Val His Thr Ala Gln Thr Gln Pro Arg Glu Glu Gln
        275                 280                 285
Phe Asn Ser Thr Phe Arg Ser Val Ser Glu Leu Pro Ile Met His Gln
    290                 295                 300
Asp Trp Leu Asn Gly Lys Glu Phe Lys Cys Arg Val Asn Ser Ala Ala
305                 310                 315                 320
Phe Pro Ala Pro Ile Glu Lys Thr Ile Ser Lys Thr Lys Gly Arg Pro
                325                 330                 335
```

```
Lys Ala Pro Gln Val Tyr Thr Ile Pro Pro Lys Glu Gln Met Ala
                340                 345                 350
Lys Asp Lys Val Ser Leu Thr Cys Met Ile Thr Asp Phe Phe Pro Glu
            355                 360                 365
Asp Ile Thr Val Glu Trp Gln Trp Asn Gly Gln Pro Ala Glu Asn Tyr
        370                 375                 380
Lys Asn Thr Gln Pro Ile Met Asp Thr Asp Gly Ser Tyr Phe Val Tyr
385                 390                 395                 400
Ser Lys Leu Asn Val Gln Lys Ser Asn Trp Glu Ala Gly Asn Thr Phe
                405                 410                 415
Thr Cys Ser Val Leu His Glu Gly Leu His Asn His His Thr Glu Lys
            420                 425                 430
Ser Leu Ser His Ser Pro Gly Lys
            435                 440

<210> SEQ ID NO 17
<211> LENGTH: 106
<212> TYPE: PRT
<213> ORGANISM: Mus musculus

<400> SEQUENCE: 17

Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Asp Ile Asn Asn Tyr
            20                  25                  30
Ile Ala Trp Tyr Gln Gln Lys Pro Gly Lys Ala Pro Lys Leu Leu Ile
        35                  40                  45
His Tyr Thr Ser Thr Leu Glu Thr Gly Val Pro Ser Arg Phe Ser Gly
    50                  55                  60
Ser Gly Ser Gly Thr Asp Tyr Thr Phe Thr Ile Ser Ser Leu Gln Pro
65                  70                  75                  80
Glu Asp Ile Ala Thr Tyr Tyr Cys Leu Gln Tyr Asp Asn Leu Trp Thr
                85                  90                  95
Phe Gly Gln Gly Thr Lys Val Glu Ile Lys
            100                 105

<210> SEQ ID NO 18
<211> LENGTH: 116
<212> TYPE: PRT
<213> ORGANISM: Mus musculus

<400> SEQUENCE: 18

Glu Val Gln Leu Val Gln Ser Gly Ala Glu Val Lys Lys Pro Gly Ala
1               5                   10                  15
Thr Val Lys Ile Ser Cys Lys Val Ser Gly Tyr Ser Phe Thr Asp Tyr
            20                  25                  30
Ser Met His Trp Val Gln Gln Ala Pro Gly Lys Gly Leu Glu Trp Met
        35                  40                  45
Gly Tyr Ile Asp Pro Tyr Asn Gly Gly Thr Arg Tyr Ala Glu Lys Phe
    50                  55                  60
Gln Gly Arg Val Thr Ile Thr Ala Asp Thr Ser Thr Asp Thr Ala Tyr
65                  70                  75                  80
Met Glu Leu Ser Ser Leu Arg Ser Glu Asp Thr Ala Val Tyr Tyr Cys
                85                  90                  95
Ala Arg Gln Thr Asp Tyr Phe Asp Tyr Trp Gly Gln Gly Thr Leu Val
            100                 105                 110
Thr Val Ser Ser
```

<210> SEQ ID NO 19
<211> LENGTH: 116
<212> TYPE: PRT
<213> ORGANISM: Mus musculus

<400> SEQUENCE: 19

```
Gln Val Gln Leu Val Gln Ser Gly Ala Glu Val Lys Lys Pro Gly Ala
  1               5                  10                  15
Ser Val Lys Val Ser Cys Lys Ala Ser Gly Tyr Ser Phe Thr Asp Tyr
                 20                  25                  30
Ser Met His Trp Val Arg Gln Ala Pro Gly Gln Arg Leu Glu Trp Met
             35                  40                  45
Gly Tyr Ile Asp Pro Tyr Asn Gly Gly Thr Arg Tyr Ser Gln Lys Phe
     50                  55                  60
Gln Gly Arg Val Thr Ile Thr Ala Asp Thr Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Gln Thr Asp Tyr Phe Asp Tyr Trp Gly Gln Gly Thr Leu Val
                100                 105                 110
Thr Val Ser Ser
            115
```

<210> SEQ ID NO 20
<211> LENGTH: 18
<212> TYPE: DNA
<213> ORGANISM: Mus musculus

<400> SEQUENCE: 20
caagacatta acaattat                                                      18

<210> SEQ ID NO 21
<211> LENGTH: 12
<212> TYPE: DNA
<213> ORGANISM: Mus musculus

<400> SEQUENCE: 21
actgactaca gc                                                            12

<210> SEQ ID NO 22
<211> LENGTH: 9
<212> TYPE: DNA
<213> ORGANISM: Mus musculus

<400> SEQUENCE: 22 tacacatct                                                                 9

<210> SEQ ID NO 23
<211> LENGTH: 24
<212> TYPE: DNA
<213> ORGANISM: Mus musculus

<400> SEQUENCE: 23
attgatcctt acaatggtgg tact                                               24

<210> SEQ ID NO 24
<211> LENGTH: 24
<212> TYPE: DNA
<213> ORGANISM: Mus musculus

```
<400> SEQUENCE: 24
ctacagtatg ataatctgtg gacg                                          24

<210> SEQ ID NO 25
<211> LENGTH: 21
<212> TYPE: DNA
<213> ORGANISM: Mus musculus

<400> SEQUENCE: 25
cagacggact actttgacta c                                             21

<210> SEQ ID NO 26
<211> LENGTH: 24
<212> TYPE: DNA
<213> ORGANISM: Mus musculus

<400> SEQUENCE: 26
ggttactcat tcactgacta cagc                                          24

<210> SEQ ID NO 27
<211> LENGTH: 27
<212> TYPE: DNA
<213> ORGANISM: Mus musculus

<400> SEQUENCE: 27
gcaagacaga cggactactt tgactac                                       27

<210> SEQ ID NO 28
<211> LENGTH: 33
<212> TYPE: DNA
<213> ORGANISM: Mus musculus

<400> SEQUENCE: 28
aaggcaagcc aagacattaa caattatata gct                                33

<210> SEQ ID NO 29
<211> LENGTH: 21
<212> TYPE: DNA
<213> ORGANISM: Mus musculus

<400> SEQUENCE: 29
tacacatcta cattacaagc a                                             21

<210> SEQ ID NO 30
<211> LENGTH: 18
<212> TYPE: DNA
<213> ORGANISM: Mus musculus

<400> SEQUENCE: 30
actgactaca gcatgtac                                                 18

<210> SEQ ID NO 31
<211> LENGTH: 51
<212> TYPE: DNA
<213> ORGANISM: Mus musculus

<400> SEQUENCE: 31
tatattgatc cttacaatgg tggtactagg tacaaccaga agttcaaggg c             51

<210> SEQ ID NO 32
<211> LENGTH: 318
<212> TYPE: DNA
<213> ORGANISM: Mus musculus
```

```
<400> SEQUENCE: 32
gacatccaga tgacacagtc tccatcctca ctgtctgcat ctctgggagg caaagtcacc      60
atcacttgca aggcaagcca agacattaac aattatatag cttggtacca acacaagcct    120
ggaaaaggtc ctaggctgct catacattac acatctacat tacaagcagg catcccatca    180
aggttcagtg gaagtgggtc tgggagagat tattccttca gcatcagcaa cctggagcct    240
gaagatattg aacttatta ttgtctacag tatgataatc tgtggacgtt cggtggaggc     300
accaagctgg aaatcaaa                                                  318

<210> SEQ ID NO 33
<211> LENGTH: 348
<212> TYPE: DNA
<213> ORGANISM: Mus musculus

<400> SEQUENCE: 33
gagatccagc tgcagcagtc tggacctgag ctggtgaagc ctggggcttc agtgaaggta      60
tcctgcaagg cttctggtta ctcattcact gactacagca tgtactgggt gaagcagagc    120
catggaaaga gccttgagtg gattggatat attgatcctt acaatggtgg tactaggtac    180
aaccagaagt tcaagggcaa ggccacattg actgttgaca agtcctccag cacagccttc    240
atgcatctca acagcctgac atctgaggac tctgcagtct attactgtgc aagacagacg    300
gactactttg actactgggg ccaaggcacc actctcacag tctcctca                 348

<210> SEQ ID NO 34
<211> LENGTH: 639
<212> TYPE: DNA
<213> ORGANISM: Mus musculus

<400> SEQUENCE: 34
gacatccaga tgacacagtc tccatcctca ctgtctgcat ctctgggagg caaagtcacc      60
atcacttgca aggcaagcca agacattaac aattatatag cttggtacca acacaagcct    120
ggaaaaggtc ctaggctgct catacattac acatctacat tacaagcagg catcccatca    180
aggttcagtg gaagtgggtc tgggagagat tattccttca gcatcagcaa cctggagcct    240
gaagatattg aacttatta ttgtctacag tatgataatc tgtggacgtt cggtggaggc     300
accaagctgg aaatcaaacg ggctgatgct gcaccaactg tatccatctt cccaccatcc    360
agtgagcagt taacatctgg aggtgcctca gtcgtgtgct tcttgaacaa cttctacccc    420
aaagacatca atgtcaagtg gaagattgat ggcagtgaac gacaaaatgg cgtcctgaac    480
agttggactg atcaggacag caaagacagc acctacagca tgagcagcac cctcacgttg    540
accaaggacg agtatgaacg acataacagc tataccctgt aggccactca aagacatca    600 acttcaccca ttgtcaagag cttcaacagg aatgagtgt                           639

<210> SEQ ID NO 35
<211> LENGTH: 1320
<212> TYPE: DNA
<213> ORGANISM: Mus musculus

<400> SEQUENCE: 35
gagatccagc tgcagcagtc tggacctgag ctggtgaagc ctggggcttc agtgaaggta      60
tcctgcaagg cttctggtta ctcattcact gactacagca tgtactgggt gaagcagagc    120
catggaaaga gccttgagtg gattggatat attgatcctt acaatggtgg tactaggtac    180
aaccagaagt tcaagggcaa ggccacattg actgttgaca agtcctccag cacagccttc    240
```

```
atgcatctca acagcctgac atctgaggac tctgcagtct attactgtgc aagacagacg    300
gactactttg actactgggg ccaaggcacc actctcacag tctcctcagc caaaacaaca    360
gccccatcgg tctatccact ggcccctgga tctgctgccc aaactaactc catggtgacc    420
ctgggatgcc tggtcaaggg ctatttccct gagccagtga cagtgacctg gaactctgga    480
tccctgtcca gcggtgtgca caccttccca gctgtcctgc agtctgacct ctacactctg    540
agcagctcag tgactgtccc ctccagcacc tggcccagcg agaccgtcac ctgcaacgtt    600
gcccacccgg ccagcagcac caaggtggac aagaaaattg tgcccaggga ttgtggttgt    660
aagccttgca tatgtacagt cccagaagta tcatctgtct tcatcttccc cccaaagccc    720
aaggatgtgc tcaccattac tctgactcct aaggtcacgt gtgttgtggt agacatcagc    780
aaggatgatc ccgaggtcca gttcagctgg tttgtagatg atgtggaggt gcacacagct    840
cagacgcaac cccgggagga gcagttcaac agcactttcc gctcagtcag tgaacttccc    900
atcatgcacc aggactggct caatggcaag gagttcaaat gcagggtcaa cagtgcagct    960
ttccctgccc ccatcgagaa aaccatctcc aaaaccaaag cagaccgaa ggctccacag    1020 gtgtacacca ttccacctcc caaggagcag atggccaagg ataaagtcag tctgacctgc    1080
atgataacag acttcttccc tgaagacatt actgtggagt ggcagtggaa tgggcagcca    1140
gcggagaact acaagaacac tcagcccatc atggacacag atggctctta cttcgtctac    1200
agcaagctca atgtgcagaa gagcaactgg gaggcaggaa atactttcac ctgctctgtg    1260
ttacatgagg gcctgcacaa ccaccatact gagaagagcc tctcccactc tcctggtaaa    1320

<210> SEQ ID NO 36
<211> LENGTH: 318
<212> TYPE: DNA
<213> ORGANISM: Mus musculus

<400> SEQUENCE: 36
gacatacaga tgactcagag cccatcatca ttgagcgcgt ctgtcggcga tcgggttacc     60
attacctgcc aggcaagtca agatatcaac aactatattg cttggtatca acagaagccc    120
ggtaaagccc caaagctgct gatacactac acctccaccc tggagaccgg cgtgccttct    180
agattttctg gaagcgggtc cggaaccgat tatacgttca caatctccag ccttcagccc    240
gaagacatcg ccacatacta ctgtctgcaa tacgacaatc tgtggacatt tggccagggg    300
actaaggtgg agatcaaa                                                  318

<210> SEQ ID NO 37
<211> LENGTH: 345
<212> TYPE: DNA
<213> ORGANISM: Mus musculus

<400> SEQUENCE: 37
gaagtgcagc tggttcagag cggcgccgag gtaaaaccag ggcgacggt gaagataagc      60 tgcaaggtga gtgggtactc attcaccgac tattcaatgc actgggtcca acaggcccct    120
ggtaaaggac tggagtggat gggatacatc gatccctaca tggaggcac taggtacgcc    180 gagaagttcc aggggagagt cactattacc gcagatactt ctaccgatac tgcctacatg    240
gaactcagca gtctgcggtc cgaggacaca gcagtctact attgtgctcg ccaaacagac    300
tattttgact attggggcca gggaaccttg gtgacagtgt cctct                    345

<210> SEQ ID NO 38
<211> LENGTH: 348
<212> TYPE: DNA
```

-continued

```
<213> ORGANISM: Mus musculus

<400> SEQUENCE: 38
caggtgcaat tggtacagtc aggcgcggag gtgaagaagc ctggggctag tgttaaagtc      60
tcctgtaaag cctccggata ttccttcact gactactcta tgcattgggt tcgccaggca     120
ccagggcagc ggctggaatg gatggggtac attgatccct acaacggagg cacgcgatat     180
agtcagaagt tccagggtcg ggtgacaatc acagccgata cgtccaccag caccgcctac     240
atggagttga gcagtctcag gtcagaagac acagccgtgt actattgcgc aagacagacc     300
gattatttcg actactgggg ccaaggcact ctcgtgaccg tctctagc                  348

<210> SEQ ID NO 39
<211> LENGTH: 115
<212> TYPE: PRT
<213> ORGANISM: Mus musculus

<400> SEQUENCE: 39

Met Arg Pro Ser Ile Gln Phe Leu Gly Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ala Ser Gln Asp
        35                  40                  45

Ile Asn Lys Tyr Ile Ala Trp Tyr Gln His Lys Pro Gly Lys Gly Pro
    50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Asn Leu Leu
        115

<210> SEQ ID NO 40
<211> LENGTH: 12
<212> TYPE: PRT
<213> ORGANISM: Mus musculus

<400> SEQUENCE: 40

Trp Thr Phe Gly Gly Gly Thr Lys Leu Glu Ile Lys
1               5                   10

<210> SEQ ID NO 41
<211> LENGTH: 117
<212> TYPE: PRT
<213> ORGANISM: Homo sapiens

<400> SEQUENCE: 41

Met Asp Met Arg Val Pro Ala Gln Leu Leu Gly Leu Leu Gln Leu Trp
1               5                   10                  15

Leu Ser Gly Ala Arg Cys Asp Ile Gln Met Thr Gln Ser Pro Ser Ser
            20                  25                  30

Leu Ser Ala Ser Val Gly Asp Arg Val Thr Ile Thr Cys Gln Ala Ser
        35                  40                  45

Gln Asp Ile Ser Asn Tyr Leu Asn Trp Tyr Gln Gln Lys Pro Gly Lys
    50                  55                  60

Ala Pro Lys Leu Leu Ile Tyr Asp Ala Ser Asn Leu Glu Thr Gly Val
```

```
                    65                  70                  75                  80
Pro Ser Arg Phe Ser Gly Ser Gly Ser Gly Thr Asp Phe Thr Phe Thr
                        85                  90                  95

Ile Ser Ser Leu Gln Pro Glu Asp Ile Ala Thr Tyr Tyr Cys Gln Gln
                100                 105                 110

Tyr Asp Asn Leu Pro
                115

<210> SEQ ID NO 42
<211> LENGTH: 12
<212> TYPE: PRT
<213> ORGANISM: Homo sapiens

<400> SEQUENCE: 42

Trp Thr Phe Gly Gln Gly Thr Lys Val Glu Ile Lys
1               5                   10

<210> SEQ ID NO 43
<211> LENGTH: 98
<212> TYPE: PRT
<213> ORGANISM: Mus musculus

<400> SEQUENCE: 43

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Tyr
                20                  25                  30

Asn Met Tyr Trp Val Lys Gln Ser His Gly Lys Ser Leu Glu Trp Ile
            35                  40                  45

Gly Tyr Ile Asp Pro Tyr Asn Gly Gly Thr Ser Tyr Asn Gln Lys Phe
        50                  55                  60

Lys Gly Lys Ala Thr Leu Thr Val Asp Lys Ser Ser Ser Thr Ala Phe
65                  70                  75                  80

Met His Leu Asn Ser Leu Thr Ser Glu Asp Ser Ala Val Tyr Tyr Cys
                85                  90                  95

Ala Arg

<210> SEQ ID NO 44
<211> LENGTH: 2
<212> TYPE: PRT
<213> ORGANISM: Mus musculus

<400> SEQUENCE: 44

Gln Thr
1

<210> SEQ ID NO 45
<211> LENGTH: 16
<212> TYPE: PRT
<213> ORGANISM: Mus musculus

<400> SEQUENCE: 45

Asp Tyr Phe Asp Tyr Trp Gly Gln Gly Thr Thr Leu Thr Val Ser Ser
1               5                   10                  15

<210> SEQ ID NO 46
<211> LENGTH: 98
<212> TYPE: PRT
<213> ORGANISM: Homo sapiens

<400> SEQUENCE: 46
```

```
Glu Val Gln Leu Val Gln Ser Gly Ala Glu Val Lys Lys Pro Gly Ala
1               5                  10                  15

Thr Val Lys Ile Ser Cys Lys Val Ser Gly Tyr Thr Phe Thr Asp Tyr
            20                  25                  30

Tyr Met His Trp Val Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
            85                  90                  95

Ala Thr

<210> SEQ ID NO 47
<211> LENGTH: 121
<212> TYPE: PRT
<213> ORGANISM: Homo sapiens

<400> SEQUENCE: 47

Met Ser Val Ser Phe Leu Ile Phe Leu Pro Val Leu Gly Leu Pro Trp
1               5                  10                  15

Gly Val Leu Ser Gln Val Gln Leu Gln Gln Ser Gly Pro Gly Leu Val
            20                  25                  30

Lys Pro Ser Gln Thr Leu Ser Leu Thr Cys Ala Ile Ser Gly Asp Ser
            35                  40                  45

Val Ser Ser Asn Ser Ala Ala Trp Asn Trp Ile Arg Gln Ser Pro Ser
    50                  55                  60

Arg Gly Leu Glu Trp Leu Gly Arg Thr Tyr Tyr Arg Ser Lys Trp Tyr
65                  70                  75                  80

Asn Asp Tyr Ala Val Ser Val Lys Ser Arg Ile Thr Ile Asn Pro Asp
            85                  90                  95

Thr Ser Lys Asn Gln Phe Ser Leu Gln Leu Asn Ser Val Thr Pro Glu
            100                 105                 110

Asp Thr Ala Val Tyr Tyr Cys Ala Arg
        115                 120

<210> SEQ ID NO 48
<211> LENGTH: 15
<212> TYPE: PRT
<213> ORGANISM: Homo sapiens

<400> SEQUENCE: 48

Tyr Phe Asp Tyr Trp Gly Gln Gly Thr Leu Val Thr Val Ser Ser
1               5                  10                  15

<210> SEQ ID NO 49
<211> LENGTH: 97
<212> TYPE: PRT
<213> ORGANISM: Homo sapiens

<400> SEQUENCE: 49

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45
```

```
Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala

<210> SEQ ID NO 50
<211> LENGTH: 643
<212> TYPE: DNA
<213> ORGANISM: Mus musculus

<400> SEQUENCE: 50
cagatgaagc tgatttgcat gtgctgagat catattctac tgccccagag atttaataat      60
ctgatcatac acactccaac agtcattctt ggtcaggaga cgttgtagaa atgagaccgt     120
ctattcagtt cctggggctc ttgttgttct ggcttcatgg taaggagttt aacattgaat     180
atgctaaaaa gagtatgtga tcaggaattt ctggtccttc agaaaaatct tctttgaata     240
taattaattt catagggatt tgtgttcttt ttaattatag gtgctcagtg tgacatccag     300
atgacacagt ctccatcctc actgtctgca tctctgggag caaagtcac catcacttgc      360 aaggcaagcc aagacattaa caagtatata gcttggtacc aacacaagcc tggaaaaggt     420
cctaggctgc tcatacatta cacatctaca ttacagccag gcatcccatc aaggttcagt     480
ggaagtgggt ctgggagaga ttattccttc agcatcagca acctggagcc tgaagatatt     540
gcaacttatt attgtctaca gtatgataat cttctaccca cagtgataca atcataaca      600 aaaaccaccc agggaagcag aagtgagagg ctaggttgcc cac                      643

<210> SEQ ID NO 51
<211> LENGTH: 39
<212> TYPE: DNA
<213> ORGANISM: Mus musculus

<400> SEQUENCE: 51
tggacgttcg gtggaggcac caagctggaa atcaaacgt                             39

<210> SEQ ID NO 52
<211> LENGTH: 667
<212> TYPE: DNA
<213> ORGANISM: Homo sapiens

<400> SEQUENCE: 52
ctgcagctgt gcccagcctg ccctatcccc tgctgatttg catgttcgca gagcacagcc      60
ccctgccctg aagacttatt aataggctgg tcgcaccctg tgcaggagtc agtcccaacc     120
aggacacagc atggacatga gggtccctgc tcagctcctg ggctcctgc agctctggct      180 ctcaggtaag gaaggataac actaggaatt ttctcagcca gtgtgctcag tacagcctgg     240
ctcttgatgg aagccttcct ataatatgac taatagtatg aatatttgtg tttatgtttc     300
taatcgcagg tgccagatgt gacatccaga tgacccagtc tccatcctcc ctgtctgcat     360
ctgtaggaga cagagtcacc atcacttgcc aggcgagtca ggacattagc aactatttaa     420
attggtatca gcagaaacca gggaaagccc taagctcct gatctacgat gcatccaatt      480
tggaaacagg ggtcccatca aggttcagtg aagtggatc tgggacagat tttactttca     540
ccatcagcag cctgcagcct gaagatattg caacatatta ctgtcaacag tatgataatc     600
tccctcccac agtgtaacaa gtcataacat aaatcaccca ggggagcaga tgcgtgaggc     660
```

```
tcagctg                                                              667

<210> SEQ ID NO 53
<211> LENGTH: 37
<212> TYPE: DNA
<213> ORGANISM: Homo sapiens

<400> SEQUENCE: 53
tggacgttcg gccaagggac caaggtggaa atcaaac                              37

<210> SEQ ID NO 54
<211> LENGTH: 294
<212> TYPE: DNA
<213> ORGANISM: Mus musculus

<400> SEQUENCE: 54
gagatccagc tgcagcagtc tggacctgag ctggtgaagc ctggggcttc agtgaaggta     60
tcctgcaagg cttctggtta ctcattcact gactacaaca tgtactgggt gaagcagagc    120
catggaaaga gccttgagtg gattggatat attgatcctt acaatggtgg tactagctac    180
aaccagaagt tcaagggcaa ggccacattg actgttgaca gtcctccag cacagccttc     240 atgcatctca acagcctgac atctgaggac tctgcagtct attactgtgc aaga          294

<210> SEQ ID NO 55
<211> LENGTH: 163
<212> TYPE: DNA
<213> ORGANISM: Mus musculus

<400> SEQUENCE: 55
aagcttgccc aggaaccact agtgctcaca cagctctgcc cacaggggaa acctaaccat     60
gcctgccccc tactcagcag gaaggctctg aagctctgag aggattttga caagttact    120 gtcacagtga cagctcgg gctaccatgt aagaaaagct caa                        163

<210> SEQ ID NO 56
<211> LENGTH: 45
<212> TYPE: DNA
<213> ORGANISM: Mus musculus

<400> SEQUENCE: 56
tactttgact actggggcca aggcaccact ctcacagtct cctca                    45

<210> SEQ ID NO 57
<211> LENGTH: 294
<212> TYPE: DNA
<213> ORGANISM: Homo sapiens
<220> FEATURE:
<221> NAME/KEY: CDS
<222> LOCATION: (1)..(294)

<400> SEQUENCE: 57 gag gtc cag ctg gta cag tct ggg gct gag gtg aag aag cct ggg gct      48
Glu Val Gln Leu Val Gln Ser Gly Ala Glu Val Lys Lys Pro Gly Ala
 1               5                  10                  15 aca gtg aaa atc tcc tgc aag gtt tct gga tac acc ttc acc gac tac      96
Thr Val Lys Ile Ser Cys Lys Val Ser Gly Tyr Thr Phe Thr Asp Tyr
             20                  25                  30 tac atg cac tgg gtg caa cag gcc cct gga aaa ggg ctt gag tgg atg     144
Tyr Met His Trp Val Gln Gln Ala Pro Gly Lys Gly Leu Glu Trp Met
         35                  40                  45 gga ctt gtt gat cct gaa gat ggt gaa aca ata tac gca gag aag ttc     192
Gly Leu Val Asp Pro Glu Asp Gly Glu Thr Ile Tyr Ala Glu Lys Phe
```

```
         50                  55                  60
cag ggc aga gtc acc ata acc gcg gac acg tct aca gac aca gcc tac     240
Gln Gly Arg Val Thr Ile Thr Ala Asp Thr Ser Thr Asp Thr Ala Tyr
 65                  70                  75                  80 atg gag ctg agc agc ctg aga tct gag gac acg gcc gtg tat tac tgt     288
Met Glu Leu Ser Ser Leu Arg Ser Glu Asp Thr Ala Val Tyr Tyr Cys
             85                  90                  95 gca aca                                                             294
Ala Thr

<210> SEQ ID NO 58
<211> LENGTH: 17
<212> TYPE: DNA
<213> ORGANISM: Homo sapiens

<400> SEQUENCE: 58
ggtacaactg gaacgac                                                       17

<210> SEQ ID NO 59
<211> LENGTH: 46
<212> TYPE: DNA
<213> ORGANISM: Homo sapiens

<400> SEQUENCE: 59
tactttgact actggggcca aggaaccctg gtcaccgtct cctcag                        46

<210> SEQ ID NO 60
<211> LENGTH: 291
<212> TYPE: DNA
<213> ORGANISM: Homo sapiens

<400> SEQUENCE: 60
ggggcctcag tgaaggtttc ctgcaaggct tctggataca ccttccaggt ccagcttgtg         60
cagtctgggg ctgaggtgaa gaagcctact agctatgcta tgcattgggt gcgccaggcc        120
cccggacaaa ggcttgagtg gatgggatgg atcaacgctg gcaatggtaa cacaaaatat        180
tcacagaagt tccagggcag agtcaccatt accaggaca catccgcgag cacagcctac         240
atggagctga gcagcctgag atctgaagac acggctgtgt attactgtgc g                 291

<210> SEQ ID NO 61
<211> LENGTH: 299
<212> TYPE: PRT
<213> ORGANISM: Homo sapiens

<400> SEQUENCE: 61

Met Gly Thr Lys Ala Gln Val Glu Arg Lys Leu Leu Cys Leu Phe Ile
  1               5                  10                  15

Leu Ala Ile Leu Leu Cys Ser Leu Ala Leu Gly Ser Val Thr Val His
             20                  25                  30

Ser Ser Glu Pro Glu Val Arg Ile Pro Glu Asn Asn Pro Val Lys Leu
         35                  40                  45

Ser Cys Ala Tyr Ser Gly Phe Ser Ser Pro Arg Val Glu Trp Lys Phe
     50                  55                  60

Asp Gln Gly Asp Thr Thr Arg Leu Val Cys Tyr Asn Asn Lys Ile Thr
 65                  70                  75                  80

Ala Ser Tyr Glu Asp Arg Val Thr Phe Leu Pro Thr Gly Ile Thr Phe
             85                  90                  95

Lys Ser Val Thr Arg Glu Asp Thr Gly Thr Tyr Thr Cys Met Val Ser
            100                 105                 110
```

-continued

```
Glu Glu Gly Gly Asn Ser Tyr Gly Glu Val Lys Val Lys Leu Ile Val
            115                 120                 125
Leu Val Pro Pro Ser Lys Pro Thr Val Asn Ile Pro Ser Ser Ala Thr
        130                 135                 140
Ile Gly Asn Arg Ala Val Leu Thr Cys Ser Glu Gln Asp Gly Ser Pro
145                 150                 155                 160
Pro Ser Glu Tyr Thr Trp Phe Lys Asp Gly Ile Val Met Pro Thr Asn
                165                 170                 175
Pro Lys Ser Thr Arg Ala Phe Ser Asn Ser Ser Tyr Val Leu Asn Pro
            180                 185                 190
Thr Thr Gly Glu Leu Val Phe Asp Pro Leu Ser Ala Ser Asp Thr Gly
        195                 200                 205
Glu Tyr Ser Cys Glu Ala Arg Asn Gly Tyr Gly Thr Pro Met Thr Ser
    210                 215                 220
Asn Ala Val Arg Met Glu Ala Val Glu Arg Asn Val Gly Val Ile Val
225                 230                 235                 240
Ala Ala Val Leu Val Thr Leu Ile Leu Leu Gly Ile Leu Val Phe Gly
                245                 250                 255
Ile Trp Phe Ala Tyr Ser Arg Gly His Phe Asp Arg Thr Lys Lys Gly
            260                 265                 270
Thr Ser Ser Lys Lys Val Ile Tyr Ser Gln Pro Ser Ala Arg Ser Glu
        275                 280                 285
Gly Glu Phe Lys Gln Thr Ser Ser Phe Leu Val
        290                 295

<210> SEQ ID NO 62
<211> LENGTH: 897
<212> TYPE: DNA
<213> ORGANISM: Homo sapiens

<400> SEQUENCE: 62
atggggacaa aggcgcaagt cgagaggaaa ctgttgtgcc tcttcatatt ggcgatcctg      60
ttgtgctccc tggcattggg cagtgttaca gtgcactctt ctgaacctga agtcagaatt     120
cctgagaata atcctgtgaa gttgtcctgt gcctactcgg cttttcttc tccccgtgtg     180 gagtggaagt tgaccaagg agacaccacc agactcgttt gctataataa caagatcaca     240
gcttcctatg aggaccgggt gaccttcttg ccaactggta tcaccttcaa gtccgtgaca     300
cgggaagaca ctgggacata cacttgtatg gtctctgagg aaggcggcaa cagctatggg     360
gaggtcaagg tcaagctcat cgtgcttgtg cctccatcca agcctacagt aacatcccc     420 tcctctgcca ccattgggaa ccgggcagtg ctgacatgct cagaacaaga tggttcccca     480
ccttctgaat acacctggtt caagatggg atagtgatgc ctacgaatcc aaaagcacc     540 cgtgccttca gcaactcttc ctatgtcctg aatcccacaa caggagagct ggtctttgat     600
cccctgtcag cctctgatac tggagaatac agctgtgagg cacggaatgg gtatgggaca     660
cccatgactt caaatgctgt gcgcatggaa gctgtggagc ggaatgtggg ggtcatcgtg     720
gcagccgtcc ttgtaaccct gattctcctg ggaatcttgg ttttttggcat ctggtttgcc     780 tatagccgag gccactttga cagaacaaag aaagggactt cgagtaagaa ggtgatttac     840
agccagccta gtgcccgaag tgaaggagaa ttcaaacaga cctcgtcatt cctggtg        897

<210> SEQ ID NO 63
<211> LENGTH: 259
<212> TYPE: PRT
<213> ORGANISM: Homo sapiens
```

<400> SEQUENCE: 63

Met Gly Thr Lys Ala Gln Val Glu Arg Lys Leu Leu Cys Leu Phe Ile
1               5                   10                  15

Leu Ala Ile Leu Pro Glu Asn Asn Pro Val Lys Leu Ser Cys Ala Tyr
            20                  25                  30

Ser Gly Phe Ser Ser Pro Arg Ala Ser Tyr Glu Asp Arg Val Thr
        35                  40                  45

Phe Leu Pro Thr Gly Ile Thr Phe Lys Ser Val Thr Arg Glu Asp Thr
    50                  55                  60

Gly Thr Tyr Thr Cys Met Val Ser Glu Glu Gly Asn Ser Tyr Gly
65                  70                  75                  80

Glu Val Lys Val Lys Leu Ile Val Leu Val Pro Ser Lys Pro Thr
                85                  90                  95

Val Asn Ile Pro Ser Ser Ala Thr Ile Gly Asn Arg Ala Val Leu Thr
            100                 105                 110

Cys Ser Glu Gln Asp Gly Ser Pro Pro Ser Glu Tyr Thr Trp Phe Lys
        115                 120                 125

Asp Gly Ile Val Met Pro Thr Asn Pro Lys Ser Thr Arg Ala Phe Ser
130                 135                 140

Asn Ser Ser Tyr Val Leu Asn Pro Thr Thr Gly Glu Leu Val Phe Asp
145                 150                 155                 160

Pro Leu Ser Ala Ser Asp Thr Gly Glu Tyr Ser Cys Glu Ala Arg Asn
                165                 170                 175

Gly Tyr Gly Thr Pro Met Thr Ser Asn Ala Val Arg Met Glu Ala Val
            180                 185                 190

Glu Arg Asn Val Gly Val Ile Val Ala Ala Val Leu Val Thr Leu Ile
        195                 200                 205

Leu Leu Gly Ile Leu Val Phe Gly Ile Trp Phe Ala Tyr Ser Arg Gly
    210                 215                 220

His Phe Asp Arg Thr Lys Lys Gly Thr Ser Ser Lys Lys Val Ile Tyr
225                 230                 235                 240

Ser Gln Pro Ser Ala Arg Ser Glu Gly Glu Phe Lys Gln Thr Ser Ser
                245                 250                 255

Phe Leu Val

<210> SEQ ID NO 64
<211> LENGTH: 777
<212> TYPE: DNA
<213> ORGANISM: Homo sapiens

<400> SEQUENCE: 64
atggggacaa aggcgcaagt cgagaggaaa ctgttgtgcc tcttcatatt ggcgatcctt      60
cctgagaata atcctgtgaa gttgtcctgt gcctactcgg cttttcttc tccccgtgca     120 gcttcctatg aggaccgggt gaccttcttg ccaactggta tcaccttcaa gtccgtgaca     180
cgggaagaca ctgggacata cacttgtatg gtctctgagg aaggcggcaa cagctatggg     240
gaggtcaagg tcaagctcat cgtgcttgtg cctccatcca agcctacagt taacatcccc     300
tcctctgcca ccattgggaa ccgggcagtg ctgacatgct cagaacaaga tggttcccca     360
ccttctgaat acacctggtt caaagatggg atagtgatgc ctacgaatcc aaaagcacc     420 cgtgccttca gcaactcttc ctatgtcctg aatccacaa caggagagct ggtctttgat     480
cccctgtcag cctctgatac tggagaatac agctgtgagg cacggaatgg gtatgggaca     540
cccatgactt caaatgctgt gcgcatggaa gctgtggagc ggaatgtggg ggtcatcgtg     600

```
gcagccgtcc ttgtaaccct gattctcctg ggaatcttgg tttttggcat ctggtttgcc      660
tatagccgag ccactttga cagaacaaag aaagggactt cgagtaagaa ggtgatttac      720
agccagccta gtgcccgaag tgaaggagaa ttcaaacaga cctcgtcatt cctggtg        777
```

```
<210> SEQ ID NO 65
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or Gln
<220> FEATURE:
<221> NAME/KEY: MOD_RES
<222> LOCATION: (5)..(5)
<223> OTHER INFORMATION: Val or Gln
<220> FEATURE:
<221> NAME/KEY: MOD_RES
<222> LOCATION: (44)..(44)
<223> OTHER INFORMATION: Ser or Arg
<220> FEATURE:
<221> NAME/KEY: MOD_RES
<222> LOCATION: (50)..(50)
<223> OTHER INFORMATION: Tyr or Trp
<220> FEATURE:
<221> NAME/KEY: MOD_RES
<222> LOCATION: (59)..(59)
<223> OTHER INFORMATION: Arg or Lys
<220> FEATURE:
<221> NAME/KEY: MOD_RES
<222> LOCATION: (68)..(68)
<223> OTHER INFORMATION: Ala or Val
<220> FEATURE:
<221> NAME/KEY: MOD_RES
<222> LOCATION: (70)..(70)
<223> OTHER INFORMATION: Leu or Ile
<220> FEATURE:
<221> NAME/KEY: MOD_RES
<222> LOCATION: (72)..(72)
<223> OTHER INFORMATION: Val or Arg
<220> FEATURE:
<221> NAME/KEY: MOD_RES
<222> LOCATION: (82)..(82)
<223> OTHER INFORMATION: His or Glu

<400> SEQUENCE: 65

Xaa Val Gln Leu Xaa Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
                20                  25                  30

Ser Met His Trp Val Arg Gln Ala Pro Gly Gln Xaa Leu Glu Trp Met
            35                  40                  45

Gly Xaa Ile Asp Pro Tyr Asn Gly Gly Thr Xaa Tyr Ser Gln Lys Phe
        50                  55                  60

Gln Gly Arg Xaa Thr Xaa Thr Xaa Asp Thr Ser Ala Ser Thr Ala Tyr
65                  70                  75                  80

Met Xaa Leu Ser Ser Leu Arg Ser Glu Asp Thr Ala Val Tyr Tyr Cys
                85                  90                  95

Ala Arg Gln Thr Asp Tyr Phe Asp Tyr Trp Gly Gln Gly Thr Leu Val
                100                 105                 110

Thr Val Ser Ser
            115

<210> SEQ ID NO 66
<211> LENGTH: 116
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or Gln
<220> FEATURE:
<221> NAME/KEY: MOD_RES
<222> LOCATION: (5)..(5)
<223> OTHER INFORMATION: Val or Gln
<220> FEATURE:
<221> NAME/KEY: MOD_RES
<222> LOCATION: (44)..(44)
<223> OTHER INFORMATION: Ser or Gly
<220> FEATURE:
<221> NAME/KEY: MOD_RES
<222> LOCATION: (50)..(50)
<223> OTHER INFORMATION: Tyr or Ile
<220> FEATURE:
<221> NAME/KEY: MOD_RES
<222> LOCATION: (59)..(59)
<223> OTHER INFORMATION: Arg or Ser
<220> FEATURE:
<221> NAME/KEY: MOD_RES
<222> LOCATION: (68)..(68)
<223> OTHER INFORMATION: Ala or Val
<220> FEATURE:
<221> NAME/KEY: MOD_RES
<222> LOCATION: (70)..(70)
<223> OTHER INFORMATION: Leu or Met
<220> FEATURE:
<221> NAME/KEY: MOD_RES
<222> LOCATION: (72)..(72)
<223> OTHER INFORMATION: Val or Arg
<220> FEATURE:
<221> NAME/KEY: MOD_RES
<222> LOCATION: (82)..(82)
<223> OTHER INFORMATION: His or Glu

<400> SEQUENCE: 66

Xaa Val Gln Leu Xaa Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
                20                  25                  30

Ser Met His Trp Val Arg Gln Ala Pro Gly Gln Xaa Leu Glu Trp Met
            35                  40                  45

Gly Xaa Ile Asp Pro Tyr Asn Gly Gly Thr Xaa Tyr Ala Gln Lys Phe
        50                  55                  60

Gln Gly Arg Xaa Thr Xaa Thr Xaa Asp Thr Ser Thr Ser Thr Val Tyr
65                  70                  75                  80

Met Xaa Leu Ser Ser Leu Arg Ser Glu Asp Thr Ala Val Tyr Tyr Cys
            85                  90                  95

Ala Arg Gln Thr Asp Tyr Phe Asp Tyr Trp Gly Gln Gly Thr Leu Val
                100                 105                 110

Thr Val Ser Ser
            115

<210> SEQ ID NO 67
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Lys or Arg
```

```
<220> FEATURE:
<221> NAME/KEY: MOD_RES
<222> LOCATION: (33)..(33)
<223> OTHER INFORMATION: Leu or Ile
<220> FEATURE:
<221> NAME/KEY: MOD_RES
<222> LOCATION: (49)..(49)
<223> OTHER INFORMATION: His or Tyr
<220> FEATURE:
<221> NAME/KEY: MOD_RES
<222> LOCATION: (71)..(71)
<223> OTHER INFORMATION: Tyr or Phe

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Xaa Ala Ser Gln Asp Ile Asn Asn Tyr
            20                  25                  30

Xaa Ala Trp Tyr Gln Gln Lys Pro Gly Lys Val Pro Lys Leu Leu Ile
        35                  40                  45

Xaa Tyr Thr Ser Thr Leu Gln Ser Gly Val Pro Ser Arg Phe Ser Gly
        50                  55                  60

Ser Gly Ser Gly Thr Asp Xaa Thr Leu Thr Ile Ser Ser Leu Gln Pro
65                  70                  75                  80

Glu Asp Val Ala Thr Tyr Tyr Cys Leu Gln Tyr Asp Asn Leu Trp Thr
                85                  90                  95

Phe Gly Gln Gly Thr Lys Val Glu Ile Lys
            100                 105

<210> SEQ ID NO 68
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Asp or Ala
<220> FEATURE:
<221> NAME/KEY: MOD_RES
<222> LOCATION: (3)..(3)
<223> OTHER INFORMATION: Arg or Gln
<220> FEATURE:
<221> NAME/KEY: MOD_RES
<222> LOCATION: (24)..(24)
<223> OTHER INFORMATION: Lys or Trp
<220> FEATURE:
<221> NAME/KEY: MOD_RES
<222> LOCATION: (33)..(33)
<223> OTHER INFORMATION: Leu or Ile
<220> FEATURE:
<221> NAME/KEY: MOD_RES
<222> LOCATION: (49)..(49)
<223> OTHER INFORMATION: His or Tyr
<220> FEATURE:
<221> NAME/KEY: MOD_RES
<222> LOCATION: (53)..(53)
<223> OTHER INFORMATION: Ser or Thr

<400> SEQUENCE: 68

Xaa Ile Xaa Met Thr Gln Ser Pro Phe Ser Leu Ser Ala Ser Val Gly
1               5                   10                  15

Asp Arg Val Thr Ile Thr Cys Xaa Ala Ser Gln Asp Ile Asn Asn Tyr
            20                  25                  30

Xaa Ala Trp Tyr Gln Gln Lys Pro Ala Lys Ala Pro Lys Leu Phe Ile
        35                  40                  45
```

```
Xaa Tyr Thr Ser Xaa Leu Gln Ser Gly Val Pro Ser Arg Phe Ser Gly
     50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Leu Gln Tyr Asp Asn Leu Trp Thr
                 85                  90                  95

Phe Gly Gln Gly Thr Lys Val Glu Ile Lys
            100                 105

<210> SEQ ID NO 69
<211> LENGTH: 319
<212> TYPE: DNA
<213> ORGANISM: Mus musculus
<220> FEATURE:
<221> NAME/KEY: CDS
<222> LOCATION: (1)..(318)

<400> SEQUENCE: 69 gac atc cag atg aca cag tct cca tcc tca ctg tct gca tct ctg gga    48
Asp Ile Gln Met Thr Gln Ser Pro Ser Ser Leu Ser Ala Ser Leu Gly
 1               5                  10                  15 ggc aaa gtc acc atc act tgc aag gca agc caa gac att aac aat tat    96
Gly Lys Val Thr Ile Thr Cys Lys Ala Ser Gln Asp Ile Asn Asn Tyr
             20                  25                  30 ata gct tgg tac caa cac aag cct gga aaa ggt cct agg ctg ctc ata   144
Ile Ala Trp Tyr Gln His Lys Pro Gly Lys Gly Pro Arg Leu Leu Ile
         35                  40                  45 cat tac aca tct aca tta caa gca ggc atc cca tca agg ttc agt gga   192
His Tyr Thr Ser Thr Leu Gln Ala Gly Ile Pro Ser Arg Phe Ser Gly
     50                  55                  60 agt ggg tct ggg aga gat tat tcc ttc agc atc agc aac ctg gag cct   240
Ser Gly Ser Gly Arg Asp Tyr Ser Phe Ser Ile Ser Asn Leu Glu Pro
 65                  70                  75                  80 gaa gat att gga act tat tat tgt cta cag tat gat aat ctg tgg acg   288
Glu Asp Ile Gly Thr Tyr Tyr Cys Leu Gln Tyr Asp Asn Leu Trp Thr
                 85                  90                  95 ttc ggt gga ggc acc aag ctg gaa atc aaa c                         319
Phe Gly Gly Gly Thr Lys Leu Glu Ile Lys
            100                 105

<210> SEQ ID NO 70
<211> LENGTH: 287
<212> TYPE: DNA
<213> ORGANISM: Mus musculus

<400> SEQUENCE: 70
gacatccaga tgacacagtc tccatcctca ctgtctgcat ctctgggagg caaagtcacc    60
atcacttgca aggcaagcca agacattaac aagtatatag cttggtacca acacaagcct   120
ggaaaaggtc ctaggctgct catacattac acatctacat tacagccagg catcccatca   180
aggttcagtg gaagtgggtc tgggagagat tattccttca gcatcagcaa cctggagcct   240
gaagatattg caacttatta ttgtctacag tatgataatc ttctacc                 287

<210> SEQ ID NO 71
<211> LENGTH: 38
<212> TYPE: DNA
<213> ORGANISM: Mus musculus
<220> FEATURE:
<221> NAME/KEY: CDS
<222> LOCATION: (2)..(37)

<400> SEQUENCE: 71
```

```
                                                             -continued g tgg acg ttc ggt gga ggc acc aag ctg gaa atc aaa c                    38
  Trp Thr Phe Gly Gly Gly Thr Lys Leu Glu Ile Lys
  1               5                   10

<210> SEQ ID NO 72
<211> LENGTH: 312
<212> TYPE: DNA
<213> ORGANISM: Mus musculus
<220> FEATURE:
<221> NAME/KEY: CDS
<222> LOCATION: (1)..(312)

<400> SEQUENCE: 72 gac atc cag atg aca cag tct cca tcc tca ctg tct gca tct ctg gga      48
Asp Ile Gln Met Thr Gln Ser Pro Ser Ser Leu Ser Ala Ser Leu Gly
1               5                   10                  15 ggc aaa gtc acc atc act tgc aag gca agc caa gac att aac aat tat      96
Gly Lys Val Thr Ile Thr Cys Lys Ala Ser Gln Asp Ile Asn Asn Tyr
                20                  25                  30 ata gct tgg tac caa cac aag cct gga aaa ggt cct agg ctg ctc ata     144
Ile Ala Trp Tyr Gln His Lys Pro Gly Lys Gly Pro Arg Leu Leu Ile
            35                  40                  45 cat tac aca tct aca tta caa gca ggc atc cca tca agg ttc agt gga     192
His Tyr Thr Ser Thr Leu Gln Ala Gly Ile Pro Ser Arg Phe Ser Gly
        50                  55                  60 agt ggg tct ggg aga gat tat tcc ttc agc atc agc aac ctg gag cct     240
Ser Gly Ser Gly Arg Asp Tyr Ser Phe Ser Ile Ser Asn Leu Glu Pro
65                  70                  75                  80 gaa gat att gga act tat tat tgt cta cag tat gat aat ctg tgg acg     288
Glu Asp Ile Gly Thr Tyr Tyr Cys Leu Gln Tyr Asp Asn Leu Trp Thr
                85                  90                  95 ttc ggt gga ggc acc aag ctg gaa                                     312
Phe Gly Gly Gly Thr Lys Leu Glu
            100

<210> SEQ ID NO 73
<211> LENGTH: 104
<212> TYPE: PRT
<213> ORGANISM: Mus musculus

<400> SEQUENCE: 73

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Asn Tyr
                20                  25                  30

Ile Ala Trp Tyr Gln His Lys Pro Gly Lys Gly Pro Arg Leu Leu Ile
            35                  40                  45

His Tyr Thr Ser Thr Leu Gln Ala Gly Ile Pro Ser Arg Phe Ser Gly
        50                  55                  60

Ser Gly Ser Gly Arg Asp Tyr Ser Phe Ser Ile Ser Asn Leu Glu Pro
65                  70                  75                  80

Glu Asp Ile Gly Thr Tyr Tyr Cys Leu Gln Tyr Asp Asn Leu Trp Thr
                85                  90                  95

Phe Gly Gly Gly Thr Lys Leu Glu
            100

<210> SEQ ID NO 74
<211> LENGTH: 287
<212> TYPE: DNA
<213> ORGANISM: Homo sapiens
<220> FEATURE:
<221> NAME/KEY: CDS
<222> LOCATION: (1)..(285)
```

<400> SEQUENCE: 74

```
gac atc cag atg acc cag tct cca tcc tcc ctg tct gca tct gta gga      48
Asp Ile Gln Met Thr Gln Ser Pro Ser Ser Leu Ser Ala Ser Val Gly
1               5                   10                  15 gac aga gtc acc atc act tgc cag gcg agt cag gac att agc aac tat      96
Asp Arg Val Thr Ile Thr Cys Gln Ala Ser Gln Asp Ile Ser Asn Tyr
            20                  25                  30 tta aat tgg tat cag cag aaa cca ggg aaa gcc cct aag ctc ctg atc     144
Leu Asn Trp Tyr Gln Gln Lys Pro Gly Lys Ala Pro Lys Leu Leu Ile
        35                  40                  45 tac gat gca tcc aat ttg gaa aca ggg gtc cca tca agg ttc agt gga     192
Tyr Asp Ala Ser Asn Leu Glu Thr Gly Val Pro Ser Arg Phe Ser Gly
    50                  55                  60 agt gga tct ggg aca gat ttt act ttc acc atc agc agc ctg cag cct     240
Ser Gly Ser Gly Thr Asp Phe Thr Phe Thr Ile Ser Ser Leu Gln Pro
65                  70                  75                  80 gaa gat att gca aca tat tac tgt caa cag tat gat aat ctc cct cc      287
Glu Asp Ile Ala Thr Tyr Tyr Cys Gln Gln Tyr Asp Asn Leu Pro
                85                  90                  95
```

<210> SEQ ID NO 75
<211> LENGTH: 95
<212> TYPE: PRT
<213> ORGANISM: Homo sapiens

<400> SEQUENCE: 75

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95
```

<210> SEQ ID NO 76
<211> LENGTH: 37
<212> TYPE: DNA
<213> ORGANISM: Mus musculus
<220> FEATURE:
<221> NAME/KEY: CDS
<222> LOCATION: (2)..(37)

<400> SEQUENCE: 76

```
g tgg acg ttc ggt gga ggc acc aag ctg gaa atc aaa                    37
  Trp Thr Phe Gly Gly Gly Thr Lys Leu Glu Ile Lys
  1               5                   10
```

<210> SEQ ID NO 77
<211> LENGTH: 37
<212> TYPE: DNA
<213> ORGANISM: Homo sapiens
<220> FEATURE:
<221> NAME/KEY: CDS
<222> LOCATION: (2)..(37)

<400> SEQUENCE: 77

```
g tgg acg ttc ggc caa ggg acc aag gtg gaa atc aaa                    37
```

```
  Trp Thr Phe Gly Gln Gly Thr Lys Val Glu Ile Lys
  1               5                  10
```

<210> SEQ ID NO 78
<211> LENGTH: 12
<212> TYPE: PRT
<213> ORGANISM: Homo sapiens

<400> SEQUENCE: 78

```
Trp Thr Phe Gly Gln Gly Thr Lys Val Glu Ile Lys
1               5                  10
```

<210> SEQ ID NO 79
<211> LENGTH: 349
<212> TYPE: DNA
<213> ORGANISM: Mus musculus
<220> FEATURE:
<221> NAME/KEY: CDS
<222> LOCATION: (1)..(348)

<400> SEQUENCE: 79

```
gag atc cag ctg cag cag tct gga cct gag ctg gtg aag cct ggg gct        48
Glu Ile Gln Leu Gln Gln Ser Gly Pro Glu Leu Val Lys Pro Gly Ala
1               5                  10                  15 tca gtg aag gta tcc tgc aag gct tct ggt tac tca ttc act gac tac        96
Ser Val Lys Val Ser Cys Lys Ala Ser Gly Tyr Ser Phe Thr Asp Tyr
            20                  25                  30 agc atg tac tgg gtg aag cag agc cat gga aag agc ctt gag tgg att       144
Ser Met Tyr Trp Val Lys Gln Ser His Gly Lys Ser Leu Glu Trp Ile
        35                  40                  45 gga tat att gat cct tac aat ggt ggt act agg tac aac cag aag ttc       192
Gly Tyr Ile Asp Pro Tyr Asn Gly Gly Thr Arg Tyr Asn Gln Lys Phe
    50                  55                  60 aag ggc aag gcc aca ttg act gtt gac aag tcc tcc agc aca gcc ttc       240
Lys Gly Lys Ala Thr Leu Thr Val Asp Lys Ser Ser Ser Thr Ala Phe
65                  70                  75                  80 atg cat ctc aac agc ctg aca tct gag gac tct gca gtc tat tac tgt       288
Met His Leu Asn Ser Leu Thr Ser Glu Asp Ser Ala Val Tyr Tyr Cys
                85                  90                  95 gca aga cag acg gac tac ttt gac tac tgg ggc caa ggc acc act ctc       336
Ala Arg Gln Thr Asp Tyr Phe Asp Tyr Trp Gly Gln Gly Thr Thr Leu
            100                 105                 110 aca gtc tcc tca g                                                     349
Thr Val Ser Ser
        115
```

<210> SEQ ID NO 80
<211> LENGTH: 6
<212> TYPE: PRT
<213> ORGANISM: Mus musculus

<400> SEQUENCE: 80

```
Ala Arg Gln Thr Asp Tyr
1               5
```

<210> SEQ ID NO 81
<211> LENGTH: 16
<212> TYPE: DNA
<213> ORGANISM: Mus musculus

<400> SEQUENCE: 81 agacagctc gggctac                                                      16

<210> SEQ ID NO 82

```
<211> LENGTH: 18
<212> TYPE: PRT
<213> ORGANISM: Mus musculus

<400> SEQUENCE: 82

Gln Thr Asp Tyr Phe Asp Tyr Trp Gly Gln Gly Thr Thr Leu Thr Val
1               5                   10                  15

Ser Ser

<210> SEQ ID NO 83
<211> LENGTH: 54
<212> TYPE: DNA
<213> ORGANISM: Mus musculus
<220> FEATURE:
<221> NAME/KEY: CDS
<222> LOCATION: (1)..(54)

<400> SEQUENCE: 83 cag acg gac tac ttt gac tac tgg ggc caa ggc acc act ctc aca gtc      48
Gln Thr Asp Tyr Phe Asp Tyr Trp Gly Gln Gly Thr Thr Leu Thr Val
1               5                   10                  15 tcc tca                                                              54
Ser Ser

<210> SEQ ID NO 84
<211> LENGTH: 47
<212> TYPE: DNA
<213> ORGANISM: Mus musculus

<400> SEQUENCE: 84
actactttga ctactggggc caaggcacca ctctcacagt ctcctca                  47

<210> SEQ ID NO 85
<211> LENGTH: 336
<212> TYPE: DNA
<213> ORGANISM: Mus musculus
<220> FEATURE:
<221> NAME/KEY: CDS
<222> LOCATION: (1)..(336)

<400> SEQUENCE: 85 gag atc cag ctg cag cag tct gga cct gag ctg gtg aag cct ggg gct      48
Glu Ile Gln Leu Gln Gln Ser Gly Pro Glu Leu Val Lys Pro Gly Ala
1               5                   10                  15 tca gtg aag gta tcc tgc aag gct tct ggt tac tca ttc act gac tac      96
Ser Val Lys Val Ser Cys Lys Ala Ser Gly Tyr Ser Phe Thr Asp Tyr
                20                  25                  30 agc atg tac tgg gtg aag cag agc cat gga aag agc ctt gag tgg att     144
Ser Met Tyr Trp Val Lys Gln Ser His Gly Lys Ser Leu Glu Trp Ile
            35                  40                  45 gga tat att gat cct tac aat ggt ggt act agg tac aac cag aag ttc     192
Gly Tyr Ile Asp Pro Tyr Asn Gly Gly Thr Arg Tyr Asn Gln Lys Phe
        50                  55                  60 aag ggc aag gcc aca ttg act gtt gac aag tcc tcc agc aca gcc ttc     240
Lys Gly Lys Ala Thr Leu Thr Val Asp Lys Ser Ser Ser Thr Ala Phe
65                  70                  75                  80 atg cat ctc aac agc ctg aca tct gag gac tct gca gtc tat tac tgt     288
Met His Leu Asn Ser Leu Thr Ser Glu Asp Ser Ala Val Tyr Tyr Cys
                85                  90                  95 gca aga cag acg gac tac ttt gac tac tgg ggc caa ggc acc act ctc     336
Ala Arg Gln Thr Asp Tyr Phe Asp Tyr Trp Gly Gln Gly Thr Thr Leu
                100                 105                 110

<210> SEQ ID NO 86
```

```
<211> LENGTH: 112
<212> TYPE: PRT
<213> ORGANISM: Mus musculus

<400> SEQUENCE: 86

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Tyr
            20                  25                  30

Ser Met Tyr Trp Val Lys Gln Ser His Gly Lys Ser Leu Glu Trp Ile
        35                  40                  45

Gly Tyr Ile Asp Pro Tyr Asn Gly Gly Thr Arg Tyr Asn Gln Lys Phe
    50                  55                  60

Lys Gly Lys Ala Thr Leu Thr Val Asp Lys Ser Ser Ser Thr Ala Phe
65                  70                  75                  80

Met His Leu Asn Ser Leu Thr Ser Glu Asp Ser Ala Val Tyr Tyr Cys
                85                  90                  95

Ala Arg Gln Thr Asp Tyr Phe Asp Tyr Trp Gly Gln Gly Thr Thr Leu
            100                 105                 110

<210> SEQ ID NO 87
<211> LENGTH: 15
<212> TYPE: DNA
<213> ORGANISM: Mus musculus
<220> FEATURE:
<221> NAME/KEY: CDS
<222> LOCATION: (1)..(15)

<400> SEQUENCE: 87 cag acg gac tac ttt                                              15
Gln Thr Asp Tyr Phe
1               5

<210> SEQ ID NO 88
<211> LENGTH: 5
<212> TYPE: PRT
<213> ORGANISM: Mus musculus

<400> SEQUENCE: 88

Gln Thr Asp Tyr Phe
1               5

<210> SEQ ID NO 89
<211> LENGTH: 56
<212> TYPE: DNA
<213> ORGANISM: Mus musculus
<220> FEATURE:
<221> NAME/KEY: CDS
<222> LOCATION: (9)..(56)

<400> SEQUENCE: 89 gacagacg gac tac ttt gac tac tgg ggc caa ggc acc act ctc aca gtc  50
         Asp Tyr Phe Asp Tyr Trp Gly Gln Gly Thr Thr Leu Thr Val
         1               5                   10 tcc tca                                                          56
Ser Ser
15

<210> SEQ ID NO 90
<211> LENGTH: 47
<212> TYPE: DNA
<213> ORGANISM: Homo sapiens
<220> FEATURE:
<221> NAME/KEY: CDS
<222> LOCATION: (3)..(47)
```

<400> SEQUENCE: 90

```
ac tac ttt gac tac tgg ggc caa gga acc ctg gtc acc gtc tcc tca        47
   Tyr Phe Asp Tyr Trp Gly Gln Gly Thr Leu Val Thr Val Ser Ser
    1               5                  10                  15
```

<210> SEQ ID NO 91
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Asn Tyr
            20                  25                  30

Ile Ala Trp Tyr Gln Gln Lys Pro Gly Lys Ala Pro Lys Leu Leu Ile
        35                  40                  45

His Tyr Thr Ser Thr Leu Gln Ala Gly Val Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Trp Thr
                85                  90                  95

Phe Gly Gln Gly Thr Lys Val Glu Ile Lys
            100                 105
```

<210> SEQ ID NO 92
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

```
Glu Ile Gln Leu Val Gln Ser Gly Ala Glu Val Lys Lys Pro Gly Ala
1               5                   10                  15

Thr Val Lys Ile Ser Cys Lys Val Ser Gly Tyr Ser Phe Thr Asp Tyr
            20                  25                  30

Ser Met Tyr Trp Val Gln Gln Ala Pro Gly Lys Gly Leu Glu Trp Ile
        35                  40                  45

Gly Tyr Ile Asp Pro Tyr Asn Gly Gly Thr Arg Tyr Asn Gln Lys Phe
    50                  55                  60

Lys Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Thr Asp Tyr Phe Asp Tyr Trp Gly Gln Gly Thr Leu Val
            100                 105                 110

Thr Val Ser Ser
        115
```

<210> SEQ ID NO 93
<211> LENGTH: 97
<212> TYPE: PRT
<213> ORGANISM: Mus musculus

<400> SEQUENCE: 93

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Tyr
            20                  25                  30

Ser Met Tyr Trp Val Lys Gln Ser His Gly Lys Ser Leu Glu Trp Ile
        35                  40                  45

Gly Tyr Ile Asp Pro Tyr Asn Gly Gly Thr Arg Tyr Asn Gln Lys Phe
    50                  55                  60

Lys Gly Lys Ala Thr Leu Thr Val Asp Lys Ser Ser Ser Thr Ala Phe
65                  70                  75                  80

Met His Leu Asn Ser Leu Thr Ser Glu Asp Ser Ala Val Tyr Tyr Cys
                85                  90                  95

Ala

<210> SEQ ID NO 94
<211> LENGTH: 97
<212> TYPE: PRT
<213> ORGANISM: Mus musculus

<400> SEQUENCE: 94

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ser Met His Trp Val Arg Gln Ala Pro Gly Gln Arg Leu Glu Trp Met
        35                  40                  45

Gly Trp Ile Asp Pro Tyr Asn Gly Gly Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala

<210> SEQ ID NO 95
<211> LENGTH: 97
<212> TYPE: PRT
<213> ORGANISM: Mus musculus

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ser Met His Trp Val Arg Gln Ala Pro Gly Gln Arg Leu Glu Trp Met
        35                  40                  45

Gly Tyr Ile Asp Pro Tyr Asn Gly Gly Thr Arg Tyr Ser Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala

<210> SEQ ID NO 96

```
<211> LENGTH: 106
<212> TYPE: PRT
<213> ORGANISM: Homo sapiens

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Tyr Gln Gln Lys Pro Gly Lys Val Pro Lys Leu Leu Ile
        35                  40                  45

Tyr Tyr Thr Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Gly Thr Tyr Tyr Cys Leu Gln Tyr Asp Asn Leu Trp Thr
                85                  90                  95

Phe Gly Gln Gly Thr Lys Val Glu Ile Lys
            100                 105

<210> SEQ ID NO 97
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Asn Tyr
            20                  25                  30

Ile Ala Trp Tyr Gln Gln Lys Pro Gly Lys Val Pro Lys Leu Leu Ile
        35                  40                  45

His Tyr Thr Ser Thr Leu Gln Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Val Gly Thr Tyr Tyr Cys Leu Gln Tyr Asp Asn Leu Trp Thr
                85                  90                  95

Phe Gly Gln Gly Thr Lys Val Glu Ile Lys
            100                 105

<210> SEQ ID NO 98
<211> LENGTH: 106
<212> TYPE: PRT
<213> ORGANISM: Homo sapiens

<400> SEQUENCE: 98

Ala Ile Arg Met Thr Gln Ser Pro Phe Ser Leu Ser Ala Ser Val Gly
1               5                   10                  15

Asp Arg Val Thr Ile Thr Cys Trp Ala Ser Gln Asp Ile Asn Asn Tyr
            20                  25                  30

Leu Ala Trp Tyr Gln Gln Lys Pro Ala Lys Ala Pro Lys Leu Phe Ile
        35                  40                  45

Tyr Tyr Thr Ser Ser Leu Gln Ser Gly Val Pro Ser Arg Phe Ser Gly
50                  55                  60

Ser Gly Ser Gly Thr Asp Tyr Thr Leu Thr Ile Ser Ser Leu Gln Pro
```

```
                65                  70                  75                  80
Glu Asp Phe Ala Thr Tyr Tyr Cys Leu Gln Tyr Asp Asn Leu Trp Thr
                    85                  90                  95
Phe Gly Gln Gly Thr Lys Val Glu Ile Lys
                100                 105
```

<210> SEQ ID NO 99
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Asp Ile Gln Met Thr Gln Ser Pro Phe Ser Leu Ser Ala Ser Val Gly
1               5                   10                  15
Asp Arg Val Thr Ile Thr Cys Lys Ala Ser Gln Asp Ile Asn Asn Tyr
                20                  25                  30
Ile Ala Trp Tyr Gln Gln Lys Pro Ala Lys Ala Pro Lys Leu Phe Ile
            35                  40                  45
His Tyr Thr Ser Thr Leu Gln Ser Gly Val Pro Ser Arg Phe Ser Gly
        50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Leu Gln Tyr Asp Asn Leu Trp Thr
                    85                  90                  95
Phe Gly Gly Gly Thr Lys Leu Glu Ile Lys
                100                 105
```

<210> SEQ ID NO 100
<211> LENGTH: 116
<212> TYPE: PRT
<213> ORGANISM: Homo sapiens

<400> SEQUENCE: 100

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ser Phe Thr Asp Tyr
                20                  25                  30
Ser Met His Trp Val Arg Gln Ala Pro Gly Gln Arg Leu Glu Trp Met
            35                  40                  45
Gly Trp Ile Asp Pro Tyr Asn Gly Gly Thr Lys Tyr Ser Gln Lys Phe
        50                  55                  60
Gln Gly Arg Val Thr Ile Thr Arg Asp Thr Ser Ala Ser Thr Ala Tyr
65                  70                  75                  80
Met Glu Leu Ser Ser Leu Arg Ser Glu Asp Thr Ala Val Tyr Tyr Cys
                    85                  90                  95
Ala Arg Gln Thr Asp Tyr Phe Asp Tyr Trp Gly Gln Gly Thr Leu Val
                100                 105                 110
Thr Val Ser Ser
        115
```

<210> SEQ ID NO 101
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ser Met His Trp Val Arg Gln Ala Pro Gly Gln Ser Leu Glu Trp Met
        35                  40                  45

Gly Tyr Ile Asp Pro Tyr Asn Gly Gly Thr Arg Tyr Ser Gln Lys Phe
    50                  55                  60

Gln Gly Arg Ala Thr Leu Thr Val Asp Thr Ser Ala Ser Thr Ala Tyr
65                  70                  75                  80

Met His Leu Ser Ser Leu Arg Ser Glu Asp Thr Ala Val Tyr Tyr Cys
                85                  90                  95

Ala Arg Gln Thr Asp Tyr Phe Asp Tyr Trp Gly Gln Gly Thr Leu Val
            100                 105                 110

Thr Val Ser Ser
            115

<210> SEQ ID NO 102
<211> LENGTH: 116
<212> TYPE: PRT
<213> ORGANISM: Homo sapiens

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ser Met His Trp Val Arg Gln Ala Pro Gly Gln Gly Leu Glu Trp Met
        35                  40                  45

Gly Ile Ile Asp Pro Tyr Asn Gly Gly Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gln Thr Asp Tyr Phe Asp Tyr Trp Gly Gln Gly Thr Leu Val
            100                 105                 110

Thr Val Ser Ser
            115

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Cys Leu Gln Tyr Asp Asn Leu Trp Thr Phe
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic

```
      peptide

<400> SEQUENCE: 104

Cys Ala Arg Gln Thr Asp Tyr Phe Asp Tyr Trp
1               5                   10
```

ANTI-JAM-A ANTIBODIES

CROSS-REFERENCE TO PRIORITY/PCT APPLICATIONS

This application claims priority under 35 U.S.C. §119 of FR 06/10329, filed Nov. 24, 2006, and is a continuation of PCT/EP 2007/062760, filed Nov. 23, 2007, each hereby expressly incorporated by reference in its entirety and each assigned to the assignee hereof.

BACKGROUND OF THE INVENTION

Technical Field of the Invention

The present invention relates to novel antibodies, in particular murine monoclonal antibodies, chimeric and humanized, able to inhibit tumor growth, as well as the amino and nucleic acid sequences coding for such antibodies. From one aspect, the invention relates to novel antibodies, derived compounds or functional fragments, able to inhibit the proliferation of tumor cells. The invention also comprises the use of such antibodies as a drug for the preventive and/or therapeutic treatment of cancers, as well as in the procedures or kits related to cancer diagnosis. Finally, the invention comprises compositions comprising such antibodies in combination with other anticancer compounds, such as antibodies, or conjugated with toxins, and the use of same for the prevention and/or treatment of certain cancers.

Generally, the criterion selected for the production of monoclonal antibodies is the recognition of the immunogen identified as a potential target of a treatment. In practice, mice are immunized with a recombinant protein that corresponds to the immunogen and, after the monoclonal antibodies produced by the mouse are recovered, they are first screened for their capacity to recognize the immunogen in a specific manner. In a second stage, the antibodies thus selected are tested in vivo and in vitro in order to determine their activity as well as their properties and/or mechanisms of action.

This "traditional" approach, even if it makes it possible to know the working target from the beginning, often generates a large number of antibodies which are certainly capable of specifically recognizing a given target but which in vivo do not exhibit significant biological activity. In the field of cancer, it is indeed known that, even if an antibody produces good results in vitro, that does not inevitably mean that such an antibody will later show genuine anti-tumor activity in vivo.

The present invention differs from this manner of proceeding, and goes even against the aforementioned, since it is based on a "functional" approach, and more particularly on primary screening based on the function sought for the antibody and not on the recognized antigen.

More particularly, the inventors have selected a given function, namely inhibition of basal proliferation, not induced, of the cell, as an antibody selection parameter.

The production method used will be described in more detail in the examples below.

In a surprising way, by this functional approach, the inventors have produced and selected an antibody capable of inhibiting in vitro and/or in vivo, in a significant manner, the proliferation of tumor cells.

According to a first aspect, the invention relates to an isolated antibody, or a derived compound or functional fragment of same, capable of inhibiting the proliferation of tumor cells in vitro and/or in vivo; said antibody, or a derived compound or functional fragment of same, comprising at least one CDR selected among the complementarity-determining regions (CDRs) of sequences SEQ ID No. 1, 2, 3, 4, 5 or 6 or at least one CDR whose sequence has at least 80%, preferably 85%, 90%, 95% and 98% identity after optimal alignment with sequences SEQ ID No. 1, 2, 3, 4, 5 or 6.

A "functional fragment" of an antibody means in particular an antibody fragment, such as fragments Fv, scFv (sc=simple chain), Fab, F(ab')$_2$, Fab', scFv-Fc or diabodies, or any fragment whose half-life has been increased. Such functional fragments will be described in detail later in the present description.

A "derived compound" of an antibody means in particular a binding protein composed of a peptide scaffold and at least one of the CDRs of the original antibody in order to preserve its ability to be recognized. Such derived compounds, well-known to a person skilled in the art, will be described in more detail later in the present description.

More preferably, the invention comprises the antibodies, their derived compounds or their functional fragments, according to the present invention, notably chimeric or humanized, obtained by genetic recombination or chemical synthesis.

According to a preferred embodiment, the antibody according to the invention, or its derived compounds or functional fragments, is characterized in that it consists of a monoclonal antibody.

"Monoclonal antibody" is understood to mean an antibody arising from a nearly homogeneous antibody population. More particularly, the individual antibodies of a population are identical except for a few possible naturally-occurring mutations which can be found in minimal proportions. In other words, a monoclonal antibody consists of a homogeneous antibody arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.) and is generally characterized by heavy chains of one and only one class and subclass, and light chains of only one type. Monoclonal antibodies are highly specific and are directed against a single antigen. In addition, in contrast with preparations of polyclonal antibodies which typically include various antibodies directed against various determinants, or epitopes, each monoclonal antibody is directed against a single epitope of the antigen.

It must be understood here that the invention does not relate to antibodies in natural form, i.e., they are not taken from their natural environment but are isolated or obtained by purification from natural sources or obtained by genetic recombination or chemical synthesis and thus they can carry unnatural amino acids as will be described below.

More particularly, according to a preferred embodiment of the invention, the antibody, or its derived compounds or functional fragments, is characterized in that it comprises a light chain comprising at least one CDR selected among the CDRs of amino acid sequences SEQ ID No. 1, 3 or 5, or at least one CDR whose sequence has at least 80%, preferably 85%, 90%, 95% and 98% identity after optimal alignment with sequences SEQ ID No. 1, 3 or 5; or it comprises a heavy chain comprising at least one CDR selected among the CDRs of amino acid sequences SEQ ID No. 2, 4 or 6, or at least one CDR whose sequence has at least 80%, preferably 85%, 90%, 95% and 98% identity after optimal alignment with sequences SEQ ID No. 2, 4 or 6.

More particularly, the antibodies of the invention, or one of their derived compounds or functional fragments, are characterized in that they comprise a heavy chain comprising at least one of the three CDRs of the sequences SEQ ID Nos. 2, 4 and 6, or at least one sequence with at least 80%, preferably 85%, 90%, 95% and 98% identity after optimal alignment with sequences SEQ ID Nos. 2, 4 or 6.

Even more preferably, the antibodies of the invention, or one of their derived compounds or functional fragments, are characterized in that they comprise a heavy chain comprising the following three CDRs, respectively CDR-H1, CDR-H2 and CDR-H3, wherein:

CDR-H1 comprises the sequence SEQ ID No. 2, 7 or 9, or a sequence with at least 80% identity after optimal alignment with sequence SEQ ID No. 2, 7 or 9;

CDR-H2 comprises the sequences SEQ ID No. 4 or 11, or a sequence with at least 80% identity after optimal alignment with sequence SEQ ID No. 4 or 11; and CDR-H3 comprises the sequences SEQ ID No. 6 or 12, or a sequence with at least 80% identity after optimal alignment with sequence SEQ ID No. 6 or 12.

According to a particular embodiment, antibodies, or one of their derived compounds or functional fragments, are characterized in that they comprise a heavy chain comprising the CDR-H1 of the sequence SEQ ID No. 7, the CDR-H2 of the sequence SEQ ID No. 4 and the CDR-H3 of the sequence SEQ ID No. 12.

According to another particular embodiment, antibodies, or one of their derived compounds or functional fragments, are characterized in that they comprise a heavy chain comprising the CDR-H1 of the sequence SEQ ID No. 9, the CDR-H2 of the sequence SEQ ID No. 11 and the CDR-H3 of the sequence SEQ ID No. 6.

According to another embodiment, the antibodies of the invention, or one of their derived compounds or functional fragments, are characterized in that they comprise a light chain comprising at least one of the three CDRs of the sequences SEQ ID Nos. 1, 3 and 5, or at least one sequence with at least 80%, preferably 85%, 90%, 95% and 98% identity after optimal alignment with sequences SEQ ID Nos. 1, 3 or 5.

In a preferred manner, the antibodies of the invention, or one of their derived compounds or functional fragments, are characterized in that they comprise a light chain comprising the following three CDRs, respectively CDR-L1, CDR-L2 and CDR-L3, wherein:

CDR-L1 comprises the sequence SEQ ID No. 1 or 8, or a sequence with at least 80% identity after optimal alignment with sequence SEQ ID No. 1 or 8;

CDR-L2 comprises the sequences SEQ ID No. 3 or 10, or a sequence with at least 80% identity after optimal alignment with sequence SEQ ID No. 3 or 10; and CDR-L3 comprises the sequence SEQ ID No. 5, or a sequence with at least 80% identity after optimal alignment with sequence SEQ ID No. 5.

According to a particular embodiment, antibodies, or one of their derived compounds or functional fragments, are characterized in that they comprise a light chain comprising the CDR-L1 of the sequence SEQ ID No. 1, the CDR-L2 of the sequence SEQ ID No. 3 and the CDR-L3 of the sequence SEQ ID No. 5.

According to another particular embodiment, antibodies, or one of their derived compounds or functional fragments, are characterized in that they comprise a light chain comprising the CDR-L1 of the sequence SEQ ID No. 8, the CDR-L2 of the sequence SEQ ID No. 10 and the CDR-L3 of the sequence SEQ ID No. 5.

In the present description, the terms "polypeptides", "polypeptide sequences", "peptides" and "proteins attached to antibody compounds or to their sequences" are interchangeable.

It must be understood here that the invention does not relate to antibodies in natural form, i.e., they are not taken from their natural environment but are isolated or obtained by purification from natural sources or obtained by genetic recombination or chemical synthesis and thus they can carry unnatural amino acids as will be described below.

In a first embodiment, complementarity-determining region, or CDR, means the hypervariable regions of the heavy and light chains of immunoglobulins as defined by Kabat et al. (Kabat et al., Sequences of proteins of immunological interest, $5^{th}$ Ed., U.S. Department of Health and Human Services, NIH, 1991, and later editions). There are three heavy-chain CDRs and three light-chain CDRs. Here, the terms "CDR" and "CDRs" are used to indicate, depending on the case, one or more, or even all, of the regions containing the majority of the amino acid residues responsible for the antibody's binding affinity for the antigen or epitope it recognizes.

In a second embodiment, by CDR regions or CDR(s), it is intended to indicate the hypervariable regions of the heavy and light chains of the immunoglobulins as defined by IMGT.

The IMGT unique numbering has been defined to compare the variable domains whatever the antigen receptor, the chain type, or the species [Lefranc M.-P., Immunology Today 18, 509 (1997)/Lefranc M.-P., The Immunologist, 7, 132-136 (1999)/Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering, the conserved amino acids always have the same position, for instance cystein 23 (1st-CYS), tryptophan 41 (CONSERVED-TRP), hydrophobic amino acid 89, cystein 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown from brackets and separated by dots, e.g. [8.8.13]) become crucial information. The IMGT unique numbering is used in 2D graphical representations, designated as IMGT Colliers de Perles [Ruiz, M. and Lefranc, M.-P., Immunogenetics, 53, 857-883 (2002)/Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

Three heavy chain CDRs and 3 light chain CDRs exist. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

For more clarity, it must be understood that in the following description, and more particularly in table 2 and 3, the CDRs will be defined by IMGT numbering, kabat numbering and by common numbering.

Common numbering regroups the residues part of each CDR which are common to the CDRs as defined by the IMGT and the Kabat numbering systems.

IMGT numbering system defines the CDRs according to the IMGT system as above defined whereas kabat numbering system defines the CDRs according to the kabat system as above defined.

More particularly, CDR-L1 consist of SEQ ID No. 1 (QDINNY) in the common and IMGT numbering systems and of SEQ ID No. 8 (KASQDINNYIA) in the kabat numbering system.

Concerning the CDR-L2, it consists of SEQ ID No. 3 (YTS) in the common and IMGT numbering systems and of SEQ ID No. 10 (YTSTLQA) in the kabat numbering system.

The CDR-L3 consists of SEQ ID No. 5 (LQYDNLWT) for each of the three numbering systems.

For the heavy chain, the CDR-H1 consists of the SEQ ID No. 2 (TDYS) in the common numbering system, of SEQ ID No. 7 (GYSFTDYS) in the IMGT numbering system and of SEQ ID No. 9 (TDYSMY) in the kabat numbering system.

The CDR-H2 consists of SEQ ID No. 4 (IDPYNGGT) in the common and IMGT numbering systems and of SEQ ID No. 11 (YIDPYNGGTRYNQKFKG) in the kabat numbering system.

At last, the CDR-H3 consists in the SEQ ID No. 6 (QTDYFDY) in the common and kabat numbering systems whereas it consists of SEQ ID No. 12 (ARQTDYFDY) in the IMGT numbering system.

In the sense of the present invention, the "percentage identity" from two sequences of nucleic acids or amino acids means the percentage of identical nucleotides or amino acid residues from the two sequences to be compared, obtained after optimal alignment, this percentage being purely statistical and the differences from the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444] or by means of computer software using these algorithms (GAP, BESTFIT, FASTA and TFASTA in the Wisconsin Genetics Software Package, Genetics Computer Group, 575 Science Dr., Madison, Wis., or by the comparison software BLAST NR or BLAST P).

The percentage identity from two nucleic acid or amino acid sequences is determined by comparing the two optimally-aligned sequences in which the nucleic acid or amino acid sequence to compare can have additions or deletions compared to the reference sequence for optimal alignment from the two sequences. Percentage identity is calculated by determining the number of positions at which the amino acid nucleotide or residue is identical from the two sequences, dividing the number of identical positions by the total number of positions in the alignment window and multiplying the result by 100 to obtain the percentage identity from the two sequences.

For example, the BLAST program, "BLAST 2 sequences" (Tatusova et al., "Blast 2 sequences—a new tool for comparing protein and nucleotide sequences", FEMS Microbiol., 1999, Lett. 174:247-250), used with the default parameters (notably for the parameters "open gap penalty": 5, and "extension gap penalty": 2; the selected matrix being for example the "BLOSUM 62" matrix proposed by the program); the percentage identity from the two sequences to compare is calculated directly by the program.

For the amino acid sequence exhibiting at least 80%, preferably 85%, 90%, 95% and 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity from the various antibodies likely to be generated.

As a non-limiting example, table 1 below summarizes the possible substitutions likely to be carried out without resulting in a significant modification of the biological activity of the corresponding modified antibody; inverse substitutions are naturally possible under the same conditions.

TABLE 1

| Original residue | Substitution(s) |
| --- | --- |
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (G) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

It is known by those skilled in the art that in the current state of the art the greatest variability (length and composition) from the six CDRs is found at the three heavy-chain CDRs and, more particularly, at CDR-H3 of this heavy chain. Consequently, it will be evident that the preferred characteristic CDRs of the antibodies of the invention, or of one of their derived compounds or functional fragments, will be the three CDRs of the heavy chain, i.e., the CDRs coded by sequences SEQ ID Nos. 2, 4 and 6, respectively, and even more preferentially, the CDR corresponding to the CDR-H3 coded by sequence SEQ ID No. 6.

In a specific embodiment, the present invention relates to a murine antibody, or derived compounds or functional fragments of same.

Another embodiment of the invention discloses an antibody, or its derived compounds or functional fragments, comprising a light chain comprising the following three CDRs: CDR-L1 of the sequence SEQ ID No. 1 or of a sequence with at least 80%, preferably 85%, 90%, 95% and 98% identity after optimal alignment with sequence SEQ ID No. 1;

CDR-L2 of the sequence SEQ ID No. 3 or of a sequence with at least 80%, preferably 85%, 90%, 95% and 98% identity after optimal alignment with sequence SEQ ID No. 3; and CDR-L3 of the sequence SEQ ID No. 5 or of a sequence with at least 80%, preferably 85%, 90%, 95% and 98% identity after optimal alignment with sequence SEQ ID No. 5, and a heavy chain comprising the following three CDRs:

CDR-H1 of the sequence SEQ ID No. 7 or of a sequence with at least 80%, preferably 85%, 90%, 95% and 98% identity after optimal alignment with sequence SEQ ID No. 7;

CDR-H2 of the sequence SEQ ID No. 4 or of a sequence with at least 80%, preferably 85%, 90%, 95% and 98% identity after optimal alignment with sequence SEQ ID No. 4; and CDR-H3 of the sequence SEQ ID No. 12 or of a sequence with at least 80%, preferably 85%, 90%, 95% and 98% identity after optimal alignment with sequence SEQ ID No. 12.

Still another embodiment of the invention discloses an antibody, or a derived compound or functional fragment of same, comprising a light chain comprising the following three CDRs:

CDR-L1 of the sequence SEQ ID No. 8 or of a sequence with at least 80% identity after optimal alignment with sequence SEQ ID No. 8;

CDR-L2 of the sequence SEQ ID No. 10 or of a sequence with at least 80% identity after optimal alignment with sequence SEQ ID No. 10; and CDR-L3 of the sequence SEQ ID No. 5 or of a sequence with at least 80% identity after optimal alignment with sequence SEQ ID No. 5, and a heavy chain comprising the following three CDRs:

CDR-H1 of the sequence SEQ ID No. 9 or of a sequence with at least 80% identity after optimal alignment with sequence SEQ ID No. 9;

CDR-H2 of the sequence SEQ ID No. 11 or of a sequence with at least 80% identity after optimal alignment with sequence SEQ ID No. 11; and CDR-H3 of the sequence SEQ ID No. 6 or of a sequence with at least 80% identity after optimal alignment with sequence SEQ ID No. 6.

According to still another embodiment, the antibody of the invention, or its derived compounds or functional fragments, is characterized in that it comprises a light-chain sequence comprising the amino acid sequence SEQ ID No. 13 or a sequence with at least 80%, preferably 85%, 90%, 95% and 98% identity after optimal alignment with sequence SEQ ID No. 13; and in that it comprises a heavy-chain sequence comprising the amino acid sequence SEQ ID No. 14 or a sequence with at least 80%, preferably 85%, 90%, 95% and 98% identity after optimal alignment with sequence SEQ ID No. 14.

It is also disclosed a humanized antibody, or a derived compound or functional fragment of same, which is characterized in that it comprises a light chain sequence comprising the amino acid sequence SEQ ID No. 17 or a sequence with at least 80% identity after optimal alignment with sequence SEQ ID No. 17, and in that it comprises a heavy chain sequence comprising the amino acid sequence SEQ ID No. 18 or 19 or a sequence with at least 80% identity after optimal alignment with sequence SEQ ID No. 18 or 19.

As seen above, the invention also relates to any compound derived from an antibody as described in the invention.

More particularly, the antibody of the invention, or its derived compounds or functional fragments, is characterized in that said derived compound consists of a binding protein comprising a peptide scaffold on which is grafted at least one CDR in such a way as to preserve all or part of the paratope recognition properties of the initial antibody.

One or more sequences among the six CDR sequences described in the present invention can also be present on the various immunoglobulin protein scaffolding. In this case, the protein sequence makes it possible to recreate a peptide skeleton favorable to the folding of the grafted CDRs, enabling them to preserve their paratope antigen-recognition properties.

Generally, a person skilled in the art knows how to determine the type of protein scaffold on which to graft at least one of the CDRs arising from the original antibody. More particularly, it is known that to be selected such scaffolds must meet the greatest number of criteria as follows (Skerra A., J. Mol. Recogn., 2000, 13:167-187):

good phylogenetic conservation;

known three-dimensional structure (as, for example, by crystallography, NMR spectroscopy or any other technique known to a person skilled in the art);

small size;

few or no post-transcriptional modifications; and/or easy to produce, express and purify.

The origin of such protein scaffolds can be, but is not limited to, the structures selected among: fibronectin and preferentially fibronectin type III domain 10, lipocalin, anticalin (Skerra A., J. Biotechnol., 2001, 74(4):257-75), protein Z arising from domain B of protein A of *Staphylococcus aureus*, thioredoxin A or proteins with a repeated motif such as the "ankyrin repeat" (Kohl et al., PNAS, 2003, vol. 100, No. 4, 1700-1705), the "armadillo repeat", the "leucine-rich repeat" and the "tetratricopeptide repeat".

Scaffolds derived from toxins such as, for example, toxins from scorpions, insects, plants, mollusks, etc., and the protein inhibiters of neuronal NO synthase (PIN) should also be mentioned.

An example, in no way limiting, of such hybrid constructions, is the insertion of the CDR-H1 (heavy chain) of an anti-CD4 antibody, namely 13B8.2, in one of the loops in the PIN, the new binding protein thus obtained preserving the same binding properties as the original antibody (Bes et al., Biochem. Biophys. Res. Commun., 2006, 343(1), 334-344). On a purely illustrative basis, grafting the CDR-H3 (heavy chain) of an anti-lysozyme VHH antibody on one of the loops of neocarzinostatin (Nicaise et al., Protein Science, 2004, 13(7):1882-1891) can also be mentioned.

Lastly, as described above, such peptide scaffolds can comprise from one to six CDRs arising from the original antibody. Preferably, but not being a requirement, a person skilled in the art will select at least one CDR from the heavy chain, the latter being known to be primarily responsible for the specificity of the antibody. The selection of one or more relevant CDRs is obvious to a person skilled in the art, who will then choose suitable known techniques (Bes et al., FEBS letters 508, 2001, 67-74).

A specific aspect of the present invention relates to a method for selecting a compound derived from an antibody according to the invention, said derived compound being capable of inhibiting in vitro and/or in vivo the growth of tumor cells and said derived compound comprising a peptide scaffold on which is grafted at least one antibody CDR, characterized in that it comprises the following steps:

a) the placing in contact in vitro of a compound composed of a peptide scaffold on which is grafted at least one antibody CDR with a biological sample containing tumor cells able to grow and under conditions allowing these cells to grow; and b) selection of said compound If said compound is capable of inhibiting the growth of these tumor cells, and characterized in that said at least one grafted CDR is selected among the following CDRs:

the CDR of sequence SEQ ID No. 1, 8 or a sequence with at least 80%, preferably 85%, 90%, 95% and 98% identity after optimal alignment with sequence SEQ ID No. 1, 8;

the CDR of sequence SEQ ID No. 3, 10 or a sequence with at least 80%, preferably 85%, 90%, 95% and 98% identity after optimal alignment with sequence SEQ ID No. 3, 10;

the CDR of sequence SEQ ID No. 5 or a sequence with at least 80%, preferably 85%, 90%, 95% and 98% identity after optimal alignment with sequence SEQ ID No. 5;

the CDR of sequence SEQ ID No. 2, 7, 9 or a sequence with at least 80%, preferably 85%, 90%, 95% and 98% identity after optimal alignment with sequence SEQ ID No. 2, 7, 9;

the CDR of sequence SEQ ID No. 4, 11 or a sequence with at least 80%, preferably 85%, 90%, 95% and 98% identity after optimal alignment with sequence SEQ ID No. 4, 11; and the CDR of sequence SEQ ID No. 6, 12 or a sequence with at least 80%, preferably 85%, 90%, 95% and 98% identity after optimal alignment with sequence SEQ ID No. 6, 12.

According to a preferred mode, the method can include in step a) the placing in contact in vitro of a compound comprising a peptide scaffold on which is grafted at least two or three antibody CDRs.

According to an even more preferred mode of this method, the peptide scaffold is selected among the scaffolds or binding proteins whose structures were mentioned above.

Obviously, these examples are in no way limiting, and any other structure known or obvious to a person skilled in the art should be considered as being covered by the protection conferred by the present patent application.

The present invention thus relates to an antibody, or its derived compounds or functional fragments, characterized in that the peptide scaffold is selected among proteins that are a) phylogenetically well preserved, b) of robust architecture, c) with a well-known 3-D molecular organization, d) of small size and/or e) comprising regions that can be modified by deletion and/or insertion without modifying stability properties.

According to a preferred embodiment, the antibody of the invention, or its derived compounds or functional fragments, is characterized in that said peptide scaffold is selected among i) scaffolds arising from fibronectin, preferentially fibronectin type 3 domain 10, lipocalin, anticalin, protein Z arising from domain B of protein A of *Staphylococcus aureus*, thioredoxin A or proteins with a repeated motif such as the "ankyrin repeat" (Kohl et al., PNAS, 2003, vol. 100, No. 4, 1700-1705), the "armadillo repeat", the "leucine-rich repeat" and the "tetratricopeptide repeat" or iii) protein inhibiters of neuronal NO synthase (PIN).

Another aspect of the invention relates to the functional fragments of the antibody described above.

More particularly, the invention targets an antibody, or its derived compounds or functional fragments, characterized in that said functional fragment is selected among the fragments Fv, Fab, (Fab')$_2$, Fab', scFv, scFv-Fc and diabodies, or any fragment whose half-life has been increased such as PEGylated fragments.

Such functional fragments of the antibody according to the invention consist, for example, of the fragments Fv, scFv (sc=simple chain), Fab, F(ab')$_2$, Fab', scFv-Fc or diabodies, or any fragment whose half-life has been increased by chemical modification, such as the addition of polyalkylene glycol such as polyethylene glycol (PEGylation) (PEGylated fragments are referred to as Fv-PEG, scFv-PEG, Fab-PEG, F(ab')$_2$-PEG and Fab'-PEG), or by incorporation in a liposome, microspheres or PLGA, said fragments possessing at least one of the characteristic CDRs of the invention which is notably capable of exerting in a general manner activity, even partial, of the antibody from which it arises.

Preferably, said functional fragments will comprise or include a partial sequence of the variable heavy or light chain of the antibody from which they are derived, said partial sequence being sufficient to retain the same binding specificity as the antibody from which it arises and sufficient affinity, preferably at least equal to 1/100, more preferably at least 1/10 of that of the antibody from which it arises.

Such a functional fragment will contain at least five amino acids, preferably 6, 7, 8, 10, 15, 25, 50 or 100 consecutive amino acids of the sequence of the antibody from which it arises.

Preferably, these functional fragments will be of the types Fv, scFv, Fab, F(ab')$_2$, F(ab'), scFv-Fc or diabodies, which generally have the same binding specificity as the antibody from which they result. According to the present invention, fragments of the antibody of the invention can be obtained from the antibodies described above by methods such as enzyme digestion, including pepsin or papain, and/or by cleavage of the disulfide bridges by chemical reduction. The antibody fragments can be also obtained by recombinant genetics techniques also known to a person skilled in the art or by peptide synthesis by means, for example, of automatic peptide synthesizers such as those marketed by Applied Bio-Systems, etc.

The invention also targets the original murine antibody, namely an antibody according to the invention, or its derived compounds or functional fragments, characterized in that said antibody is a murine antibody and in that it comprises a light-chain of amino acid sequence SEQ ID No. 15, or a sequence with at least 80%, preferably 85%, 90%, 95% and 98% identity after optimal alignment with sequence SEQ ID No. 15, and a heavy-chain of amino acid sequence SEQ ID No. 16, or a sequence with at least 80%, preferably 85%, 90%, 95% and 98% identity after optimal alignment with sequence SEQ ID No. 16.

For more clarity, table 2 below summarizes the various amino acid sequences corresponding to the antibody of the invention.

TABLE 2

(wherein Mu. = murine and Hu. = humanized):

| Antibody | CDR numbering | Heavy chain | Light chain | SEQ ID NO. |
|---|---|---|---|---|
| 6F4 | Common | | CDR-L1 | 1 |
| | | | CDR-L2 | 3 |
| | | | CDR-L3 | 5 |
| | | CDR-H1 | | 2 |
| | | CDR-H2 | | 4 |
| | | CDR-H3 | | 6 |
| | IMGT | | CDR-L1 | 1 |
| | | | CDR-L2 | 3 |
| | | | CDR-L3 | 5 |
| | | CDR-H1 | | 7 |
| | | CDR-H2 | | 4 |
| | | CDR-H3 | | 12 |
| | Kabat | | CDR-L1 | 8 |
| | | | CDR-L2 | 10 |
| | | | CDR-L3 | 5 |
| | | CDR-H1 | | 9 |
| | | CDR-H2 | | 11 |
| | | CDR-H3 | | 6 |
| | | | Mu. variable domain | 13 |

TABLE 2-continued (wherein Mu. = murine and Hu. = humanized):

| Antibody | CDR numbering | Heavy chain | Light chain | SEQ ID NO. |
|---|---|---|---|---|
| | | Mu. variable domain | | 14 |
| | | | Mu. entire | 15 |
| | | Mu. entire | | 16 |
| | | | Hu. variable domain | 17 |
| | | | Hu. variable domain (V1) | 18 |
| | | | Hu. variable domain (V2) | 19 |

Another specific aspect of the present invention relates to a chimeric antibody, or its derived compounds or functional fragments, characterized in that said antibody also comprises light-chain and heavy-chain constant regions derived from an antibody of a species heterologous with the mouse, notably man.

Yet another specific aspect of the present invention relates to a humanized antibody, or its derived compounds or functional fragments, characterized in that the constant regions of the light-chain and the heavy-chain derived from human antibody are, respectively, the lambda or kappa region and the gamma-1, gamma-2 or gamma-4 region.

According to another aspect, the invention relates to a murine hybridoma capable of secreting a monoclonal antibody according to the invention, notably the hybridoma of murine origin filed with the French center for microorganism cultures (CNCM, Pasteur Institute, Paris, France) on Jul. 6, 2006, under number 1-3646. Said hybridoma was obtained by the fusion of Balb/C immunized mice splenocytes and cells of the myeloma Sp 2/O—Ag 14 lines.

The monoclonal antibody, here referred to as 6F4, or its derived compounds or functional fragments, characterized in that said antibody is secreted by the hybridoma filed with the CNCM on Jul. 4, 2006, under number 1-3646, obviously forms part of the present invention.

The antibody of the invention also comprises chimeric or humanized antibodies.

A chimeric antibody is one containing a natural variable region (light chain and heavy chain) derived from an antibody of a given species in combination with constant regions of the light chain and the heavy chain of an antibody of a species heterologous to said given species.

The antibodies, or chimeric fragments of same, can be prepared by using the techniques of recombinant genetics. For example, the chimeric antibody could be produced by cloning recombinant DNA containing a promoter and a sequence coding for the variable region of a nonhuman monoclonal antibody of the invention, notably murine, and a sequence coding for the human antibody constant region. A chimeric antibody according to the invention coded by one such recombinant gene could be, for example, a mouse-human chimera, the specificity of this antibody being determined by the variable region derived from the murine DNA and its isotype determined by the constant region derived from human DNA. Refer to Verhoeyn et al. (BioEssays, 8:74, 1988) for methods for preparing chimeric antibodies.

"Humanized antibodies" means an antibody that contains CDR regions derived from an antibody of nonhuman origin, the other parts of the antibody molecule being derived from one (or several) human antibodies. In addition, some of the skeleton segment residues (called FR) can be modified to preserve binding affinity (Jones et al., Nature, 321:522-525, 1986; Verhoeyen et al., Science, 239:1534-1536, 1988; Riechmann et al., Nature, 332:323-327, 1988).

The humanized antibodies of the invention or fragments of same can be prepared by techniques known to a person skilled in the art (such as, for example, those described in the documents Singer et al., J. Immun., 150:2844-2857, 1992; Mountain et al., Biotechnol. Genet. Eng. Rev., 10:1-142, 1992; and Bebbington et al., Bio/Technology, 10:169-175, 1992). Such humanized antibodies are preferred for their use in methods involving in vitro diagnoses or preventive and/or therapeutic treatment in vivo. Other humanization techniques, also known to a person skilled in the art, such as, for example, the "CDR grafting" technique described by PDL in patents EP 0 451 261, EP 0 682 040, EP 0 939 127, EP 0 566 647 or U.S. Pat. No. 5,530,101, U.S. Pat. No. 6,180,370, U.S. Pat. No. 5,585,089 and U.S. Pat. No. 5,693,761. U.S. Pat. No. 5,639, 641 or 6,054,297, 5,886,152 and 5,877,293 can also be cited.

In addition, the invention also relates to humanized antibodies arising from the murine antibodies described above.

More particularly, the humanization method for the 6F4 antibody is described in detail in examples 2 and 3 for the light and heavy chains, respectively.

In a preferred manner, constant regions of the light-chain and the heavy-chain derived from human antibody are, respectively, the lambda or kappa and the gamma-1, gamma-2 or gamma-4 region.

In the embodiment corresponding to IgG1 isotype IgG1, an additional characteristic of the antibody is to exhibit effector functions, such as antibody-dependant cellular cytotoxicity (ADCC) and/or complement dependant cytotoxicity (CDC).

In the field of the present invention, several backup humanized antibodies have been developed. More particularly, the invention concerns two variants heavy chains and two variants light chains, both derived from the 6F4 antibody.

In a first aspect, the invention relates to a humanized antibody, or a derived compound or functional fragment thereof, said antibody being characterized in that it comprises a heavy chain variable domain, called BU-H1, comprising the amino acid sequence SEQ ID No. 65.

SEQ ID No. 65:
(X01)VQL(X02)QSGAEVKKPGASVKVSCKASGYSFTDYSMHWVRQAPG

Q(X03)LEWMG(X04)IDPYNGGT(X05)YSQKFQGR(X06)T(X07)T (X08)DTSASTAYM(X09)LSSLRSEDTAVYYCARQTDYFDYWGQGTLVT

VSS wherein bolded residues correspond to CDR-IMGT,
and X01 is E or Q; X02 is V or Q; X03 is S or R; X04 is Y or W; X05 is R or K; X06 is A or V; X07 is L or I; X08 is V or R and X09 is H or E.

In a second aspect, the invention relates to a humanized antibody, or a derived compound or functional fragment thereof, said antibody being characterized in that it comprises a heavy chain variable domain, called BU-H2, comprising the amino acid sequence SEQ ID No. 66.

SEQ ID No. 66:
(X01)VQL(X02)QSGAEVKKPGASVKVSCKASGYSFTDYSMHWVRQAPG

Q(X03)LEWMG(X04)IDPYNGGT(X05)YAQKFQGR(X06)T(X07)T (X08)DTSTSTVYM(X09)LSSLRSEDTAVYYCARQTDYFDYWGQGTLVT

VSS wherein bolded residues correspond to CDR-IMGT,
and X01 is E or Q; X02 is V or Q; X03 is S or G; X04 is Y or I; X05 is R or S; X06 is A or V; X07 is L or M; X08 is V or R and X09 is H or E.

In a third aspect, the invention relates to a humanized antibody, or a derived compound or functional fragment thereof, said antibody being characterized in that it comprises a light chain variable domain, called BU-L1, comprising the amino acid sequence SEQ ID No. 67.

SEQ ID No. 67:
DIQMTQSPSSLSASVGDRVTITC(X01)ASQDINNY(X02)AWYQQKPGK

VPKLLI(X03)YTSTLQSGVPSRFSGSGSGTD(X04)TLTISSLQPEDVA

TYYCLQYDNLWTFGQGTKVEIK wherein bolded residues correspond to CDR-IMGT,
and X01 is K or R; X02 is L or I; X03 is H or Y and X04 is Y or F.

In a fourth aspect, the invention relates to a humanized antibody, or a derived compound or functional fragment thereof, said antibody being characterized in that it comprises a light chain variable domain, called BU-L2, comprising the amino acid sequence SEQ ID No. 68.

SEQ ID No. 68:
(X01)I(X02)MTQSPFSLSASVGDRVTITC(X03)ASQDINNY(X04)A

WYQQKPAKAPKLFI(X05)YTS(X06)LQSGVPSRFSGSGSGTDYTLTIS

SLQPEDFATYYCLQYDNLWTFGQGTKVEIK wherein bolded residues correspond to CDR-IMGT,
and X01 is D or A; X02 is R or Q; X03 is K or W; X04 is L or I; X05 is H or Y and X06 is S or T.

In a preferred embodiment, the invention relates to a humanized antibody, or a derived compound or functional fragment thereof, characterized in that it comprises a heavy chain variable domain comprising the amino acid sequences SEQ ID No. 65 and a light chain variable domain comprising the amino acid sequence SEQ ID No. 67.

In another preferred embodiment, the invention relates to a humanized antibody, or a derived compound or functional fragment thereof, characterized in that it comprises a heavy chain variable domain comprising the amino acid sequences SEQ ID No. 65 and a light chain variable domain comprising the amino acid SEQ ID No. 68.

In yet another preferred embodiment, the invention relates to a humanized antibody, or a derived compound or functional fragment thereof, characterized in that it comprises a heavy chain variable domain comprising the amino acid sequences SEQ ID No. 66 and a light chain variable domain comprising the amino acid sequence SEQ ID No. 67.

Still in another preferred embodiment, the invention relates to a humanized antibody, or a derived compound or functional fragment thereof, characterized in that it comprises a heavy chain variable domain comprising the amino acid sequences SEQ ID No. 66 and a light chain variable domain comprising the amino acid sequence SEQ ID No. 68.

For more clarity, table 3 below summarizes the various amino acid sequences corresponding to the back-up antibodies.

TABLE 3

| Antibody | CDR numbering | Heavy chain | Light chain | SEQ ID NO. |
|---|---|---|---|---|
| 6F4 BU | | Hu. variable domain (H1) | | 65 |
| | | Hu. variable domain (H2) | | 66 |
| | | | Hu. variable domain (L1) | 67 |
| | | | Hu. variable domain (L2) | 68 |

(wherein Mu. = murine and Hu. = humanized):

In another aspect of the invention, the applicant has also identified the antigen recognized by the antibody according to the invention.

The method used to accomplish this is described in detail in example 4 below.

JAM-A is a membrane protein belonging to the immunoglobulin superfamily (IgSF), in which it belongs to the junctional adhesion molecule (JAM) family. In man, the JAM family comprises several members, including the JAM-A, JAM-B, JAM-C, A33 and A34 proteins. Among the members of the JAM family, JAM-A has the highest homology with JAM-B and JAM-C, approximately 35% sequence identity in amino acids and 45% similarity with these two proteins. JAM-A protein is also called JAM A, F11R, F11 receptor, JAM-1, JAM 1, PAM-1 or CD321.

Two isoforms of the JAM-A precursor differing by the length of the extracellular region were identified:
isoform a: 299 amino acids (SEQ ID No. 61)
isoform b: 259 amino acids (SEQ ID No. 63).

The nucleotide sequences of the two isoforms are represented with SEQ ID No. 62 for isoform a and SEQ ID No. 64 for isoform b.

The protein expressed on the surface of the human cells has a single polypeptide chain with an intracellular C-terminal domain, a single transmembrane domain (21 amino acids) and an N-terminal extracellular region containing two "Ig-like" domains.

JAM-A has an N-glycosylation site, an Asn residue in position 185 for isoform a and 145 for isoform b, and two disulfide bridges, one from Cys residues 50 and 109 in the Ig N-terminal domain and one from residues Cys 153 and 212 in the second Ig domain.

The presence of the two extracellular Ig-like domains was confirmed by crystallography (Kostrewa et al., 2001, EMBO J. 16:4391-4398; Prota et al., 2003, Proc. Natl. Acad. Sci. USA, 100:5366-5371). These two domains are connected by a tripeptide linker (sequence VLV [127-129], isoform A). These structural studies also confirmed the implication of JAM-A in homophilic interactions on the cell surface involving the extracellular region; this region, produced in recombinant form and capable of forming homodimers in solution (Bazzoni et al., 2000, J. Biol. Chem. 275:30970-30976) also made it possible to identify the amino acids involved in these interactions: Arg 59, Glu 61, Lys 63, Leu 72, Tyr 75, Met 110, Glu 114, Tyr 119 and Glu 121. The tripeptide RVE [59-61] is relatively conserved within the JAM family (RLE for JAM-B, RIE for JAM-C) and constitutes the minimal motif for homodimer formation (Kostrewa et al., 2001, EMBO J. 16:4391-4398).

In epithelial and endothelial cells, JAM-A is mainly found in the tight junctions (Liu et al., 2000, J. Cell Sci., 113:2363-2374). The cytoplasmic region contains a type II PDZ domain in the C-terminal position (sequence FLV [298-300], isoform a, which is responsible for the interaction of JAM-A with various cytosolic proteins associated with the tight junction, also containing a PDZ domain, such as ZO-1, AF-6, MUPP-1 and PAR-3 (Ebnet et al., 2000, J. Biol. Chem., 275:27979-27988; Itoh et al., 2001, J. Cell Biol., 154:491-498; Hamazaki et al., 2002, J. Biol. Chem., 277:455-461). Murine antibodies directed against the region [111-123] involved in dimer formation, so-called J3F.1 and J10.4 antibodies, are capable of inhibiting the homodimerization of JAM-A and the reconstruction of the epithelial barrier in vitro (Mandell et al., 2004, J. Biol. Chem., 279:16254-16262).

JAM-A interacts with integrin $\alpha_v\beta_3$ and is involved in the migration of endothelial cells on vitronectin, ligand of integrin $\alpha_v\beta_3$ (Naik and Naik, 2005, J. Cell Sci. 119:490-499). AntiJAM-A antibody J3F.1, in the same manner as an anti-$\alpha_v\beta_3$ antibody, inhibits the migration of endothelial cells and the angiogenesis induced by bFGF in vitro (Naik et al., 2003, Blood, 102:2108-2114). Various signaling pathways were demonstrated in endothelial cells: MAP kinases, PI3-kinase and PKC (Naik et Naik, 2005, J. Cell Sci., 119:490-499; Naik et al., 2003, Blood, 102:2108-2114; Naik et al., 2003, Arterioscler. Thromb. Vasc. Biol., 23:2165-2171).

JAM-A is also expressed in monocytes, lymphocytes, neutrophils and platelets (Williams et al., 1999, Mol. Immunol., 36:1175-1188). JAM-A protein was however initially identified as a receptor of the F11 antibody, an antibody capable of activating platelets and inducing their aggregation (Naik et al., 1995, Biochem. J., 310:155-162; Sobocka et al., 2000, Blood, 95:2600-2609). Peptides [28-60] and [97-109] belong to the F11 antibody epitope and are involved in platelet activation and aggregation phenomena and in homodimerization (Babinska et al., 2002, Thromb. Haemost., 87:712-721).

Rat antibody BV11, directed against the murine form of JAM-A, inhibits the trans-endothelial migration of monocytes in vitro and in vivo (Del Maschio et al., 1999, J. Exp. Med., 190:1351-1356). Ostermann and colleagues (2002, Nature Immunol., 3:151-158) showed that JAM-A was a ligand of $\alpha_L\beta_2$ or LFA-1 (lymphocyte function-associated antigen 1) integrin, which is overexpressed in response to certain chemokines during the development of an anti-inflammatory response and is required for the diapedesis or migration of leukocytes to the site of inflammation. JAM-A, via the second Ig-like domain, contributes to the adhesion and trans-endothelial migration of T lymphocytes and neutrophils (Ostermann et al., 2002, Nature Immunol., 3:151-158), and thus plays an important role in the recruitment of leukocytes to the site of inflammation.

JAM-A protein is also implicated in viral infection phenomena. JAM-A is indeed a receptor of reovirus, viruses responsible for certain types of encephalitis by means of interacting with attachment protein al (Barton et al., 2001, Cell 104:441-451). AntiJAM-A antibody J10.4 inhibits the binding of reovirus to JAM-A (Forrest et al., 2003, J. Biol. Chem., 278:48434-48444).

To date, none of the antibodies mentioned above directed against the human form of JAM-A exhibit activity in vivo, much less anti-tumor activity. Such antibodies are used only as research tools. Thus, in the former art, there is a genuine lack of an anti-tumor antibody active in vitro and in vivo.

According to a specific aspect, the antibody of the invention, or its derived compounds or functional fragments, is characterized in that it is capable of specifically binding to JAM-A protein (according to the English nomenclature "Junctional Adhesion Molecules").

According to still another aspect, the antibody of the invention, or its derived compounds or functional fragments, is characterized in that it exhibits a $K_D$ for JAM-A from roughly 1 nM and roughly 1 pM. More preferably, said $K_D$ for JAM-A is from roughly 10 pM and roughly 40 pM.

The expression "$K_D$" refers to the dissociation constant of a given antibody-antigen complex. $K_D=K_{off}/K_{on}$ with $K_{off}$ consisting of the "off rate" constant for the dissociation of the antibody from the antibody-antigen complex and $K_{on}$ consisting of the level at which the antibody binds the antigen (Chen Y. et al., 1999, J. Mol. Biol., 293:865-881).

A novel aspect of the present invention relates to an isolated nucleic acid characterized in that it is selected among the following nucleic acids (including any degenerate genetic code):

a) a nucleic acid, DNA or RNA, coding for an antibody according to the invention, or one of its derived compounds or functional fragments;

b) a nucleic acid complementary to a nucleic acid as defined in a);

c) a nucleic acid of at least 18 nucleotides capable of hybridizing under highly stringent conditions with at least one of the CDRs of nucleic acid sequences SEQ ID Nos. 20 to 31 or with a sequence with at least 80%, preferably 85%, 90%, 95% and 98%, identity after optimal alignment with sequence SEQ ID Nos. 20 to 31; and d) a nucleic acid of at least 18 nucleotides capable of hybridizing under highly stringent conditions with at least the light chain of nucleic acid sequence SEQ ID No. 32 or 36 and/or the heavy chain of nucleic acid sequence SEQ ID No. 33, 37 or 38, or with a sequence with at least 80% identity after optimal alignment with sequence SEQ ID No. 32 or 36 and/or 33, 37 or 38.

Table 4 below summarizes the various nucleotide sequences concerning the antibody of the invention.

TABLE 4

| Antibody | CDR numbering | Heavy chain | Light chain | SEQ ID NO. |
|---|---|---|---|---|
| 6F4 | Common | | CDR-L1 | 20 |
| | | | CDR-L2 | 22 |
| | | | CDR-L3 | 24 |
| | | CDR-H1 | | 21 |
| | | CDR-H2 | | 23 |
| | | CDR-H3 | | 25 |
| | IMGT | | CDR-L1 | 20 |
| | | | CDR-L2 | 22 |
| | | | CDR-L3 | 24 |
| | | CDR-H1 | | 26 |
| | | CDR-H2 | | 23 |
| | | CDR-H3 | | 27 |
| | Kabat | | CDR-L1 | 28 |
| | | | CDR-L2 | 29 |
| | | | CDR-L3 | 24 |
| | | CDR-H1 | | 30 |
| | | CDR-H2 | | 31 |
| | | CDR-H3 | | 25 |
| | | | Mu. variable domain | 32 |
| | | Mu. variable domain | | 33 |
| | | | Mu. entire | 34 |
| | | Mu. entire | | 35 |
| | | | Hu. variable domain | 36 |
| | | Hu. variable domain (V1) | | 37 |
| | | Hu. variable domain (V2) | | 38 |

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, defining a fragment or a region of a nucleic acid, containing unnatural nucleotides or not, and being either a double-strand DNA, a single-strand DNA or transcription products of said DNAs.

It should also be included here that the present invention does not relate to nucleotide sequences in their natural chromosomal environment, i.e., in a natural state. The sequences of the present invention have been isolated and/or purified, i.e., they were sampled directly or indirectly, for example by a copy, their environment having been at least partially modified. Isolated nucleic acids obtained by recombinant genetics, by means, for example, of host cells, or obtained by chemical synthesis should also be mentioned here.

"Nucleic sequences exhibiting a percentage identity of at least 80%, preferably 85%, 90%, 95% and 98%, after optimal alignment with a preferred sequence" means nucleic sequences exhibiting, with respect to the reference nucleic sequence, certain modifications such as, in particular, a deletion, a truncation, an extension, a chimeric fusion and/or a substitution, notably punctual. Preferably, these are sequences which code for the same amino acid sequences as the reference sequence, this being related to the degeneration of the genetic code, or complementarity sequences that are likely to hybridize specifically with the reference sequences, preferably under highly stringent conditions, notably those defined below.

Hybridization under highly stringent conditions means that conditions related to temperature and ionic strength are selected in such a way that they allow hybridization to be maintained from two complementarity DNA fragments. On a purely illustrative basis, the highly stringent conditions of the hybridization step for the purpose of defining the polynucleotide fragments described above are advantageously as follows.

DNA-DNA or DNA-RNA hybridization is carried out in two steps: (1) prehybridization at 42° C. for three hours in phosphate buffer (20 mM, pH 7.5) containing 5×SSC (1×SSC corresponds to a solution of 0.15 M NaCl+0.015 M sodium citrate), 50% formamide, 7% sodium dodecyl sulfate (SDS), 10×Denhardt's, 5% dextran sulfate and 1% salmon sperm DNA; (2) primary hybridization for 20 hours at a temperature depending on the length of the probe (i.e.: 42° C. for a probe >100 nucleotides in length) followed by two 20-minute washings at 20° C. in 2×SSC+2% SDS, one 20-minute washing at 20° C. in 0.1×SSC+0.1% SDS. The last washing is carried out in 0.1×SSC+0.1% SDS for 30 minutes at 60° C. for a probe >100 nucleotides in length. The highly stringent hybridization conditions described above for a polynucleotide of defined size can be adapted by a person skilled in the art for longer or shorter oligonucleotides, according to the procedures described in Sambrook, et al. (Molecular cloning: a laboratory manual, Cold Spring Harbor Laboratory; 3rd edition, 2001).

The invention also relates to a vector comprising anucleic acid as described in the invention.

The invention notably targets cloning and/or expression vectors that contain such a nucleotide sequence.

The vectors of the invention preferably contain elements which allow the expression and/or the secretion of nucleotide sequences in a given host cell. The vector thus must contain a promoter, translation initiation and termination signals, as well as suitable transcription regulation regions. It must be able to be maintained in a stable manner in the host cell and may optionally have specific signals which specify secretion of the translated protein. These various elements are selected and optimized by a person skilled in the art according to the host cell used. For this purpose, the nucleotide sequences can be inserted in self-replicating vectors within the selected host or be integrative vectors of the selected host.

Such vectors are prepared by methods typically used by a person skilled in the art and the resulting clones can be introduced into a suitable host by standard methods such as lipofection, electroporation, heat shock or chemical methods.

The vectors are, for example, vectors of plasmid or viral origin. They are used to transform host cells in order to clone or express the nucleotide sequences of the invention.

The invention also comprises host cells transformed by or comprising a vector as described in the present invention.

The host cell can be selected among prokaryotic or eukaryotic systems such as bacterial cells, for example, but also yeast cells or animal cells, notably mammal cells. Insect or plant cells can also be used.

The invention also relates to animals, other than man, that have a transformed cell according to the invention.

Another aspect of the invention relates to a method for the production of an antibody according to the invention, or one of its functional fragments, characterized in that said method comprises the following steps:

a) the culture in a medium of and the suitable culture conditions for a host cell according to the invention; and b) the recovery of said antibody, or one of its functional fragments, thus produced from the culture medium or from said cultured cells.

The transformed cells according to the invention are of use in methods for the preparation of recombinant polypeptides according to the invention. Methods for the preparation of polypeptide according to the invention in recombinant form, characterized in that said methods use a vector and/or a cell transformed by a vector according to the invention, are also comprised in the present invention. Preferably, a cell transformed by an vector according to the invention is cultured under conditions that allow the expression of the aforesaid polypeptide and recovery of said recombinant peptide.

As already mentioned, the host cell can be selected among prokaryotic or eukaryotic systems. In particular, it is possible to identify the nucleotide sequences of the invention that facilitate secretion in such a prokaryotic or eukaryotic system. An vector according to the invention carrying such a sequence can thus be used advantageously for the production of recombinant proteins to be secreted. Indeed, the purification of these recombinant proteins of interest will be facilitated by the fact that they are present in the supernatant of the cellular culture rather than inside host cells.

The polypeptides of the invention can also be prepared by chemical synthesis. One such method of preparation is also an object of the invention. A person skilled in the art knows methods for chemical synthesis, such as solid-phase techniques (see notably Steward et al., 1984, Solid phase peptides synthesis, Pierce Chem. Company, Rockford, 111, 2nd ed.) or partial solid-phase techniques, by condensation of fragments or by conventional synthesis in solution. Polypeptides obtained by chemical synthesis and capable of containing corresponding unnatural amino acids are also comprised in the invention.

The antibodies, or the derived compounds or functional fragments of same, likely to be obtained by the method of the invention are also comprised in the present invention.

According to still another aspect, the present invention relates to an antibody as described above, characterized in that it is, in addition, capable of specifically binding to a human tyrosine kinase family receptor and/or capable of specifically inhibiting the tyrosine kinase activity of such a receptor.

According to a novel embodiment, the invention relates to an antibody, or its derived compounds or functional fragments, consisting of an antibody that is bispecific in the sense that it comprises a second motif capable of interacting with any receptor implicated in the development of tumors, such as, for example, VEGFR, VEGF, EGFR, IGF-1R, HER2neu, HGF, cMET, FGF, tetraspanins, integrins, CXCR4 or CXCR2.

According to a first embodiment, one such antibody consists of a bispecific antibody and comprises a second motif that specifically inhibits the binding of EGF with human epidermal growth factor receptor (EGFR) and/or specifically inhibiting the tyrosine kinase activity of said EGFR. According to an even more preferred aspect of the invention, said second anti-EGFR motif arises from the monoclonal antibody cetuximab (C225 or erbitux), matuzumab, huR3, HuMax-EGFR or panitumab.

According to a second embodiment, the antibody according to the invention consists of a bispecific antibody and comprises a second motif specifically inhibiting the activity modulated by the HER2/neu receptor and/or specifically inhibiting the tyrosine kinase activity of said HER2/neu receptor. More particularly, said second antiHER2/neu motif arises from the mouse monoclonal antibody 4D5 or 2C4 or from the humanized antibody trastuzumab or pertuzumab.

According to a third embodiment, the antibody according to the invention consists of a bispecific antibody and comprises a second motif specifically inhibiting the binding of hepatocyte growth factor (HGF) with the cMET receptor and/or specifically inhibiting the tyrosine kinase activity of said cMET receptor.

According to a fourth embodiment, the antibody according to the invention consists of a bispecific antibody and comprises a second motif specifically inhibiting the activity modulated by the IGF-1R receptor and/or specifically inhibiting the tyrosine kinase activity of said IGF-1R receptor. More particularly, said second antiIGF-1R motif arises from mouse monoclonal antibody 7C10, from corresponding humanized antibody h7C10 (Goetsch et al., international patent application WO 03/059951), from hEM164 antibodies (Maloney et al., Cancer Res., 2003, 63 (16):5073-5083), from the antiIGF-1R antibodies developed by Abgenix (see US patent application 2005/281812) or from Mab 39, 1H7 (Li et al., Cancer Immunol. Immunother., 2000, 49(4-5):243-252) or 4G11 (Jackson-Booth et al., Horm. Metab. Res., 2003, 35(11-12):850-856).

Lastly, according to a final embodiment, the antibody of the invention consists in a bispecific antibody and comprises a second motif capable of interacting with any type of receptor implicated in tumor development, such as, as non-limiting examples, VEGFR, VEGF, FGF (fibroblast growth factor) or any member of the CXCR (chemokine receptor) family, such as CXCR2 or CXCR4.

Also suitable for mention are antiCD20 antibodies such as a rituximab, ibritumomab or tositumomab; antiCD33 antibodies such as gemtuzumab or lintuzumab; antiCD22 antibodies such as epratuzumab; antiCD52 antibodies such as alemtuzumab; antiEpCAM antibodies such as edrecolomab, Ch 17-1A or IGN-101; antiCTP21 or 16 antibodies such as Xactin; antiDNA-Ag antibodies such as $^{131}$I-Cotara TNT-1; antiMUC1 antibodies such as pemtumomab or R1150; antiMUC18 antibodies such as ABX-MA1; antiGD3 antibodies such as mitumomab; anti ECA antibodies such as CeaVac or labetuzumab; antiCA125 antibodies such as OvaRex; antiHLA-DR antibodies such as apolizumab; antiCTLA4 antibodies such as MDX-010; antiPSMA antibodies such as MDX-070, $^{111}$In & $^{90}$Y-J591, $^{177}$Lu J591, J591-DM1; antiLewis Y antibodies such as IGN311; antiangiogenesis antibodies such as AS1405 and 90YmuBC1; antiTrail-R1 antibodies such as TRAIL R1mAb or TRAIL R2mAb.

The bispecific or bifunctional antibodies constitute a second generation of monoclonal antibodies in which two different variable regions are combined in the same molecule (Hollinger and Bohlen, 1999, Cancer and metastasis, rev. 18:411-419). Their utility was demonstrated in both diagnostic and therapeutic domains relative to their capacity to recruit new effector functions or to target several molecules on the surface of tumor cells; such antibodies can be obtained by chemical methods (Glennie M J et al., 1987, J. Immunol. 139, 2367-2375; Repp R. et al., 1995, J. Hemat., 377-382) or somatic methods (Staerz U. D. and Bevan M. J., 1986, PNAS 83, 1453-1457; Suresh M. R. et al., 1986, Method Enzymol., 121:210-228) but also, preferentially, by genetic engineering techniques that make it possible to force heterodimerization and thus facilitate the purification of the antibody sought (Merchand et al., 1998, Nature Biotech., 16:677-681).

These bispecific antibodies can be constructed as whole IgG, bispecific Fab'2, Fab'PEG, diabodies or bispecific scFv, but also as a tetravalent bispecific antibody in which two binding sites are present for each antigen targeted (Park et al., 2000, Mol. Immunol., 37(18):1123-30) or the fragments of same as described above.

In addition to an economic advantage given that the production and administration of a bispecific antibody are cheaper than the production of two specific antibodies, the use of such bispecific antibodies has the advantage of reducing the treatment's toxicity. Indeed, the use of a bispecific antibody makes it possible to decrease the overall quantity of circulating antibodies and, consequently, possible toxicity.

In a preferred embodiment of the invention, the bispecific antibody is a bivalent or tetravalent antibody.

Lastly, the present invention relates to the antibody described above, or its derived compounds or functional fragments, for use as a drug.

The invention also relates to a pharmaceutical composition comprising as an active ingredient a compound consisting of an antibody of the invention, or one of its derived compounds or functional fragments. Preferably, said antibody is supplemented by an excipient and/or a pharmaceutically acceptable carrier.

According to still another embodiment, the present invention also relates to a pharmaceutical composition as described above that comprises at least a second anti-tumor compound selected among the compounds capable of specifically inhibiting the tyrosine kinase activity of receptors such as IGF-IR, EGFR, HER2/neu, cMET, VEGFR or VEGF, or any other anti-tumor compound known to a person skilled in the art. In a second preferred aspect of the invention, said second compound can be selected among the antibodies antiEGFR, antiIGF-IR, antiHER2/neu, anticMET, VEGFR, VEGF, etc., isolated, or their functional fragments and derived compounds, capable of inhibiting the proliferative and/or anti-apoptotic and/or angiogenic and/or inductive activity of metastatic dissemination promoted by said receptors.

According to still another embodiment of the invention, the composition comprises, in addition, as a combination product for use in a simultaneous, separated or extended fashion, at least one inhibiter of the tyrosine kinase activity of receptors such as IGF-IR, EGFR, HER2/neu, cMET and VEGFR.

In another preferred embodiment, said inhibiter of the tyrosine kinase activity of these receptors is selected from the group comprising derived natural agents, dianilinophthalimides, pyrazolo- or pyrrolo-pyridopyrimidines or quinazolines. Such inhibiting agents, well-known to a person skilled in the art, are described in the literature (Ciardiello F., Drugs 2000, Suppl. 1, 25-32).

Another embodiment complementary to the invention consists of a composition as described above comprised of, in addition, as a combination product for simultaneous, separated or extended use, a cytotoxic/cytostatic agent.

"Simultaneous use" means the administration of both compounds of the composition comprised in a single dosage form.

"Separated use" means administration, at the same time, of both compounds of the composition, comprised in distinct dosage forms.

"Extended use" means the successive administration of both compounds of the composition, each comprised in a distinct dosage form.

Generally, the composition according to the invention considerably increases cancer treatment effectiveness. In other words, the therapeutic effect of the antibody of the invention is enhanced in an unexpected way by the administration of a cytotoxic agent. Another major subsequent advantage produced by a composition of the invention relates to the possibility of using lower effective doses of the active ingredient, thus making it possible to avoid or reduce the risks of the appearance of side effects, in particular the effect of the cytotoxic agent. Moreover, this composition makes it possible to achieve the expected therapeutic effect more quickly.

"Therapeutic anticancer agent" or "cytotoxic agent" means a substance which, when it is administered to a patient, treats or prevents the development of cancer in the patient. Non-limiting examples of such agents include "alkylating" agents, antimetabolites, antitumor antibiotics, mitotic inhibitors, inhibitors of chromatin functioning, antiangiogenics, antiestrogens, antiandrogens and immunomodulators.

Such agents, for example, are cited in VIDAL, on the page devoted to compounds related to oncology and hematology under the heading "Cytotoxic"; the cytotoxic compounds cited by reference to this document are cited herein as preferred cytotoxic agents.

"Alkylating agent" refers to any substance that can bind covalently with or can alkylate any molecule, preferentially a nucleic acid (e.g., DNA), within a cell. Examples of such alkylating agents include nitrogen mustards such as mechlorethamine, chlorambucil, melphalan, chlorhydrate, pipobroman, prednimustine, disodium phosphate or estramustine; oxazaphosphorines such as cyclophosphamide, altretamine, trofosfamide, sulfofosfamide or ifosfamide; aziridines or ethylene-imines such as thiotepa, triethyleneamine or altetramine; nitrosoureas such as carmustine, streptozocine, fotemustine or lomustine; alkyl sulfonates such as busulfan, treosulfan or improsulfan; triazenes such as dacarbazine; or platinum complexes such as cisplatine, oxaliplatine or carboplatine.

"Antimetabolite" refers to a substance that blocks growth and/or cellular metabolism by interfering with certain activities, generally DNA synthesis. Examples of antimetabolites include methotrexate, 5-fluorouracile, floxuridine, 5-fluorodeoxyuridine, capecitabine, cytarabine, fludarabine, cytosine arabinoside, 6-mercaptopurine (6-MP), 6-thioguanine (6-TG), chlorodesoxyadenosine, 5-azacytidine, gemcitabine, cladribine, deoxycoformycin and pentostatin.

"Antitumor antibiotic" refers to a compound that can prevent or inhibit the synthesis of DNA, RNA and/or proteins. Examples of such antitumor antibiotics include doxorubicin, daunorubicin, idarubicin valrubicin, mitoxantrone, dactinomycin, mithramycin, plicamycin, mitomycin C, bleomycin and procarbazine.

"Mitotic inhibitors" prevent the normal progression of the cell cycle and mitosis. In general, microtubule inhibitors or "taxoids" such as paclitaxel and docetaxel are capable of inhibiting mitosis. The vinca alkaloids, such as vinblastine, vincristine, vindesine and vinorelbine, are also capable of inhibiting mitosis.

"Chromatin inhibiters" or "topoisomerase inhibiters" are substances that inhibit the normal functioning of proteins that shape chromatin, such as topoisomerases I and II. Examples of such inhibiters include, for topoisomerase I, camptothecine and its derivatives, such as irinotecan or topotecan; for topoisomerase II, etoposide, etiposide phosphate and teniposide.

An "antiangiogenic" is any drug, compound, substance or agent that inhibits the growth of the blood vessels. Examples of antiangiogenics include, without being limiting, razoxin, marimastat, batimastat, prinomastat, tanomastat, ilomastat, CGS-27023A, halofuginone, COL-3, neovastat, BMS-275291, thalidomide, CDC 501, DMXAA, L-651582, squalamine, endostatine, SU5416, SU6668, interferon-alpha, EMD121974, interleukin-12, IM862, angiostatin and vitaxin.

"Antiestrogen" or "estrogen antagonist" refers to any substance that decreases, antagonizes or inhibits estrogen action. Examples of such agents are tamoxifene, toremifene, raloxifene, droloxifene, iodoxyfene, anastrozole, letrozole and exemestane.

"Antiandrogen" or "androgen antagonist" refers to any substance that reduces, antagonizes or inhibits androgen action. Examples of antiandrogens include flutamide, nilutamide, bicalutamide, sprironolactone, cyproterone acetate, finasteride and cimitidine.

Immunomodulators are substances that stimulate the immune system. Examples of immunomodulators include interferon, interleukins such as aldesleukin, OCT-43, denileukin diftitox or interleukine-2, tumor necrosis factors such as tasonermine, or other types of immunomodulators such as lentinan, sizofuran, roquinimex, pidotimod, pegademase, thymopentine, poly I:C or levamisole in combination with 5-fluorouracil.

For further details, a person skilled in the art can refer to the manual published by the French Association of Therapeutic Chemistry Teachers titled "Therapeutic chemistry, vol. 6, Antitumor drugs and perspectives in the treatment of cancer, TEC and DOC edition, 2003 [in French]".

In a particularly preferred embodiment, said composition of the invention as a combination product is characterized in that said cytotoxic agent is bound chemically to said antibody for use simultaneously.

In a particularly preferred embodiment, said composition is characterized in that said cytotoxic/cytostatic agent is selected among the spindle inhibitors or stabilizers, preferably vinorelbine and/or vinflunine and/or vincristine.

In order to facilitate binding from said cytotoxic agent and the antibody according to the invention, spacer molecules can be introduced from the two compounds to bind, such as the poly(alkylene)glycol polyethyleneglycol or the amino acids; or, in another embodiment, said cytotoxic agents' active derivatives, into which have been introduced functions capable of reacting with said antibody, can be used. These binding techniques are well-known to a person skilled in the art and will not be discussed in more detail in the present description.

Other EGFR inhibiters include, without being limiting, monoclonal antibodies C225 and antiEGFR 22Mab (ImClone Systems Incorporated), ABX-EGF (Abgenix/Cell Genesys), EMD-7200 (Merck KgaA) or compounds ZD-1834, ZD-1838 and ZD-1839 (AstraZeneca), PKI-166 (Novartis), PKI-166/CGP-75166 (Novartis), PTK 787 (Novartis), CP 701 (Cephalon), flunomide (Pharmacia/Sugen), CI-1033 (Warner Lambert Parke Davis), CI-1033/PD 183, 805 (Warner Lambert Parke Davis), CL-387, 785 (Wyeth-Ayerst), BBR-1611 (Boehringer Mannheim GMBH/Roche), Naamidine A (Bristol-board Myers Squibb), RC-3940-II (Pharmacia), BIBX-1382 (Boehringer Ingelheim), OLX-103 (Merck & Co), VRCTC-310 (Ventech Research), EGF fusion toxin (Seragen Inc.), DAB-389 (Seragen/Lilgand), ZM-252808 (Imperial Cancer Research Fund), RG-50864 (INSERM), LFM-A12 (Parker Hughes Center Cancer), WHI-P97 (Parker Hughes Center Cancer), GW-282974 (Glaxo), KT-8391 (Kyowa Hakko) or the "EGFR vaccine" (York Medical/Centro of Immunologia Molecular).

Another aspect of the invention relates to a composition characterized in that at least one of said antibodies, or of the derived compounds or functional fragments of same, is conjugated with a cellular toxin and/or a radioisotope.

Preferably, said toxin or said radioisotope is capable of preventing the growth or proliferation of the tumor cell, notably of completely inactivating said tumor cell.

Also preferably, said toxin is an enterobacteria toxin, notably *Pseudomonas* exotoxin A.

The radioisotopes preferentially combined with therapeutic antibodies are radioisotopes that emit gamma rays, preferentially iodine$^{131}$, yttrium$^{90}$, gold$^{199}$, palladium$^{100}$, copper$^{67}$, bismuth$^{217}$ and antimony$^{211}$. Radioisotopes that emit alpha and beta rays can also be used in therapy.

"Toxin or radioisotope combined with at least one antibody of the invention, or a functional fragment of same" refers to any means that makes it possible to bind said toxin or said radioisotope to that at least one antibody, notably by covalent binding from the two compounds, with or without the introduction of the binding molecule.

Examples of agents that allow chemical (covalent), electrostatic, or non-covalent bonding of all or part of the conjugate's elements include, in particular, benzoquinone, carbodiimide and more particularly EDC (1-ethyl-3-[3-dimethyl-aminopropyl]-carbodiimide-hydrochloride), dimaleimide, dithiobis-nitrobenzoic (DTNB) acid, N-succinimidyl S-acetyl thio-acetate (SATA), bridging agents with one or more groups, with one or more phenylaside groups, reacting with ultraviolet (UV) rays, most preferentially N-[-4 (azidosalicylamino)butyl]-3'-(2'-pyridyldithio)-propionamide (APDP), N-succinimid-yl 3(2-pyridyldithio) propionate (SPDP) and 6-hydrazino-nicotinamide (HYNIC).

Another form of binding, notably for radioisotopes, can consist of the use of bifunctional ion chelating agents.

Examples of such chelators include the chelators derived from EDTA (ethylenediaminetetraacetic acid) or DTPA (diethylenetriaminepentaacetic acid) which were developed to bind metals, particularly radioactive metals, with immunoglobulins. Thus, DTPA and its derivatives can be substituted on the carbon chain by various groups in such a way as to increase the stability and the rigidity of the ligand-metal complex (Krejcarek et al., 1977; Brechbiel et al., 1991; Gansow, 1991; U.S. Pat. No. 4,831,175).

For example, DTPA (diethylenetriaminepentaacetic acid) and its derivatives, which long have been widely used in drug and biology either in its free form or in a complex with a metal ion, exhibit the remarkable characteristic of forming stable chelates with metal ions which can be coupled with proteins of therapeutic or diagnostic interest, such as antibodies, for the development of radio-immuno conjugates for cancer therapy (Meases et al., 1984; Gansow et al., 1990).

Also preferably, said at least one antibody of the invention forming said conjugate is selected among its functional fragments, notably fragments that have lost their Fc component, such as scFv fragments.

The present invention also comprises the use of the composition for the preparation of a drug intended for the prevention or the treatment of cancer.

The present invention also relates to the use of an antibody, or a derived compound or functional fragment of same, preferably humanized, and/or of a composition according to the invention for the preparation of a drug for inhibiting the growth of tumor cells. Generally, the present invention relates to the use of an antibody, or a derived compound or functional fragment of same, preferably humanized, and/or of a composition, for the preparation of a drug for cancer prevention or treatment.

Preferred cancers that can be prevented and/or treated include prostate cancer, osteosarcoma, lung cancer, breast cancer, endometrial cancer, colon cancer, multiple myeloma, ovarian cancer, pancreatic cancer or any other cancer.

In a preferred manner, said cancer is a cancer selected among estrogen-related breast cancer, non-small cell lung cancer, colon cancer and/or pancreatic cancer.

Another aspect of the present invention relates to the use of the antibody as described in a diagnostic method, preferably in vitro, of diseases related to JAM-A expression level. Preferably, said JAM-A protein related diseases in said diagnostic method will be cancers.

Thus, the antibodies of the invention, or the derived compounds or functional fragments of same, can be employed in a method for the detection and/or quantification of JAM-A protein in a biological sample in vitro, notably for the diagnosis of diseases associated with an abnormal expression with this protein, such as cancers, wherein said method comprises the following steps:

a) placing the biological sample in contact with an antibody according to the invention, or a derived compound or functional fragment of same;

b) demonstrating the antigen-antibody complex possibly formed.

Thus, the present invention also comprises the kits or accessories for the implementation of a method as described (for detecting the expression of a gene from *Legionella pneumophila* Paris or from an associated organism, or for detecting and/or identifying *Legionella pneumophila* Paris bacteria or associated microorganisms), comprising the following elements:

a) a polyclonal or monoclonal antibody of the invention;

b) optionally, reagents for constituting the medium favorable to immunological reactions;

c) optionally, reagents that reveal the antigen-antibodies complexes produced by the immunological reaction.

Advantageously, the antibodies or functional fragments of same can be immobilized on a support, notably a protein chip. One such protein chip is an object of the invention.

Advantageously, the protein chips can be used in the kits or accessories required for detecting and/or quantifying JAM-A protein in a biological sample.

It must be stated that the term "biological sample" relates herein to samples taken from a living organism (notably blood, tissue, organ or other samples taken from a mammal, notably man) or any sample likely to contain one such JAM-A protein (such as a sample of cells, transformed if needed).

Said antibody, or a functional fragment of same, can be in the form of an immunoconjugate or of a labeled antibody in order to obtain a detectable and/or quantifiable signal.

The labeled antibodies of the invention, or the functional or fragments of same, include, for example, antibody conjugates (immunoconjugates), which can be combined, for example, with enzymes such as peroxidase, alkaline phosphatase, α-D-galactosidase, glucose oxidase, glucose amylase, carbonic anhydrase, acetyl-cholinesterase, lysozyme, malate dehydrogenase or glucose-6 phosphate dehydrogenase or by a molecule such as biotin, digoxigenin or 5-bromo-desoxyuridine.

Fluorescent labels can be also combined with the antibodies of the invention or functional fragments of same, including notably fluorescein and its derivatives, fluorochrome, rhodamine and its derivatives, green fluorescent protein (GFP), dansyl, umbelliferone, etc. In such conjugates, the antibodies of the invention or functional fragments of same can be prepared by methods known to a person skilled in the art. They can be bound with enzymes or fluorescent labels directly; via a spacer group or a linkage group such as polyaldehyde, glutaraldehyde, ethylenediaminetetraacetic acid (EDTA) or diethylenetriaminepentaacetic acid (DPTA); or in the presence of binding agents such as those mentioned above for therapeutic conjugates. Conjugates carrying fluorescein labels can be prepared by reaction with an isothiocyanate.

Others conjugates can also include chemiluminescent labels such as luminol and dioxetane, bioluminescent labels such as luciferase and luciferin, or radioactive labels such as iodine$^{123}$, iodine$^{125}$, iodine$^{126}$, iodine$^{133}$, bromine$^{77}$, technetium$^{99m}$, indium$^{111}$, indium$^{113m}$, gallium$^{67}$, gallium$^{68}$, ruthenium$^{95}$, ruthenium$^{97}$, ruthenium$^{103}$, ruthenium$^{105}$, mercury$^{107}$, mercury$^{203}$, rhenium$^{99m}$, rhenium$^{101}$, rhenium$^{105}$, scandium$^{47}$, tellurium$^{121m}$, tellurium$^{122m}$, tellurium$^{125m}$, thulium$^{165}$, thulium$^{167}$, thulium$^{168}$, fluorine$^{18}$, yttrium$^{199}$ and iodine$^{131}$. Existing methods known to a person skilled in the art for binding radioisotopes with antibodies, either directly or via a chelating agent such as the EDTA or DTPA mentioned above, can be used for as diagnostic radioisotopes. Thus should be mentioned labeling with [I$^{125}$]Na by the chloramine-T technique [Hunter W. M. and Greenwood F. C. (1962) Nature 194:495]; labeling with technetium$^{99m}$ as described by Crockford et al. (U.S. Pat. No. 4,424,200) or bound via DTPA as described by Hnatowich (U.S. Pat. No. 4,479,930).

The invention also relates to the use of an antibody according to the invention for the preparation of a drug for the specific targeting of a compound that is biologically active toward cells expressing or overexpressing JAM-A protein.

In the sense of the present description, a "biologically active compound" is any compound capable of modulating, notably inhibiting, cellular activity, notably growth, proliferation, transcription and gene translation.

The invention also relates to an in vivo diagnostic reagent composed of an antibody according to the invention, or a functional fragment of same, preferably labeled, notably radiolabeled, and its use in medical imaging, notably for the detection of cancer related to the cellular expression or overexpression of JAM-A protein.

The invention also relates to a composition as a combination product or to an anti-JAM-A/toxin conjugate or radioisotope, according to the invention, used as drug.

Preferably, said composition as a combination product or said conjugate will be supplemented by an excipient and/or a pharmaceutical vehicle.

In the present description, "pharmaceutical vehicle" means a compound, or a combination of compounds, entering a pharmaceutical composition that does not cause secondary reactions and that, for example, facilitates administration of the active compounds, increases its lifespan and/or effectiveness in the organism, increases its solubility in solution or improves its storage. Such pharmaceutical carriers are well-known and will be adapted by a person skilled in the art according to the nature and the administration route of the active compounds selected.

Preferably, such compounds will be administered by systemic route, notably by intravenous, intramuscular, intradermal, intraperitoneal, subcutaneous or oral route. More preferably, the composition composed of the antibody according to the invention will be administered in several doses spaced equally over time.

Their administration routes, dosing schedules and optimal galenic forms can be determined according to the criteria generally taken into account when establishing a treatment suited to a patient such as, for example, the patient's age or body weight, the seriousness of his general state, his tolerance for the treatment and the side effects experienced.

Thus, the invention relates to the use of an antibody, or one of its functional fragments, for the preparation of a drug for the specific targeting of a compound that is biologically active toward cells expressing or overexpressing JAM-A.

Other characteristics and advantages of the invention appear further in the description with the examples and figures whose legends are presented below.

BRIEF DESCRIPTION OF THE FIGURES

FIG. 1 shows the respective sequences of the heavy (DNA sequence disclosed as SEQ ID NO: 33; protein sequence disclosed as SEQ ID NO: 14) and light (DNA sequence disclosed as SEQ ID NO: 32; protein sequence disclosed as SEQ ID NO: 13) chains of the murine 6F4 antibody. CDRs are underlined and in bold (according to the Kabat numbering).

FIGS. 2A and 2B represent the respective alignments of the V (FIG. 2A) and J (FIG. 2B) regions of murine 6F4 antibody and the murine cell lines selected, namely IGKV19-93*01 (SEQ ID No. 39) for the V region and IGKJ1*01 (SEQ ID No. 40) for the J region. FIG. 2A discloses SEQ ID NOS 13 and 69-70, respectively, in order of appearance. FIG. 2B discloses SEQ ID NOS 40, 71 and 71, respectively, in order of appearance.

FIGS. 3A and 3B represent the respective alignments of the V (FIG. 3A) and J (FIG. 3B) regions of murine 6F4 antibody and the human cell lines selected, namely IGKV1-33*01 (SEQ ID No. 41) for the V region and IGKJ1*01 (SEQ ID No. 42) for the J region. FIG. 3A discloses SEQ ID NOS 72-75, respectively, in order of appearance. FIG. 3B discloses SEQ ID NOS 76, 40 and 77-78, respectively, in order of appearance.

FIG. 4 is the protein sequence of the light chain of the 6F4 antibody (SEQ ID NO: 13) with reference to the respective KABAT and IMGT numbering systems.

FIGS. 5A, 5B and 5C represent the respective alignments of the V (FIG. 5A), D (FIG. 5B) and J (FIG. 5C) regions of the murine 6F4 antibody and the murine cell lines selected, namely IGHV1S135*01 (SEQ ID No. 43) for the V region, IgHD-ST4*01 (SEQ ID No. 44) for the D region and IgHJ2*01 (SEQ ID No. 45) for the J region. FIG. 5A discloses SEQ ID NOS 14, 79 and 54, respectively, in order of appearance. FIG. 5B discloses SEQ ID NOS 80-81, respectively, in order of appearance. FIG. 5C discloses SEQ ID NOS 82-84, respectively, in order of appearance.

FIGS. 6A, 6B and 6C represent the respective alignments of the V (FIG. 6A), D (FIG. 6B) and J (FIG. 6C) regions of the murine 6F4 antibody and the human cell lines selected, namely IGHV1-f*01 (SEQ ID No. 46) for the V region, IGHD1-1*01 (SEQ ID No. 47) for the D region and IGHJ4*01 (SEQ ID No. 48) for the J region. FIG. 6A discloses SEQ ID NOS 85-86, 57 and 46, respectively, in order of appearance. FIG. 6B discloses SEQ ID NOS 87-88, respectively, in order of appearance. FIG. 6C discloses SEQ ID NOS 89, 45, 90 and 48, respectively, in order of appearance.

FIG. 7 is the protein sequence of the heavy chain of the 6F4 antibody (SEQ ID NO: 141 with reference to the respective KABAT and IMGT numbering systems.

FIGS. 9A and 9B present an analysis by SDS-PAGE electrophoresis (FIG. 9A) and western blot (FIG. 9B) of immunopurified protein. Two purifications (#1 and #2) were performed and analyzed under reducing and in non-reducing conditions.

FIG. 10 presents an analysis by MALDI-TOF mass spectrometry of the mixture of peptides extracted after tryptic hydrolysis.

FIGS. 11A and 11B consist of the confirmation of a protein identified by western blot (non-reducing conditions): revealed using 6F4 antibody (FIG. 11A) and anti-human JAM-A polyclonal antibody (FIG. 11B).

FIG. 12 shows the specificity of the 6F4 antibody for human JAM-A protein. The quantities deposited for each protein are 250 ng, 25 ng and 10 ng.

FIG. 17 is the sequence of the humanized 6F4 VL domain (SEQ ID NO: 91) wherein: * correspond to amino acids changed de facto to their human counterparts, 1 correspond to amino acids analyzed for their abilities to be humanized, the human residue being indicated below the sign, and 2 correspond to amino acids that remain murin in the humanized 6F4 VL domain.

FIG. 18 is the sequence of the humanized 6F4 VH domain (SEQ ID NO: 92) wherein: * correspond to amino acids changed de facto to their human counterparts, 1 correspond to amino acids analysed for their abilities to be humanized, the human residue being indicated below the sign, and 2 correspond to amino acids that remain murin in the humanized 6F4 VH domain.

FIG. 27 illustrates the effect of the 6F4 antibody on A. non specific lyphoproliferation induced with PHA and B. antigen presentation process. First experiment with 2 independent donors.

FIG. 28 illustrates the effect of the 6F4 antibody on A. non specific lyphoproliferation induced with PHA and B. antigen presentation process. Second experiment with 2 independent donors.

FIG. 31 is the alignment of the 6F4 VH domain and IGHV1-03*01 germline gene (SEQ ID No. 49). Figure discloses SEQ ID NOS 93-95, respectively, in order of appearance.

FIG. 32 is the IGKV1-27*01 based humanized version of 6F4 VL with mentioned mutations (BU-L1). Figure discloses SEQ ID NOS 13 and 96-97, respectively, in order of appearance.

FIG. 33 is the IGKV1D-43*01 based humanized version of 6F4 VL with mentioned mutations (BU-L2). Figure discloses SEQ ID NOS 13 and 98-99, respectively, in order of appearance.

FIG. 34 is the IGHV1-3*01 based humanized version of 6F4 VH with mentioned mutations (BU-H1). Figure discloses SEQ ID NOS 14 and 100-101, respectively, in order of appearance.

FIG. 35 is the IGHV1-46*01 based humanized version of 6F4 VH with mentioned mutations (BU-H2). Figure discloses SEQ ID NOS 14, 102 and 101, respectively, in order of appearance.

Figure 8A:
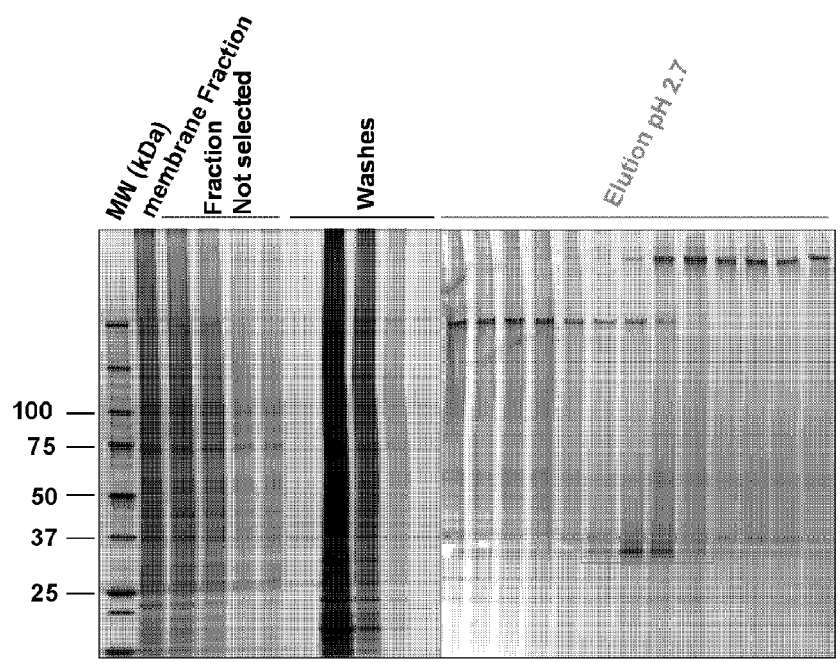
FIGS. 8A and 8B represent the 6F4-sepharose immunopurification of 6F4 antigen from HT-29 cell membranes. Analyses of fractions collected by SDS-PAGE electrophoresis (FIG. 8A) and western blot (FIG. 8B) are presented as well.

In order to further illustrate the present invention and the advantages thereof, the following specific examples are given, it being understood that same are intended only as illustrative and in nowise limitative.

EXAMPLES

Example 1

Generation of the 6F4 Antibody

To generate the murine monoclonal antibody (Mab), BALB/C mice were immunized using $5\times10^6$ MCF-7 cells from ATCC. After a final booster injection of $10^7$ MCF-7 cells, cells from lymph nods of mice are fused with Sp2/O-Ag14 myeloma cells using the techniques classically described by Kohler and Milstein. The supernatants of the hybridomas arising from the fusion were then screened for functional activity, namely the inhibition of the proliferation of MCF-7 cells in vitro.

For this screening, MCF-7 cells are cultured in 96-well culture dishes at $5\times10^3$ cells/well in 100 µl of hybridoma medium without fetal calf serum. The plates are incubated for 24 hours at 37° C. under an atmosphere of 5% $CO_2$. After 24 hours, 50 µl of the supernatant of the hybridomas to be screened are added to each well. The last line on the plate is reserved for the controls:

three wells are supplemented by 50 µl of a hybridoma supernatant that is non-relevant with respect to the activity sought and that is cultured in the same culture medium as that used for the fused cells. These wells will be used to calibrate the impact of inactive supernatant on the incorporation of tritiated thymidine;

three wells will receive 50 µl of hybridoma culture medium.

After roughly 52 hours of culture, each well is supplemented by 0.25 µCi of [³H]thymidine and incubated again for 20 hours at 37° C. The incorporation of [³H]thymidine in the DNA, indicating cell proliferation, is quantified by measuring liquid scintillation. Background noise and thresholds are determined for each plate as a function of the control wells containing the medium alone and the non-relevant hybridoma supernatant.

By this method, 43 hybridomas secreting antibodies inhibiting the growth of MCF-7 cells were selected after a first screening. Eleven of these 43 hybridomas had weak or non-existent growth and were abandoned. During proliferation tests performed following the expansion and cloning of the hybridomas, only the hybridomas whose supernatant had a ≧20% inhibiting activity on the proliferation of MCF-7 cells were selected. At the end of the cloning/selection process, only one clone proved to have the required properties, the 6F4 clone.

Example 2

Process of Humanization by CDR-Grafting of the Variable Region of the Light Chain of the 6F4 Antibody (6F4 VL)

a) Comparison of the 6F4 VL Nucleotide Sequence with all Known Murine Cell Line Sequences As a preliminary step in humanization by CDR-grafting, the 6F4 VL nucleotide sequence initially was compared with all of the murine cell line sequences present in the IMGT data bank.

Regions V and J of mouse cell lines having a sequence identity of 98.56% for the V region and 100% for the J region were identified, respectively IGKV19-93*01 (SEQ ID No. 39, EMBL nomenclature: AJ235935) and IGKJ1*01 (SEQ ID No. 40, EMBL nomenclature: V00777).

Considering these identity percentages, it was decided to use the 6F4 VL sequence directly.

These alignments are represented in FIG. 2A for the V region and in FIG. 2B for the J region.

b) Comparison of the Nucleotide Sequence of 6F4 VL with all Known Human Cell Line Sequences In order to identify the best human candidate for CDR-grafting, the human-origin germline having the greatest possible identity with 6F4 VL was sought. For this purpose, the nucleotide sequence of mouse 6F4 VL was compared with all of the human cell line sequences present in the IMGT data base.

Regions V and J of human-origin cell lines were identified with a sequence identity of 81.36% for the V region, namely IGKV1-33*01 (SEQ ID No. 41, EMBL nomenclature: M64856) and 86.84% for the J region, namely IGKJ1*01 (SEQ ID No. 42, EMBL nomenclature: J00242).

Cell lines IGKV1-33*01 for the V region and IGKJ1*01 for the J region were thus selected as human receptor sequences for mouse 6F4 VL CDRs.

These alignments are presented in FIG. 3A for the V region and in FIG. 3B for the J region.

c) Humanized Versions of 6F4 VL

The following step in the humanization process consists of joining together the IGKV1-33*01 and IGKJ1*01 cell line sequences and then joining the mouse 6F4 VL CDRs to the scaffold regions of these same germlines.

This stage of the process the molecular model of the mouse 6F4 Fv regions will be particularly useful in the choice of mouse residues to preserve because they may play a role either in maintaining the molecule's three-dimensional structure (canonical structure of CDRs, VH/VL interfaces, etc.) or in binding the antigen. In the scaffold regions, each difference from mouse (6F4 VL) and human (IGKV1-33*01/IGKJ1*01) nucleotides will be examined very carefully.

For more clarity in the following, FIG. 4 presents the 6F4VL sequence with reference to KABAT and IMGT classifications.

Three murine residues were identified which must be preserved.

Residue 33 (Ile) takes part in CDR1 anchoring according to IMGT and is part of CDR1 according to Kabat.

Residue 49 (His) takes part in CDR2 anchoring according to IMGT, takes part in the VH/VL interface and belongs to the Vernier zone.

Residue 53 (Thr) takes part in CDR2 anchoring according to IMGT and is part of CDR2 according to Kabat.

Initially, three changes in the scaffold regions of IGKV1-33*01 and IGKJ1*01 will be studied. These changes relate to residues 24, 69 and 71 (IMGT nomenclature). It should be understood, of course, that these three changes will be studied independently of each other and also in various combinations. The aim is to have available all possible mutants in order to test them and to select the mutant that has preserved the best binding properties. ELISA/Biacore binding tests will thus be performed on each mutant.

Residue 24 (Lys/Gln) is near CDR1 and could as a result be critical for maintaining a conformation that enables proper CDR1 presentation. More particularly, this residue is likely to interact with residues 69-70 within the Vernier zone. Lys is only slightly represented in human VLs but is part of CDR1 according to Kabat.

Although residue 69 (Arg/Thr) is in the Vernier zone and thus directly takes part in CDR1's canonical structure, this residue is always Thr in the human VL.

Although residue 71 (Tyr/Phe) directly takes part in CDR1's canonical structure, it is systematically Phe in the human VL.

Secondly, a modification of residue 56 (Ala) into Thr can be considered. This residue, although outside of CDRs according to IMGT, belongs to CDR2 according to Kabat.

Third and last, two additional changes could be made at residues 34 and 55 (IMGT nomenclature). The two residues, outside of the CDRs defined IMGT, are included in the CDRs defined by Kabat.

Residue 34 (Ala/Asn) belongs to CDR1 according to Kabat and takes part in the VH/VL interface. Such a mutation remains relevant in spite of the strong representation of Ala in man.

Residue 55 (Gln/Glu) is part of CDR2 according to Kabat and also takes part in the VH/VL interface. Such a mutation also remains relevant in spite of the strong representation of Gln in man.

As was described above, these three mutations could be tested independently or in various combinations.

Example 3

Process of Humanization by CDR-Grafting of the Variable Region of the Heavy Chain of the 6F4 Antibody (6F4 VH)

a) Comparison of the 6F4 VH Nucleotide Sequence with all Known Murine Cell Line Sequences As a preliminary step in humanization by CDR-grafting, the 6F4 VH nucleotide sequence initially was compared with all of the murine cell line sequences present in the IMGT data bank.

Regions V, D and J of murine cell lines having a sequence identity of 99.30% for the V region (IGHV1S135*01; SEQ ID No. 43; EMBL nomenclature: AF304556), of 80% for the D region (IgHD-ST4*01; SEQ ID No. 44; EMBL nomenclature: M23243) and of 100% for the J region (IgHJ2*01; SEQ ID No. 45; EMBL nomenclature: V00770).

These alignments are represented in FIG. 5A for the V region, FIG. 5B for the D region and FIG. 5C for the J region.

Considering these identity percentages, it was decided to use the 6F4 VH sequence directly, as was the case for 6F4 VL.

b) Comparison of the Nucleotide Sequence of 6F4 VH with all Known Human Cell Line Sequences In order to identify the best human candidate for CDR-grafting, the human-origin germline having the greatest possible identity with each of the three regions V, D and J of 6F4 VH was sought. For this purpose, the nucleotide sequence of mouse 6F4 VH was compared with all of the human cell line sequences present in the IMGT data base.

Human-origin germlines were identified having an sequence identity of 75.34% for the V region (IGHV1-f*01; SEQ ID No. 46; EMBL nomenclature: Z12305), of 71.42% for the D region (IGHD1-1*01; SEQ ID No. 47; EMBL nomenclature: X97051) and of 87.51% for the J region (IGHJ4*01; SEQ ID No. 48, EMBL nomenclature: J00256).

For each of the regions V, D and J, the germinal lines above were selected and rearranged from them.

These alignments are presented in FIG. 6A for the V region, FIG. 6B for the D region and FIG. 6C for the J region.

c) Humanized Versions of 6F4 VH

The following step in the humanization process consists of joining together the IGHV1-f*01, IGHD1-1*01 and IGHJ4*01 cell line sequences and then joining the mouse 6F4 VH CDRs to the scaffold regions of these same germlines.

This stage of the process the molecular model of the mouse 6F4 Fv regions will be particularly useful in the choice of the mouse residues to preserve because they may play a role either in maintaining the molecule's three-dimensional structure (canonical structure of CDRs, VH/VL interfaces, etc.) or in binding the antigen. In the scaffold regions, each difference from mouse (6F4 VH) and human (IGHV1-f*01, IGHD1-1*01 and IGHJ4*01) nucleotides will be examined very carefully.

For more clarity in the following, FIG. 7 presents the 6F4VH sequence with reference to KABAT and IMGT classifications.

As was the case with the light chain, four residues that must remain unchanged were identified.

Residue 2 (Ile) is part of Vernier zone and takes part in CDR3 structuring.

Residue 35 (Tyr) takes part in CDR1 anchoring according to IMGT, is part of CDR1 according to Kabat, and also takes part in the VH/VL interface and interacts with CDR3.

Residue 50 (Tyr) takes part in CDR2 anchoring according to IMGT, is part of CDR2 according to Kabat, is also part of the Vernier zone and also takes part in the VH/VL interface.

Residue 59 (Arg) takes part in CDR2 anchoring according to IMGT, is part of CDR2 according to Kabat and takes part in the VH/VL interface.

A first humanized version will be able to include three mutations at residues 61, 62 and 65, respectively (IMGT classification).

These three residues are located in CDR2 according to Kabat and take part in the VH/VL interface.

Residue 61 (Asn/Ala) is not directly implicated in antigen recognition. Its mutation can thus be considered.

Residue 62 (Gln/Glu) and residue 65 (Lys/Gln).

Secondly, two additional changes will be evaluated. The two changes relate to residues 48 and 74 (IMGT nomenclature).

Residue 48 (Ile/Met), belonging to the scaffold region, takes part in the VH/VL interface.

Residue 74 (Lys/Thr) is part of the Vernier zone and may be implicated in CDR2 structuring.

Third and last, a third series of mutations could be considered, namely a change of residues 9 (Pro/Ala) and 41 (His/Pro). The aim is thus, in a way similar to the mutations planned for 6F4 VL, to approach the human germline as closely as possible without modifying CDR anchoring.

For summary purpose only, tables 5 and 6 below list the cell lines used as well as, respectively, their amino acid and nucleotide sequence numbers.

TABLE 5

| GERMLINES (EMBL ref.) | SEQ ID No. |
| --- | --- |
| IGKV19-93*01 (AJ235935) | 39 |
| IGKJ1*01 (V00777) | 40 |
| IGKV1-33*01 (M64856) | 41 |
| IGKJ1*01 (J00242) | 42 |
| IGHV1S135*01 (AF304556) | 43 |
| IGHD-ST4*01 (M23243) | 44 |
| IGHJ2*01 (V00770) | 45 |
| IGHV1-f*01 (Z12305) | 46 |
| IGHD1-1*01 (X97051) | 47 |
| IGHJ4*01 (J00256) | 48 |
| IGHV1-03*01 (X62109) | 49 |

TABLE 6

| GERMLINES (EMBL ref.) | SEQ ID No. |
| --- | --- |
| IGKV19-93*01 (AJ235935) | 50 |
| IGKJ1*01 (V00777) | 51 |
| IGKV1-33*01 (M64856) | 52 |
| IGKJ1*01 (J00242) | 53 |
| IGHV1S135*01 (AF304556) | 54 |
| IGHD-ST4*01 (M23243) | 55 |
| IGHJ2*01 (V00770) | 56 |
| IGHV1-f*01 (Z12305) | 57 |
| IGHD1-1*01 (X97051) | 58 |
| IGHJ4*01 (J00256) | 59 |
| IGHV1-03*01 (X62109) | 60 |

Example 4

Purification and Identification of the 6F4 Antibody Antigen Target

Figure 8B:
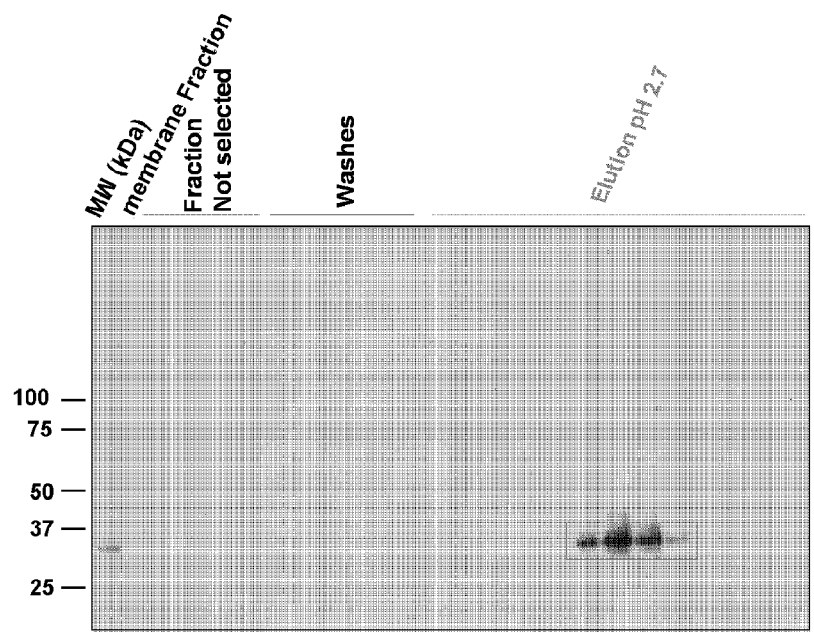

Purification by Immunoaffinity:

The antigen target of the 6F4 antibody is purified from a membrane fraction enriched by HT-29 cells. After solubilization in a 50 mM Tris/HCl buffer, pH 7.4, containing 150 mM NaCl, Triton X-100 and IGEPAL, membrane proteins are incubated in the presence of the 6F4 antibody immobilized on sepharose beads overnight at +4° C. under gentle mixing. The 6F4-Ag complex formed on the beads is then washed with various solutions containing detergents in order to eliminate proteins adsorbed nonspecifically. The 6F4 antigen target is eluted from the 6F4-sepharose support using a 0.1 M Gly/HCl buffer, pH 2.7. The fractions collected are analyzed by SDS-PAGE electrophoresis (10% gel, non-reducing conditions) and western blot after transfer to nitrocellulose membrane (primary 6F4 antibody used at 0.5 µg/ml, detection by chemiluminescence) in order to select the fractions enriched in the antigen of interest (FIGS. 8A and 8B). The analysis by western blot confirms the absence of the protein of interest in the un-selected fractions and washings, and a specific elution of the latter at acid pH.

The enriched fractions arising from two purifications were then analyzed by SDS-PAGE electrophoresis (10% gel) and western blot under the conditions described previously. The antigen recognized by the 6F4 antibody in the western blot had an apparent molecular weight of 35 kDa after analysis in reducing conditions (FIGS. 9A and 9B). A difference in apparent molecular weight can be noted when electrophoresis is performed in non-reducing conditions: under these conditions, the apparent molecular weight is indeed slightly lower than that observed in reducing conditions.

Identification of the Antigen Target:

After SDS-PAGE electrophoresis (10% gel), the proteins are stained with colloidal blue using a method compatible with mass spectrometry analysis (FIG. 10). The band of interest corresponding to the protein detected by western blot is cut out using a scalpel and then de-stained by incubation in a 25 mM ammonium bicarbonate solution. After reduction (DTT)/alkylation (iodoacetamide) and "in gel" hydrolysis (overnight at 37° C.) of the protein by trypsin (Promega), a proteolytic enzyme that hydrolyzes proteins at the Lysine and Arginine residues and thus releases peptides having a Lysine or Arginine residue in the C-terminal position, the peptides generated are extracted using an acetonitrile/water mixture (70/30, v/v) in the presence of formic acid. These are then deposited on the MALDI target in a mixture with a matrix (alpha-cyano-4-hydroxycinnamic acid, Bruker Daltonics) and in the presence of ATFA, and then analyzed by MALDI-TOF mass spectrometry (Autoflex, Bruker Daltonics). The mass spectrum obtained is presented in FIG. 10. The list of the peptides deduced from this analysis is used to identify the protein by searching data banks using the Mascot search engine (Matrix Sciences).

The NCBInr data bank search results, restricted to proteins of human origin, indicate that three proteins have a significant score (score >64):

1. Crystal structure of human junctional adhesion molecule type 1
   Score=116
   This protein corresponds to the extracellular domain of the F11R/JAM-A protein used for structural studies.
2. F11 receptor (*Homo sapiens*)
   Score=116
   This protein corresponds to the precursor of protein F11R/isoform a.
3. F11 receptor isoform b (*Homo sapiens*)
   Score=65

This is the precursor of the isoform b of protein F11R, with two deletions of 20 amino acids with respect to isoform a.

The identified protein, by this approach, is thus called F11R or F11 receptor. This is in fact the official designation of the protein adopted when it was first described as a receptor of a so-called F11 antibody (Naik et al., 1995, Biochem. J., 310, 155-162). This protein is better known today under the name of JAM-A or "junctional adhesion molecule A", and is also called JAM1, PAM-1, CD321 or antigen 106.

Among the peptides released by tryptic hydrolysis and analyzed by mass spectrometry, nine peptides have an experimental molecular weight corresponding, within 0.1 Da, to that of peptides arising from the theoretical hydrolysis of the human form of JAM-A/isoform a. These nine peptides cover 37% of the protein's primary sequence. Moreover, the theoretical molecular weight of the JAM-A precursor (~32.9 kDa) is in agreement with the apparent molecular weight determined experimentally by SDS-PAGE.

Confirmation of the Target Identified by Western Blot:

The identification of JAM-A by a proteomic approach was then confirmed by western blot (10% SDS-PAGE gel in non-reducing conditions, 6F4 antibody at 0.5 µg/ml, detection by chemiluminescence).

As shown in FIG. 11A, the 6F4 antibody recognizes natural JAM-A protein in the HT-29 membrane extract and in the fraction enriched by immunopurification (apparent MW=35 kDa), as well as the dimeric recombinant protein JAM-A/Fc (R&D Systems ref. 1103-JM, apparent MW ~120 kDa). This recognition is equivalent to that of a commercial anti-human JAM-A goat polyclonal antibody (R&D Systems, ref. AF1103) diluted to 1/1000 (FIG. 11B).

Example 5

Specificity of the 6F4 Antibody for Human JAM-A

The specificity of the 6F4 antibody was determined by western blot under the conditions described above.

FIG. 12 shows that the 6F4 antibody is specific for the human form of JAM-A since it recognizes the recombinant protein hJAM-A/Fc (R&D Systems ref. 1103-JM), but recognizes neither the human forms of JAM-B and JAM-C (recombinant proteins hJAM-B/Fc and hJAM-C/Fc, R&D Systems ref. 1074-VJ and 1189-J3) nor the murine form of JAM-A (recombinant protein mJAM-A/Fc, R&D Systems ref. 1077-JM).

Example 6

Measurement of the Affinity of the 6F4 Antibody by BIAcore (Surface Plasmon Resonance)

Principle:

Using BIAcore, the affinity constant $K_D$ (M) of the 6F4 antibody for the soluble protein JAM-1-Fc (extracellular domain fused with a Fc fragment of the antibody and produced in recombinant form in NS0 cells) can be calculated from the determination of the association kinetics ($k_a$) (1/m·s) and the dissociation kinetics ($k_d$) (1/s) according to the formula $K_D = k_d/k_a$ (Rich and Myszka, J. Mol. Recog., 2005, 18, 431).

Materials and Methods:

Instrument Used: BIAcore X and BIAevaluation 3.1× Software (Uppsala, SW)

Reagents:
  Murine monoclonal 6F4 antibody: 1.3 mg/ml
  Human JAM-1-Fc (ref. 1103-JM R&D Systems): 50 µg carrier-free)
  Mouse JAM-1-Fc (ref. 1077-JM R&D Systems): 50 µg carrier-free
  Running buffer: HBS-EP (BIAcore)
  Binding kit: "Amine" (BIAcore)
  Binding buffer: Acetate pH 5.0 (BIAcore)
  Capturing antibody: goat IgG Fc anti-human (=GAH, goat anti-human) (Bioscience)
  Regeneration buffer: Glycine, HCl pH 1.5 for 30 seconds (BIAcore).

Discussion and Conclusions

Figure 13:
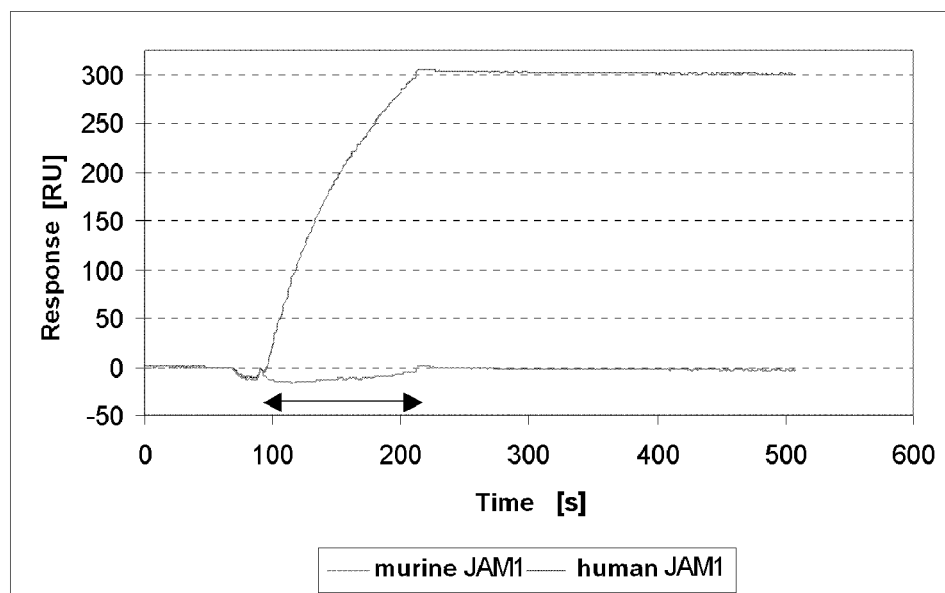
FIG. 13 is sensorgrams obtained after 2 minutes of injection (double arrow) of the 6F4 antibody at 100 nm in HBS-EP buffer on murine JAM1 Fc protein (Flow cell #1, bottom graph) and on murine JAM1 Fc protein (Flow cell #2, top graph) with a dissociation time at 25° C. of 5 minutes and a flow rate of 30 µl/min (CM4: m-JAM1-Fc 501.6 RU (Fc1) and 511.5 RU (Fc2)).

The data in FIG. 13 show that the murine 6F4 antibody is bound to the extracellular part of the human JAM-1 protein but not to the extracellular part of the murine JAM-1 protein.

Figure 14:
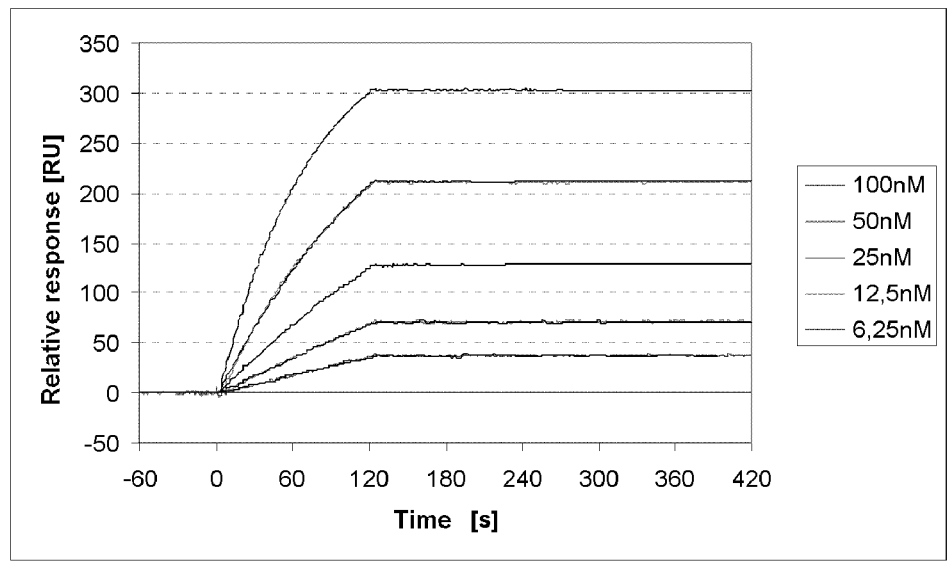
FIG. 14 is sensorgrams obtained with a double reference, (Fc2-Fc1)6F4(Fc2-Fc1)HBS-EP. The curve is fitted using a Langmuir A+B binding model. The calculated kinetic parameters (black curve) are as follows: ka=$(1.38\pm0.001)*10^5$ $M^{-1}$ $s^{-1}$; kd=$(0.25\pm1.58)*10^{-6}$ $s^{-1}$; Rmax (global fitting)=371 RU; $\square^2$=0.853.

The data in FIG. 14 make it possible to calculate a $K_D$ of 22 pM of the 6F4 antibody for the human JAM-1 protein under these experimental conditions.

The slow dissociation kinetics indicates the involvement of a phenomenon of antibody avidity for the antigen (divalent analytical model).

Example 7

In Vivo Activity of the 6F4 Antibody in the MCF-7 Xenograft Model

Figure 15:
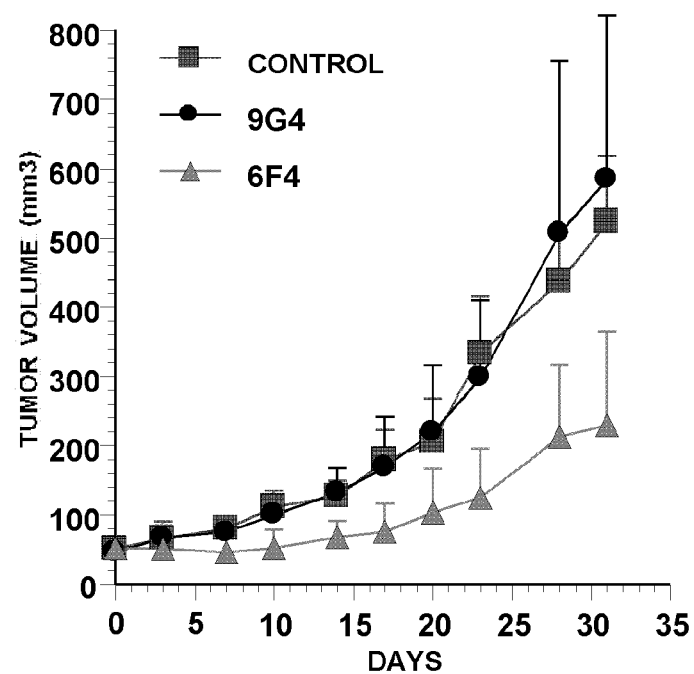
FIG. 15 illustrates the antitumor activity of the 6F4 antibody in a xenograft model of MCF-7 cells in the Swiss nude mouse. The 6F4 antibody was tested by IP route in unpurified form (peritoneal cavity fluid), at the theoretical dose of 250 µg/mouse, twice per week. The 9G4 antibody is an antibody of the same isotype (IgG1), non-relevant with respect to the activity measured.

A test of the 6F4 antibody, unpurified and injected by IP route at a dose of 250 μg/mouse, demonstrates that this antibody significantly inhibits the growth of MCF-7 cells in vivo with inhibition percentages reaching 56% compared to mice injected with PBS (FIG. 15). The non-relevant 9G4 antibody used as an IgG1 control isotype is, as expected, without antitumor activity.

Example 8

Study of the Distribution of the Antigen Recognized by 6F4 on a Panel of Tumor Cells In order to determine the potential indications for the 6F4 antibody, four types of tumors were studied by flow cytometry in terms of a membrane expression profile. The selected cell lines are MCF-7 (estrogen-related breast cancer), A549 (non-small cell lung cancer), HT29 and Colo 205 (colon cancer) and BxPC3 (pancreatic cancer). For labeling cells, a range of doses (10 μg/ml, 5 μg/ml, 1 μg/ml, 0.5 μg/ml, 0.25 μg/ml and 0.125 μg/ml) was tested.

Figure 16:
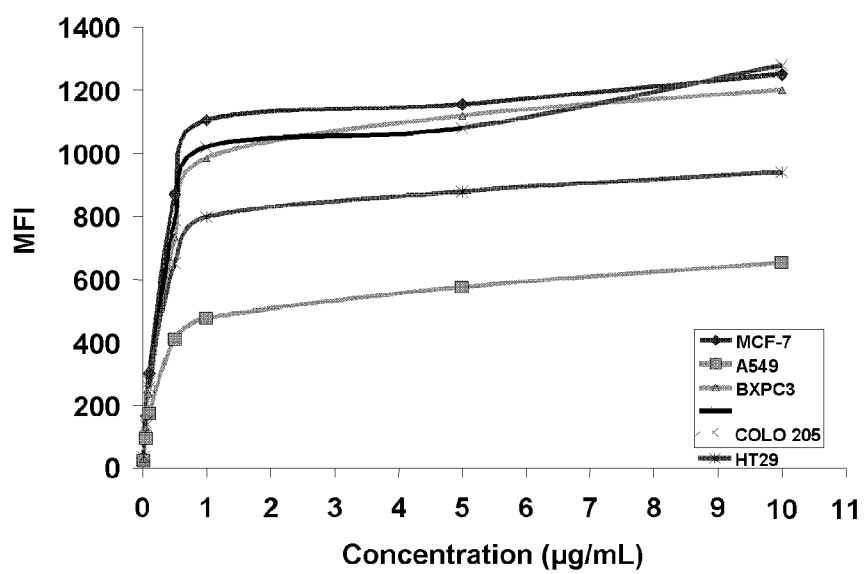
FIG. 16 illustrates JAM-A protein expression recognized by Mab 6F4 on the surface of various tumor lines.

The results presented in FIG. 16 show that the 6F4 antibody recognizes an antigen significantly expressed on the surface of all cells tested. The labeling obtained is saturable, which attests to its specificity. Saturation of the sites is obtained from a concentration of 1 μg/ml of antibody, which is evidence that the 6F4 antibody's affinity for the JAM-A antigen is high.

Example 9

Humanization by CDR-Grafting of the Variable Region of the Light Chain of the 6F4 Antibody (6F4 VL)

Summary of the Immunogenetic Analysis:

| Result summary: | Productive IGK rearranged sequence (no stop codon and in frame junction) | | |
|---|---|---|---|
| V-GENE and allele | IGKV1-33*01 | score = 922 | identity = 81.36% (227/279 nt) |
| J-GENE and allele | IGKJ1*01 | score = 140 | identity = 86.49% (32/37 nt) |
| CDR-IMGT lengths and AA JUNCTION | [6, 3, 8] | CLQYDNLWTF (SEQ ID NO: 103) | |

Detailed Data for Closest Human V-Gene Identification:

Closest V-REGIONs (evaluated from the V-REGION first nucleotide to the 2nd-CYS codon plus 15 nt of the CDR3-IMGT)

| | Score | Identity |
|---|---|---|
| M64856 IGKV1-33*01 | 922 | 81.36% (227/279 nt) |
| M64855 IGKV1D-33*01 | 922 | 81.36% (227/279 nt) |
| X63398 IGKV1-27*01 | 868 | 79.21% (221/279 nt) |
| Y14865 IGKV1-NL1*01 | 841 | 78.14% (218/279 nt) |
| X72817 IGKV1D-43*01 | 841 | 78.14% (218/279 nt) |

Detailed Data for Closest Human J-Gene Identification: Closest J-REGIONs:

| | Score | Identity |
|---|---|---|
| J00242 IGKJ1*01 | 140 | 86.49% (32/37 nt) |
| AF103571 IGKJ4*02 | 122 | 81.08% (30/37 nt) |
| J00242 IGKJ4*01 | 113 | 78.38% (29/37 nt) |
| Z70260 IGKJ2*02 | 104 | 75.68% (28/37 nt) |
| Z46620 IGKJ2*04 | 95 | 72.97% (27/37 nt) |

Identification of Critical Residues:

Several criteria are involved in the definition and ranking of outside CDR critical residues. These include at least, known participation of the residue in VH/VL interface, in antigen binding or in CDR structure, the amino acid class changes from murine and human residues, localization of the residue in the 3D structure of a variable domain etc.

21 amino acids are found different from 6F4 VL domain and the closest IGKV1-33*01 human germline V gene, all of them being outside CDR residues. Out of these 21 residues, analysis of the above cited parameters lead to the identification of 9 most potentially contributing residues. These murine residues are K24, I39, A40, H55, T66, Q68, A69, R85 and Y87. Out of these 9 residues, 3 of them are supposed to be even more important so that they will keep their murine origin in the humanized form. These are residues I39 and H55 and T66, located at the CDR1 and CDR2 anchors, respectively. Finally, 6 amino acids will be analysed individually and/or in combination to determine whether they can be humanized or if they have to keep their murine origin.

Looking to the non-involvement of the J-region in antigen binding and structuration of the V-region, it was decided to use the native human IGKJ1*01 germline gene.

In the designed sequence of the humanized 6F4 VL domain depicted in FIG. 17:

*, correspond to amino acids changed de facto to their human counterparts 1, correspond to amino acids analysed for their abilities to be humanized, the human residue being indicated below the sign 2, correspond to amino acids that remain murin in the humanized 6F4 VH domain Example 10

First Version of Humanization by CDR-Grafting of the Variable Region of the Heavy Chain of the 6F4 Antibody (6F4 VH)

Summary of the Immunogenetic Analysis:

| Result summary: | Productive IGH rearranged sequence (no stop codon and in frame junction) | | |
|---|---|---|---|
| V-GENE and allele | IGHV1-f*01 | score = 796 | identity = 75.35% (217/288 nt) |

| | | |
|---|---|---|
| J-GENE and allele | IGHJ4*01 | score = 181  identity = 87.23% (41/47 nt) |
| CDR-IMGT lengths and AA JUNCTION | [8, 8, 9] | CARQTDYFDYW (SEQ ID NO: 104) |

D-gene strictly belongs to the CDR3 region in the VH domain. The humanization process is based on a <<CDR-grafting>> approach. Analysis of the closest human D-genes is not useful in this strategy.
Detailed Data for Closest Human V-Gene Identification:
Closest V-REGIONs (evaluated from the V-REGION first nucleotide to the 2nd-CYS codon)

| | Score | Identity |
|---|---|---|
| Z12305 IGHV1-f*01 | 796 | 75.35% (217/288 nt) |
| X62106 IGHV1-2*02 | 787 | 75.00% (216/288 nt) |
| X92208 IGHV1-2*03 | 782 | 74.65% (215/288 nt) |
| Z12310 IGHV1-2*04 | 778 | 74.65% (215/288 nt) |
| M99642 IGHV1-24*01 | 760 | 73.96% (213/288 nt) |

Detailed Data for Closest Human J-Gene Identification:
Closest J-REGIONs:

| | Score | Identity |
|---|---|---|
| J00256 IGHJ4*01 | 181 | 87.23% (41/47 nt) |
| X86355 IGHJ4*02 | 172 | 85.11% (40/47 nt) |
| M25625 IGHJ4*03 | 172 | 85.11% (40/47 nt) |
| J00256 IGHJ1*01 | 138 | 74.51% (38/51 nt) |
| J00256 IGHJ5*01 | 133 | 74.00% (37/50 nt) |

Identification of Critical Residues:

Several criteria are involved in the definition and ranking of outside CDR critical residues. These include at least, known participation of the residue in VH/VL interface, in antigen binding or in CDR structure, the amino acid class changes from murine and human residues, localization of the residue in the 3D structure of a variable domain etc.

31 amino acids are found different from 6F4 VH domain and the closest IGHV1-f*01 human germline V gene, all of them being outside CDR residues. Out of these 31 residues, analysis of the above cited parameters lead to the identification of 9 most potentially contributing residues. These murine residues are I2, Y40, I53, Y55, R66, N68, Q69, K72 and K82. Out of these 9 residues, 2 of them are supposed to be even more important so that they will keep their murine origin in the humanized form. These are residues Y55 and R66, located at the CDR2 anchors. Finally, 7 amino acids will be analysed individually and/or in combination to determine whether they can be humanized or if they have to keep their murine origin.

Looking to the non-involvement of the J-region in antigen binding and structuration of the V-region, it was decided to use the native human IGHJ4*01 germline gene.

In the designed sequence of the humanized 6F4 VH domain depicted in FIG. 18:

*, correspond to amino acids changed de facto to their human counterparts 1, correspond to amino acids analysed for their abilities to be humanized, the human residue being indicated below the sign 2, correspond to amino acids that remain murin in the humanized 6F4 VH domain Example 11

Second Version of Humanization by CDR-Grafting of the Variable Region of the Heavy Chain of the 6F4 Antibody (6F4 VH)

An other way to identify human V-gene candidates for CDR-grafting was to look for human homologies at the amino acid level using IMGT/DomainGapAlign tool.
Results of the IMGT/DomainGapAlign Immunogenetic Analysis are Summarized Hereinafter:

| Allele | Species | Domain | Smith-Waterman Score | Identity percentage | Overlap |
|---|---|---|---|---|---|
| IGHV1-3*01 | Homo sapiens | 1 | 451 | 64.3 | 98 |

Identification of critical residues in IGHV1-03*01 germline gene (SEQ ID No. 49, EMBL nomenclature: X62109).

The alignment of 6F4 VH domain and IGHV1-3*01 proteic sequences is represented in FIG. 31.

The selection and ranking of those residues is based on differential criteria based on the relative importance of each single position according to their structural relevance, their known structure-function relationship, the relevance of the amino acid class change if it happen and it also take advantage of the results obtained during the first humanization process.

In a first intention, all the different "out-side CDRs" amino acids have been changes for their human counterparts, except residues Y55 and R66 which both are strongly supposed to be involved in binding as CDR2-anchors assigned residues. Humanizability of those two residues will be explored at the end of the process, when all the other analyses described after will be performed. Indeed, recovery of the fully activity of the parental antibody, the 6F4 Hz2 re-humanized VH domain would have to be improved as follow; a "de-humanization" process would consist in back mutating, if necessary, these amino acids in their murine counterpart:

The first group residues, namely E1Q, K43R and K75R present a strong combination of criteria and correspond to the first positions that "de-humanization" will be assessed if looking for a benefit.

Then, residues from group 2, namely K48Q, S49R, F88Y and H90R, are chemically relevant mutations but structurally a little less supposed key residues and will be tested in a second round of experiment.

The six residues from the third group, are presumably more involved in an overall and/or core-oriented residues and thus supposed to be less involved in binding and thus be explored in a third round of improving, whenever necessary.

Residues from the group 4, are supposed to be the less structurally and/or amino acid class change relevant and for who "de-humanization" would be explored lately.

Finally, the following six residues, I2V, Y40H, I53M, N68S, K72Q and K82T, correspond to amino acids that humanization did not, at least in this initial combination, alter binding activity of the firstly humanized VH domain. "De-humanization" of these residues will be performed in a last round of improving.

D-gene strictly belongs to the CDR3 region in the VH domain. The humanization process is based on a <<CDR-grafting>> approach. Analysis of the closest human D-genes is not useful in this strategy.

Looking to the non-involvement of the J-region in antigen binding and structuration of the V-region, it was decided to use the native human IGHJ4*01 germline gene.

Experimental Data Obtained for the Re-Humanized 6F4 Antibody:

In the following experiments, the re-humanization only concern the heavy chain, the light chain always corresponding to the QTY/AET humanized 6F4 VL domain as exemplified in example 9 this finally selected humanized VL domain exhibits an anti-JAM-a binding activity similar to that of the recombinant chimeric 6F4 antibody. Similarly, the re-humanized version improvement assays were performed with reference to recombinant chimeric 6F4 antibody anti-JAM-a binding activity as defined by an ELISA assay (data not showed).

Example 12

In Vitro Down-Regulation of JAM-A Expression by the 6F4 MAb

MCF-7, HT29 and A549 cell lines were selected to determine the effect of the 6F4 MAb on JAMA expression. Briefly cells were plated in 75 cm² flasks and incubated at 37° C., in 5% $CO_2$ atmosphere, for 24 hours, in medium supplemented with 10% Fecal Calf Serum (FCS). Then cells were washed 3 times with PBS and incubated for an additional day in serum-free medium. After this second incubation, the serum-free medium was removed and replaced by fresh serum-free medium alone or fresh serum-free medium containing either 6F4 or an IgG1 isotype control described as 9G4. After either 5 or 16 hours of incubation, cold lysis buffer (10 mM Tris HCl buffer, pH 7.5, 15% NaCl 1 M (Sigma Chemical Co.), 10% detergent mix (10 mM Tris-HCl, 10% Igepal lysis buffer) (Sigma Chemical Co.), 5% sodium deoxycholate (Sigma Chemical Co.), 1 protease inhibitor cocktail complete TM tablet (Roche) and 1% phosphatase inhibitor Cocktail Set II (Calbiochem), pH 7.5) was added and cells were scrapped on ice. The lysates were clarified by centrifugation at 4° C. Protein was quantified by BCA protein assay and 25 µg of protein were loaded in each lane of a Biorad 4-12% Bis-Tris gel. Samples were heated for 5 minutes at 100° C. and kept at −20° C. or loaded directly on 4-12% SDS-PAGE gels and transferred to nitrocellulose membrane. Blots were first blocked with 5% BSA for all antibodies. Incubation of specific anti-JAMA primary antibody was performed for 2 hours at room temperature. Filters were washed in TBST and incubated with appropriate HRP-linked secondary antibodies for 1 hour at room temperature. Membranes were washed in TBST prior visualization of proteins with ECL (Amersham).

Figure 19:
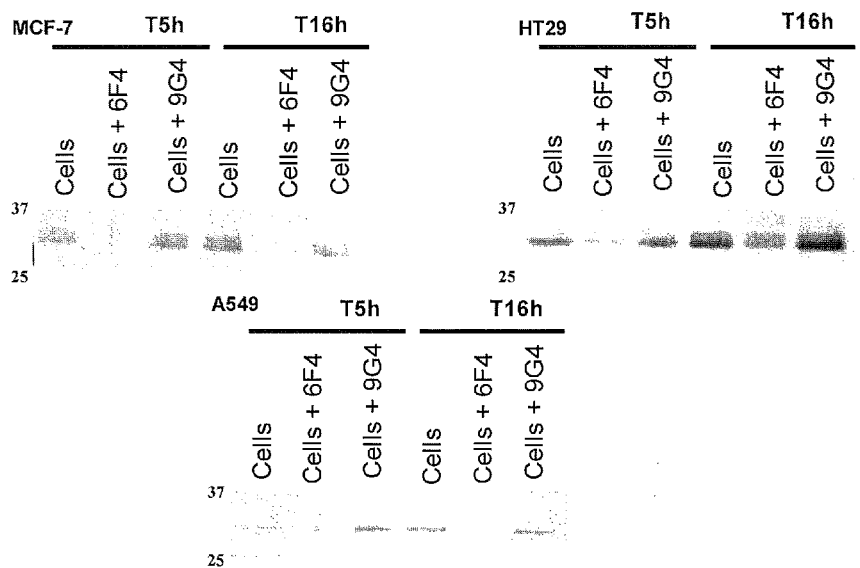
FIG. 19 illustrates the in vitro JAM-A down-regulation induced by the 6F4 MAb.

As shown in FIG. 19, a significant down-regulation of JAM-A was observed for the 3 cell lines treated with the 6F4 MAb. MCF-7 seemed to be the most sensitive one with a complete and stable down-regulation observed as early as 5 hours post 6F4 incubation. For HT29 cells a partial but sustained down-regulation of JAM-A was also noticed. The kinetic of down-regulation was different for A549 cells as no significant effect was observed at the early incubation time while a complete inhibition occurred after 16 hours of incubation with the 6F4 MAb. As expected no significant differences were observed from untreated cells and cells incubated with the 9G4 isotype control.

Example 13

Effect of a Single Injection of 6F4 on In Vivo Tumor Proliferation

To determine the in vivo mechanism of action of the 6F4 MAb, 7 weeks old female mice bearing estrogen pellets have been injected with MCF-7 cells. When tumors reached a volume of 80 to 100 mm³, 3 groups of mice with comparable tumors were generated. Before any injection, tumors were removed from one of these groups to check the basal proliferation of tumor cells within an untreated tumor. Mice from the 2 other groups were injected either with 1 mg of 6F4 or with the same dose of an IgG1 isotype control described as 9G4.

Six hours post injection, tumors were removed, fixed in formalin, paraffin embedded, cut into 5 µm sections and stained with an anti-Ki67 antibody to determine the level of proliferation in treated versus control tumors.

Figure 20:
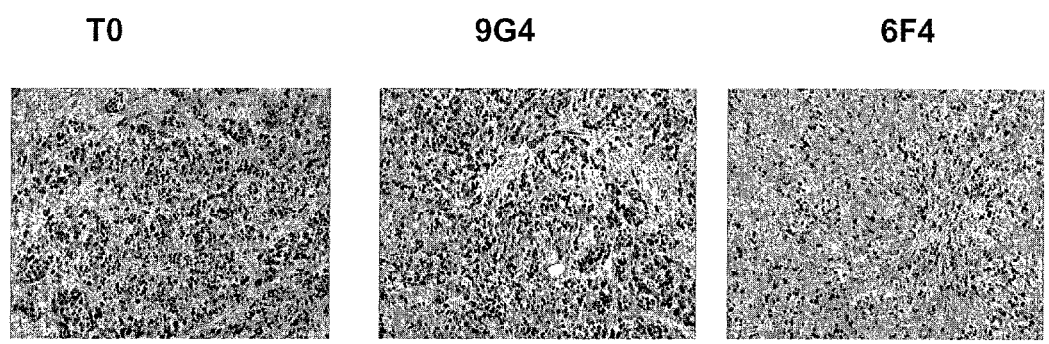
FIG. 20 illustrates the in vivo inhibition of tumor cell proliferation induced by the 6F4 MAb.

As shown in FIG. 20 no difference was observed from tumors removed before injection (described as T0 for time 0) and tumors treated with the isotype control 9G4. On the other hand, a significant inhibition of tumor cell proliferation was observed after a single injection, 6F4.

Example 14

Effect of a Single Injection of 6F4 on In Vivo JAM-A Expression

For this study the in vivo protocol is the same as the one described in in vivo proliferation experiments except that removed tumors were quickly frozen in liquid nitrogen for Western blot analysis. The Western blot was performed as described in the Example 13 above.

Figure 21:
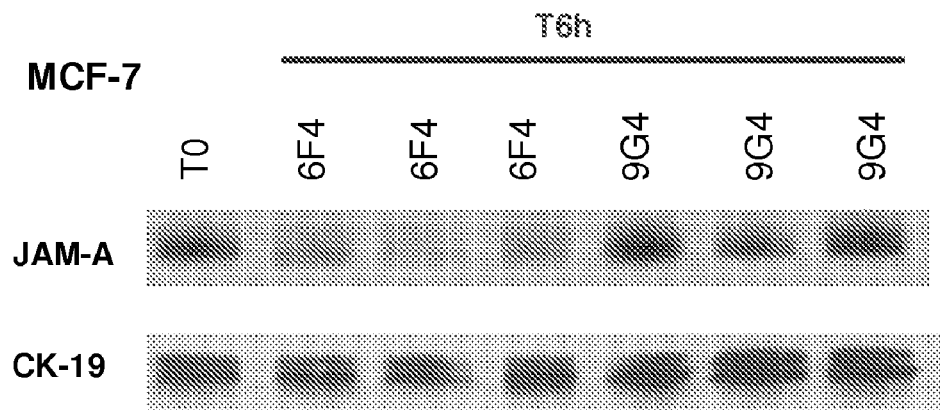
FIG. 21 is the in vivo down-regulation of JAM-A by the 6F4 Mab.

FIG. 21 demonstrate that no difference in JAM-A expression was observed from untreated mice (described as T0 for Time 0) and mice injected once with the 9G4 isotype control. A significant down-regulation was noticed when mice were treated with the 6F4 MAb indicating that a potential mechanism of action involved in the in vivo antitumor activity of this antibody could be the down-regulation of the receptor. These results were in agreement with the one observed in vitro and described below in example 13.

Example 15

Comparison of the Anti-Tumoral Activity of 6F4 and its F(ab')₂ Fragment

As JAM-A is highly expressed by MCF-7 cells and despite the fact that 6F4 is an IgG1 (isotype known to be poorly involved in effector functions in mice), an in vivo comparison from 6F4 and its F(ab')₂ fragment has been set up in the MCF-7 model to determine a potential involvement of effector functions in the in vivo activity.

For that purpose, Five millions MCF7 cells were engrafted into 7 weeks old mice female bearing estrogens pellet. Five days after cells implantation, mice were treated either with 300 µg of 6F4 or with 200 µg of 6F4 F(ab')₂ three times per week. For the first injection, 600 µg of antibody and 400 µg of 6F4 F(ab')₂ were injected. Tumor volume was measured twice a week for 4 weeks.

Figure 22:
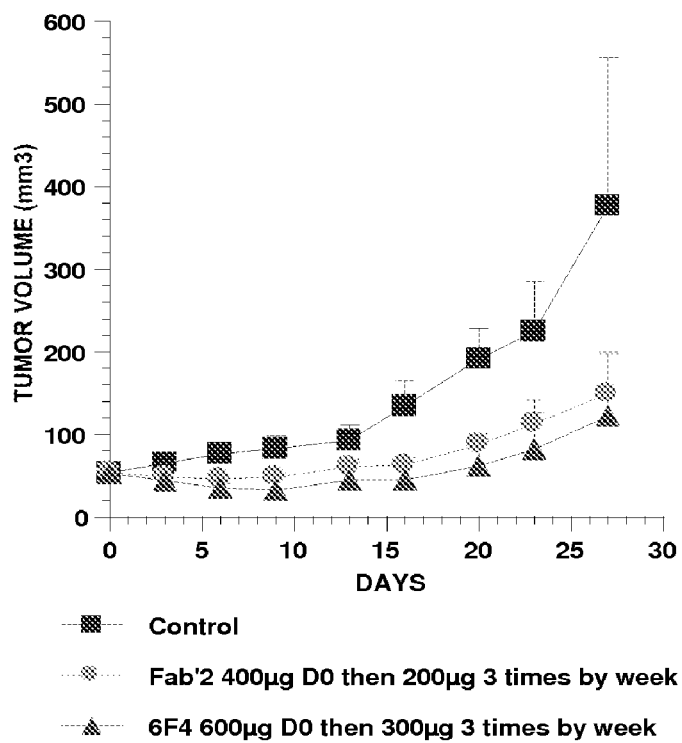
FIG. 22 is curves of the Comparison of 6F4 and its $F(ab')_2$ fragment on the MCF-7 in vivo model.

FIG. 22 showed that tumor growth in mice treated with 6F4 and 6F4 F(ab')₂ was significantly different from tumor growth of control mice from D3 to D27 ($p \leq 0.03$ for 6F4 and $p \leq 0.015$ for 6F4 F(ab')₂). No difference was observed from 6F4 and 6F4 F(ab')₂ groups of mice showing that effector functions are not involved in the 6F4 activity.

Example 16

Evaluation of the Expression of JAM-A on Human Tissue

A comparison of JAM-A expression on tumoral versus normal patient tissues has been performed to select tumor types overexpressing JAMA. Pairs of normal versus tumoral tissues from the same patient were selected for this study. In these patients normal tissues was taken near to the tumor. JAM-A expression was determined by ImmunoHistoChemistry (IHC) using tissue arrays from Superships. Briefly, Slides were dewaxed and antigen retrieval was performed using the Dakocytomation solution S1699, at 98° C. for 20 minutes. After quenching endogenous peroxidase (0.3% $H_2O_2$ solution for 5 minutes) and blocking non specific sites (Ultra-V-Block; Labvision, ref. TA-125-UB), the primary antibody (anti-hJAM-A, AF1103 from R&Dsytem or goat IgG isotype control from Zymed) was incubated for 1 hour at room temperature. After washes in TBS-tween, the binding of the anti-hJAM-A was revealed using the LSAB+ kit from dakocytomation. Visualization of the complex primary Ab and LSAB+ was performed by the chromogenic reaction HRP-DAB. Slides were then counterstained by hematoxylin.

Figure 23:
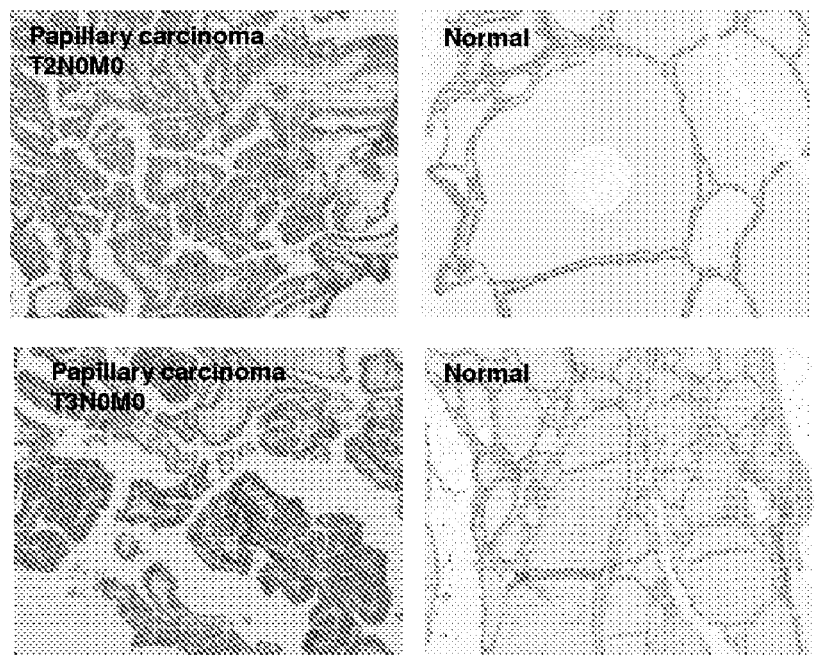
FIG. 23 illustrates the comparison of normal versus tumoral expression of JAM-A on thyroid tissues.
Figure 24:
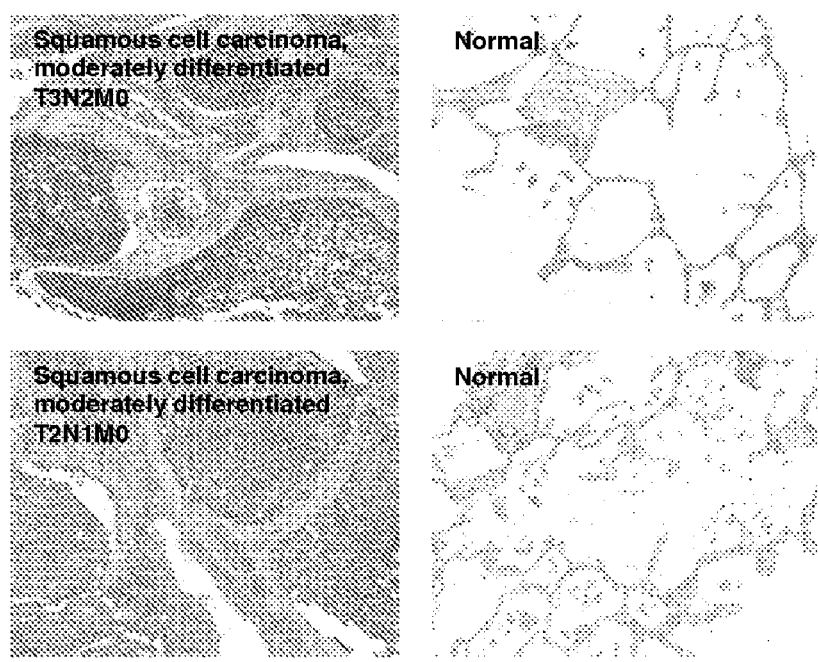
FIG. 24 illustrates the comparison of normal versus tumoral expression of JAM-A on lung tissues.
Figure 25:
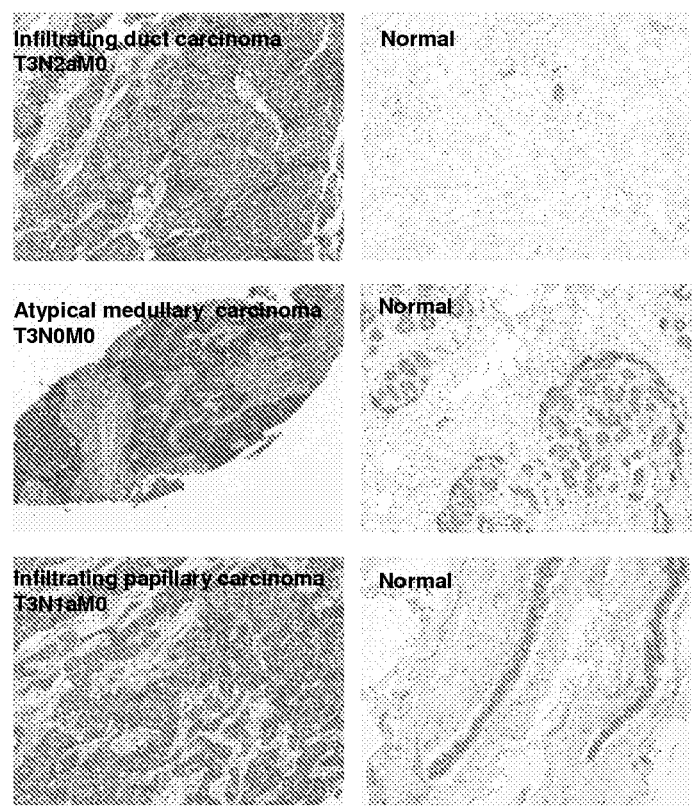
FIG. 25 illustrates the comparison of normal versus tumoral expression of JAM-A on Breast tissues.

Samples of thyroid, lung and breast cancer were analysed. For thyroid samples (FIG. 23), no expression was observed on normal thyroid tissue while JAM-A appeared to be strongly expressed in tumoral sections (membrane staining) from the same patient. In lung normal tissue JAM-A was expressed by pneumocytes. However, a strong membrane expression was observed in all tumoral samples (FIG. 24). For breast cancer, a weak JAM-A expression, located on lobular ducts, was observed on normal breast tissue. In cancer sections, the 3 examples of carcinoma shown in FIG. 25 (infiltrating duct, atypically medullary and infiltrating papillary) demonstrate that JAM-A is over expresses on breast cancer tissues.

These data suggested that thyroid, breast and lung cancers could be good targets for a JAMA therapy.

Example 17

In Vivo Activity of 6F4 on A431 Epidermoid Carcinoma Xenograft in Nude Mice

Figure 26:
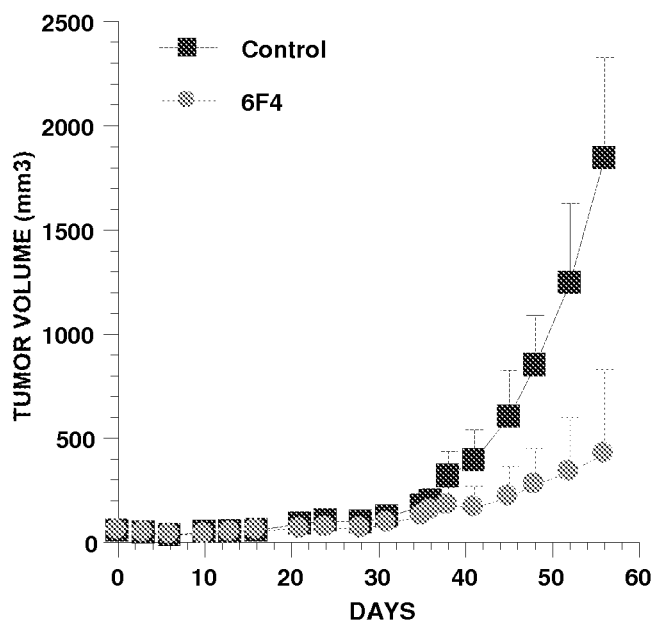
FIG. 26 is curves illustrating the in vivo activity of 6F4 on A431 epidermoid carcinoma xenograft in nude mice.

A-431 cells were routinely cultured in DMEM (Lonza) supplemented with 10% heat inactivated Fetal Calf Serum (Sigma). Cells were split two days before engraftment so that they were in exponential phase of growth. Ten million A-431 cells were engrafted on 7 weeks old Athymic Nude mice. Five days after engraftment (D5) mice were randomized and treated i.p. with the following schemes: The control group received twice a week injections of PBS and the 6F4 treated group was injected i.p. with a loading dose of 2 mg followed by twice a week injections of 1 mg dose of antibody. Tumor were measured twice a week and tumor volumes were calculated using the formula: □/6.length.width.height. Statistical analysis were performed for each time point using a Mann-Whitney Test and SigmaStat software. FIG. 26 showed that the 6F4 MAb is capable of significantly inhibiting the in vivo growth of A431 cell line (p<0.009 from day 38 to day 56).

Example 18

Evaluation of 6F4 Activity on Antigen Presentation by Antigen Presenting Cells (APC)

JAM proteins are expressed in a variety of tissues throughout the human body as well as on the surface of platelets, leukocytes, and erythrocytes [Naik 1995; Malergue 1998; Korneki 1990; Williams 1999; Gupta 2000]. JAM-A appears to be expressed in platelets, neutrophils, monocytes, lymphocytes, and erythrocytes [For review see Mandell 2005].

To determine whether a treatment with 6F4 could impair antigen presentation in patients an evaluation of a potential interference with Antigen Presenting Cells (APC) including macrophages and dendritic cells has been performed. In the presentation process, APC internalize antigens and degrade them to generate peptides which are associated within the cytoplasm with CMH class II molecules. Then the complex is expressed on APC membranes and presented to specific T lymphocytes responding to that stimulation by proliferation.

In the study presented below, the potential effect of 6F4 on Tetanus Toxoid presentation by human PBMC was evaluated. For that purpose, PBMC were isolated by Ficoll gradient centrifugation from blood. Cells were washed in PBS, counted and suspended in RPMI 1640 medium supplemented with 10% heat-inactivated foetal calf serum (FCS), glutamine and antibiotics at the concentration of $0.25.10^6$ cells/ml. 100 µl of PBMC were seeded in each well of a 96 well plate previously filled with the antigen and the antibody to be tested 10 µg/ml final concentration). The 9G4 Mab was used as an IgG1 isotype control and phytohemagglutinin PHA (2.5 µg/ml final concentration), a polyclonal activator of lymphocytes, was introduced as a positive control.

Specific antigen activator Tetanus Toxoid (TT) was selected and added to PBMC at a final concentration of 100 µg/ml. Plates were then incubated at 37° C. in an atmosphere containing 5% $CO_2$ for 96 h. Then, 0.25 µCi of [$^3$H]-Thymidine is added to the wells and incubated for 24 h. After incubation the cells were harvested, the filter membrane was dried and the amount of radioactivity was counted in a scintillation counter.

Regarding to FIGS. 27A and 28A that display the values of two independent experiments, the polyclonal activator, PHA used as a positive control of PBMC preparation is a potent inducer of lymphoproliferation, with indexes ranging from 30 and 70 depending on the donors and the experiment. In these conditions, the lymphoproliferation index was not modified whatever the antibody incubated, and 6F4 did not display any significant agonist or antagonist activity. FIGS. 27B and 28B that display the values of two independent experiments, showed that significant variations could occur from donors towards TT activation of lymphoproliferation. In these experiments, indexes ranged from 2 and 5 depending on the donors and the experiment. However, no interference on the antigen presentation was observed in presence of 6F4.

In conclusion, despite the significant expression of JAM-A on APC and lymphocyte, the use of an antibody directed against this target does not impair neither the non specific proliferation of lymphocyte nor the antigen presentation process.

Example 19

Evaluation of Platelet Aggregation and Activation after 6F4 Incubation

In order to investigate whether 6F4, which binds to human platelets, could have any biological function, two parameters were measured: platelet aggregation and serotonine release.

For this purpose, human platelets from 10 normal donors were incubated with 5 µg/ml of several antibodies to be tested.

PM6/248 (an anti-□IIb□3) have been reported to induce platelet aggregation. 9G4 was used as negative isotype control.

As expected when tested on human platelets, thrombine and ADP induced aggregation. PM6/248 also induced platelet aggregation.

Figure 29:
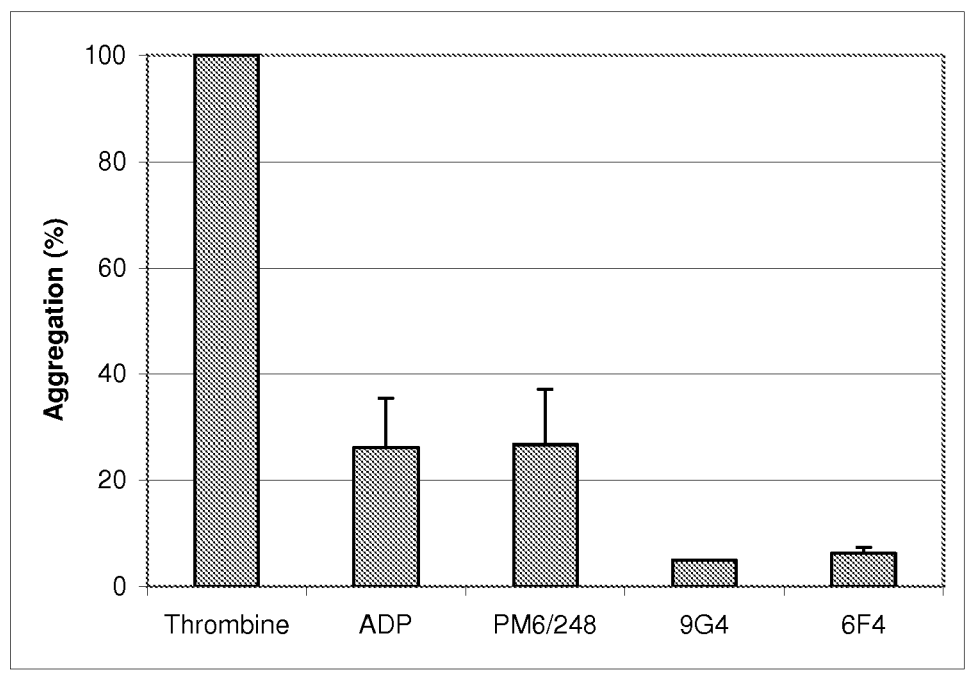
FIG. 29 illustrates the platelet aggregation on 10 human normal donors. Results are expected as mean+/−sd.

No platelet aggregation was measured after incubation with 6F4. The effect was comparable to the one observed with 9G4, used as positive control (FIG. 29).

Figure 30:
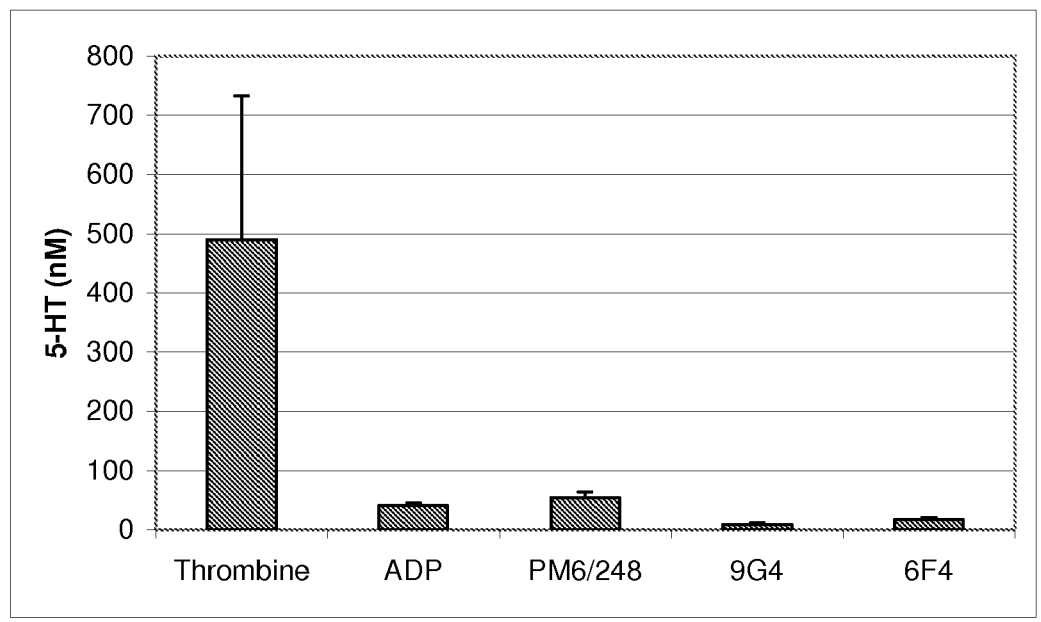
FIG. 30 is the serotonine release on 10 human normal donors. Results are expected as mean+/−sd.

In a similar way, 6F4 was not able to induce serotonine release (FIG. 30) whereas thrombine induced, as expected, 5-HT release.

All together, these results indicate that whereas JAM-A is expressed, no biological function is triggered on human platelet after 6F4 activation.

Example 20

Humanization by CDR-Grafting of the Variable Region of the Light Chain of the 6F4-Back Up Antibody (6F4-Bu)

Detailed Data for Closest Human Gene Identification:

In order to identify alternative human candidates for the CDR grafting, human germline genes displaying the best identity with the 6F4 VL have been searched. To this end, the nucleotidic sequence of 6F4 VL has been aligned with the human germline genes sequences part of the IMGT database. For optimization of the selection, alignments from the proteic sequences were also made to search for better homologies.

For the J region, the best homology score was obtained with the human IGKJ1*01 showing a nucleotidic sequence identity of 86.49%. Thus the IGKJ1*01 germline gene was selected as receiving human J region for the murine 6F4 VL CDRs. IGKV1-27*01 and IGKV1D-43*01 human V genes were selected for further use as human framework sequence for CDR-grafting.

|  | % Identity |
| --- | --- |
| IGKV1-27*01 | 79.21% (221/279 nt) |
| IGKV1D-43*01 | 78.14% (218/279 nt) |

Humanization of the 6F4 VL Domain by CDR-Grafting:

Given the possibility of two receiving human V regions for the murine 6F4 VL CDRs, 2 humanized versions of the 6F4 VL domain will be described.
a) IGKV1-27*01 Based Humanized Version of 6F4 VL (BU-L1)

The following steps in the humanization process consist in linking the selected germline genes sequences IGKV1-27*01 and IGKJ1*01 and also the CDRs of the murine 6F4 VL to the frameworks of these germline genes sequences.

As depicted in FIG. 32, the bolded residues in the 6F4 VL sequence corresponds to the twenty-one amino acids that were found different from 6F4 VL domain and the selected human frameworks (Human FR, i.e. IGKV1-27*01 and IGKJ1*01).

FIG. 32 is the implemented IGKV1-27*01 based humanized 6F4 VL with the described mutations clearly identified. The number under each proposed mutation corresponds to the rank at which said mutation will be done.

The numbering of amino acids and subsequent mutations correspond to the IMGT numbering system in FIG. 32. For example, residue 33 in the sequence listing (linear numbering) corresponds to residue 39 in the FIG. 32 (IMGT numbering).

Regarding to several criteria such as their known participation in VH/VL interface, in antigen binding or in CDR structure, the amino acid class changes from murine and human residues, localization of the residue in the 3D structure of the variable domain, four out of the twenty-one different residues have been identified to be eventually mutated. These four most important defined residues and mutations into their human counterparts being murine K24 into human R, I39 into L, H54 into Y and Y87 into F. These ranked one residues are shown in FIG. 32 as bolded residues in the 6F4 BU-L1 humanized VL sequence where they remained murine.

Of course, the above mentioned residues to be tested are not limited but must be considered as preferential mutations.

With the help of a molecular model, other mutations could be identified. Can be mentioned the following ranked two residues, i.e. residues 17 (G/D), 44 (H/Q), 69 (A/S), 85 (R/T), 89 (F/L), 93 (N/S) and 115 (G/Q) on which mutations could also be envisaged in another preferred embodiment.

The above mentioned residues to be eventually tested are not limited but must be considered as preferential mutations. In another preferred embodiment, all the ten others ranked three residues among the twenty-one different amino acids could be reconsidered.

All the above mentioned mutations will be tested individually or according various combinations.
b) IGKV1D-43*01 Based Humanized Version of 224G11 VL (BU-L2)

The following steps in the humanization process consist in linking the selected germline genes sequences IGKV1D-43*01 and IGKJ1*01 and also the CDRs of the murine 6F4 VL to the frameworks of these germline genes sequences.

As depicted in FIG. 33, the bolded residues in the 6F4 VL sequence correspond to the twenty-seven amino acids that were found different from 6F4 VL domain and the selected human frameworks (Human FR, i.e. IGKV1D-43*01 and IGKJ1*01). FIG. 33 is the implemented IGKV1D-43*01 based humanized 6F4 VL with the described mutations clearly identified. The number under each proposed mutation corresponds to the rank at which said mutation will be done.

The numbering of amino acids and subsequent mutations correspond to the IMGT numbering system in FIG. 33. For example, residue 33 in the sequence listing (linear numbering) corresponds to residue 39 in the FIG. 33 (IMGT numbering).

Regarding to several criteria such as their known participation in VH/VL interface, in antigen binding or in CDR structure, the amino acid class changes from murine and human residues, localization of the residue in the 3D structure of the variable domain, six out of the twenty-seven different residues have been identified to be eventually mutated. These six most important defined residues and mutations into their human counterparts being murine D1 into human A, Q3 into R, K24 into W, I39 into L, H55 into Y and T66 into S. These ranked one residues are shown in FIG. 33 as bolded residues in the 6F4 BU-L2 humanized VL sequence where they remained murine. Of course, the above mentioned residues to be tested are not limited but must be considered as preferential mutations.

With the help of a molecular model, other mutations could be identified. Can be mentioned the following ranked two residues, i.e. residues 9 (S/F), 17 (G/D), 44 (H/Q), 53 (L/F), 69 (A/S), 85 (R/T), 89 (F/L), 93 (N/S) and 115 (G/Q) on which mutations could also be envisaged in another preferred embodiment.

The above mentioned residues to be eventually tested are not limited but must be considered as preferential mutations. In another preferred embodiment, all the twelve others ranked three residues among the twenty-seven different amino acids could be reconsidered.

All the above mentioned mutations will be tested individually or according various combinations.

Example 21

Humanization by CDR-Grafting of the Variable Region of the Heavy Chain of the 6F4-Back Up Antibody (6F4-BU)

Detailed Data for Closest Human Gene Identification:

In order to identify alternative human candidates for the CDR grafting, human germline genes displaying the best identity with the 6F4 VH have been searched. To this end, the nucleotidic sequence of 6F4 VH has been aligned with the human germline genes sequences part of the IMGT database. For optimization of the selection, alignments from the proteic sequences were also made to search for better homologies.

For the J region, the best homology score was obtained with the human IGHJ4*01 showing a nucleotidic sequence identity of 87.23%. Thus the IGHJ*01 germline gene was selected as receiving human J region for the murine 6F4 VH CDRs. IGHV1-3*01 and IGHV1-46*01 human V genes were selected for further use as human framework sequence for CDR-grafting.

|  | % Identity |
| --- | --- |
| IGHV1-46*01 | 73.61% (212/288 nt) |
| IGHV1-3*01 | 64.30% (63/98 aa) |

Humanization of the 6F4 VH Domain by CDR-Grafting:

Given the possibility of two receiving human V regions for the murine 6F4 VH CDRs, 2 humanized versions of the 6F4 VH domain will be described.

a) IGHV1-3*01 Based Humanized Version of 6F4 VH (BU-H1)

The following steps in the humanization process consist in linking the selected germline genes sequences IGHV1-3*01 and IGHJ4*01 and also the CDRs of the murine 6F4 VH to the frameworks of these germline genes sequences.

As depicted in FIG. 34, the bolded residues in the 6F4 VH sequence corresponds to the thirty amino acids that were found different from 6F4 VH domain and the selected human frameworks (Human FR, i.e. IGHV1-3*01 and IGHJ4*01). FIG. 34 is the implemented IGHV1-3*01 based humanized 6F4 VL with the described mutations clearly identified. The number under each proposed mutation corresponds to the rank at which said mutation will be done.

The numbering of amino acids and subsequent mutations correspond to the IMGT numbering system in FIG. 34. For example, residue 44 in the sequence listing (linear numbering) corresponds to residue 49 in the FIG. 34 (IMGT numbering).

Regarding to several criteria such as their known participation in VH/VL interface, in antigen binding or in CDR structure, the amino acid class changes from murine and human residues, localization of the residue in the 3D structure of the variable domain, nine out of the thirty different residues have been identified to be eventually mutated. These nine most important defined residues and mutations into their human counterparts being murine E1 into human Q, Q5 into V, S49 into R, Y55 into W, R66 into K, A76 into V, L78 into I, V80 into R and H90 into R. These ranked one residues are shown in FIG. 34 as bolded residues in the 6F4 BU-H1 humanized VH sequence where they remained murine. It must be noted that the above mentioned residues to be tested are not limited but must be considered as preferential mutations.

With the help of a molecular model, other mutations could be identified. Can be mentioned the following ranked two residues, i.e. residues 2 (I/V), 9 (A/P), 40 (Y/H), 46 (H/P), 53 (I/M) and 84 (S/A) on which mutations could also be envisaged in another preferred embodiment.

Of course, the above mentioned residues to be eventually tested are not limited but must be considered as preferential mutations. In another preferred embodiment, all the fifteen others ranked three residues among the thirty different amino acids could be reconsidered.

All the above mentioned mutations will be tested individually or according various combinations.

b) IGHV1-46*01 Based Humanized Version of 6F4 VH (BU-H2)

The following steps in the humanization process consist in linking the selected germline genes sequences IGHV1-46*01 and IGHJ4*01 and also the CDRs of the murine 6F4 VH to the frameworks of these germline genes sequences.

As depicted in FIG. 35, the bolded residues in the 6F4 VH sequence correspond to the thirty-one amino acids that were found different from 6F4 VH domain and the selected human frameworks (Human FR, i.e. IGHV1-46*01 and IGHJ4*01). FIG. 35 is the implemented IGHV1-46*01 based humanized 6F4 VL with the described mutations clearly identified. The number under each proposed mutation corresponds to the rank at which said mutation will be done.

The numbering of amino acids and subsequent mutations correspond to the IMGT numbering system in FIG. 35. For example, residue 44 in the sequence listing (linear numbering) corresponds to residue 49 in the FIG. 35 (IMGT numbering).

Regarding to several such as their known participation in VH/VL interface, in antigen binding or in CDR structure, the amino acid class changes from murine and human residues, localization of the residue in the 3D structure of the variable domain, nine out of the thirty different residues have been identified to be eventually mutated. These nine most important defined residues and mutations into their human counterparts being murine E1 into human Q, Q5 into V, S49 into G, Y55 into I, R66 into S, A76 into V, L78 into M, V80 into R and H90 into E. These ranked one residues are shown in FIG. 35 as bolded residues in the 6F4 BU-H2 humanized VH sequence where they remained murine. Of course, the above mentioned residues to be tested are not limited but must be considered as preferential mutations.

With the help of a molecular model, other mutations could be identified. Can be mentioned the following ranked two residues, i.e. residues 2 (I/V), 9 (A/P), 40 (Y/H), 46 (H/P) and 53 (I/M) on which mutations could also be envisaged in another preferred embodiment. It must be notice that the above mentioned residues to be eventually tested are not limited but must be considered as preferential mutations. In another preferred embodiment, all the sixteen others ranked three residues among the thirty-one different amino acids could be reconsidered.

All the above mentioned mutations will be tested individually or according various combinations.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An isolated antibody capable of specifically binding to JAM-A or a binding protein or antigen binding fragment of said antibody, wherein it comprises a heavy chain comprising the three CDRs of SEQ ID NOs. 2, 4, and 6 and a light chain comprising the three CDRs of SEQ ID NOs. 1, 3, and 5.

2. The antibody or binding protein or antigen binding fragment according to claim 1, wherein it is capable of inhibiting the proliferation of tumor cells in vitro and/or in vivo.

3. The antibody or binding protein or antigen binding fragment according to claim 1, wherein it consists of a monoclonal antibody.

4. The antibody or binding protein or antigen binding fragment according to claim 1, wherein it comprises, according to IMGT,
a light chain comprising the following three CDRs:
   CDR-L1 of the sequence SEQ ID NO:1;
   CDR-L2 of the sequence SEQ ID NO:3; and
   CDR-L3 of the sequence SEQ ID NO:5, and
a heavy chain comprising the following three CDRs:
   CDR-H1 of the sequence SEQ ID NO:7;
   CDR-H2 of the sequence SEQ ID NO:4; and
   CDR-H3 of the sequence SEQ ID NO:12.

5. The antibody or binding protein or antigen binding fragment according to claim 1, wherein it comprises, according to Kabat,
a light chain comprising the following three CDRs:
   CDR-L1 of the sequence SEQ ID NO:8;
   CDR-L2 of the sequence SEQ ID NO:10; and
   CDR-L3 of the sequence SEQ ID NO:5, and
a heavy chain comprising the following three CDRs:
   CDR-H1 of the sequence SEQ ID NO:9;
   CDR-H2 of the sequence SEQ ID NO:11; and
   CDR-H3 of the sequence SEQ ID NO:6.

6. The antibody or binding protein or antigen binding fragment according to claim 1, wherein it comprises a light chain sequence comprising the amino acid sequence SEQ ID NO:13 and a heavy chain sequence comprising the amino acid sequence SEQ ID NO:14.

7. The antibody or binding protein or antigen binding fragment according to claim 1, wherein it is humanized and it comprises a light chain sequence comprising the amino acid sequence SEQ ID NO:17 and a heavy chain sequence comprising the amino acid sequence SEQ ID NO:18 or SEQ ID NO:19.

8. The antibody or binding protein or antigen binding fragment according to claim 1, wherein it is humanized and it comprises a heavy chain variable domain comprising amino acid sequence SEQ ID NO:65 or SEQ ID NO:66.

9. The antibody or binding protein or antigen binding fragment according to claim 1, wherein it is humanized and it comprises a light chain variable domain comprising amino acid sequence SEQ ID NO:67 or SEQ ID NO:68.

10. The antibody or binding protein or antigen binding fragment according to claim 1, wherein said binding fragment is selected among the fragments Fv, Fab, (Fab')$_2$, Fab', scFv, scFv-Fc and diabodies, or any fragment whose half-life has been increased such as pegylated fragments.

11. The antibody or binding protein or antigen binding fragment according to claim 1, wherein said antibody is a murine antibody and comprises a light chain of amino acid sequence SEQ ID NO:15 and a heavy chain of amino acid sequence SEQ ID NO:16.

12. The antibody or binding protein or antigen binding fragment according to claim 1, wherein it has a Kd for the JAM-A protein from roughly 1 nM and 1 pM, more preferentially from 10 pM and 40 pM.

13. The antibody or binding protein or antigen binding fragment according to claim 1, for use as a drug.

14. A composition comprising as an active ingredient a compound consisting of an antibody or binding protein or antigen binding fragment according to claim 1.

15. The composition according to claim 14, further comprising, as a combination product for use in a simultaneous, separated, or extended fashion, an antitumor antibody other that an antibody directed against JAM-A protein.

16. The composition according to claim 14, further comprising, as a combination product for use in a simultaneous, separated, or extended fashion, a cytotoxic/cytostatic agent.

17. The composition according to claim 16, wherein said cytotoxic/cytostatic agent is chemically bound with at least one of the elements of said composition for simultaneous use.

18. The composition according to claim 14, wherein at least one of said antibodies, or the binding proteins, or functional fragments of said antibodies, is conjugated with a cellular toxin and/or a radioisotope.

19. The composition according to claim 14, for use as a drug.

20. A murine hybridoma filed with the CNCM, Pasteur Institute, Paris, Jul. 6, 2006, under number 1-3646.

21. An antibody secreted by the hybridoma according to claim 20.

* * * * *